(12) United States Patent
Herlyn et al.

(10) Patent No.: US 7,811,993 B2
(45) Date of Patent: Oct. 12, 2010

(54) METHODS AND COMPOSITIONS FOR TREATING MELANOMA

(75) Inventors: Dorothee Herlyn, Wynnewood, PA (US); Rajasekaran Somasundaram, West Chester, PA (US); Laszlo Otvos, Jr., Audubon, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 551 days.

(21) Appl. No.: 11/922,467

(22) PCT Filed: Jun. 28, 2006

(86) PCT No.: PCT/US2006/025324

§ 371 (c)(1),
(2), (4) Date: Dec. 18, 2007

(87) PCT Pub. No.: WO2007/002811

PCT Pub. Date: Jan. 4, 2007

(65) Prior Publication Data

US 2010/0203109 A1 Aug. 12, 2010

Related U.S. Application Data

(60) Provisional application No. 60/694,871, filed on Jun. 29, 2005.

(51) Int. Cl.
*A61K 38/00* (2006.01)
*C07K 7/00* (2006.01)

(52) U.S. Cl. .................. 514/14; 530/327; 530/328; 435/7.23; 435/7.1; 514/15

(58) Field of Classification Search ................ None
See application file for complete search history.

(56) References Cited

OTHER PUBLICATIONS

Purev E, et al., "Immune responses of breast cancer patients to mutated epidermal growth factor receptor (EGF-RvIII, ΔEGF-R, and de2-7 EGF-R)", J. Immunol. 173(10):6472-6480 (Nov. 2004).
Ruiz PJ, et al. "Idiotypic immunization induces immunity to mutated p53 and tumor rejection", Nat. Med., 4(6):710-712 (Jun. 1998).
Fenton RG, et al, "Induction of T-cell immunity against Ras oncoproteins by soluble protein or Ras-expressing *Escherichia coli*", J. Natl. Cancer. Inst., 87(24):1853-1861 (Dec. 1995).
Khleif SN, et al., "A phase 1 vaccine trial with peptides reflecting *ras* oncogene mutations of solid tumors", J. Immunother., 22(2):155-165 (Mar. 1999).

Moscatello DK, et al., "A naturally occurring mutant human epidermal growth factor receptor as a target for peptide vaccine immunotherapy of tumors", Cancer Res., 57:1419-1424 (Apr. 1997).
Pinilla-Ibarz J, et al., "CML vaccines as a paradigm of the specific immunotherapy of cancer", Blood Rev., 14:111-120 (Jun. 2000).
Van Denderen J, et al., "Antibody recognition of the tumor-specific *bcr-abl* joining region in chronic myeloid leukemia", J. Exp. Med., 169:87-98 (Jan. 1989).
Somasundaram R, et al, "Human Leukocyte Antigen-A2—Restricted CTL responses to Mutated BRAF Peptides in Melanoma Patients", Cancer Res., 66(6):3287-3293 (Mar. 2006).
Andersen MH et al., "Immunogenicity of constitutively active $^{V599E}$BRaf", Cancer Res., 64:5456-5460 (Aug. 2004).
Marincola FM, et al., "Analysis of expression of the melanoma-associated antigens MART-1 and gp100 in metastatic melanoma cell lines and in in situ *lesions*", J. Immunother., 19(3):192-205 (May 1996).
Scanlan MJ, et al., "Characterization of human colon cancer antigens recognized by autologous antibodies", Int. J. Cancer, 76:652-658 (Jan. 1998).
Baurain JF, et al., "High frequency of autologous anti-melanoma CTL directed against an antigen generated by a point mutation in a new helicase gene", J. Immunol., 164(11):6057-6066 (Jun. 2000).
Gambacorti-Passerini C, et al., "Human CD4 lymphocytes specifically recognize a peptide representing the fusion region of the hybrid protein pml/RARa present in acute promyelocytic leukemia cells" Blood, 81(5):1369-1375 (Mar. 1993).
Wang RF and Rosenberg SA., "Human tumor antigens for cancer vaccine development", Immunol. Rev., 170:85-100 (Aug. 1999).
Brose MS et al., "*BRAF* and *RAS* mutations in human lung cancer and melanoma" Cancer Res., 62:6997-7000 (Dec. 2002).
Pollock PM, et al., "High frequency of BRAF mutations in nevi", Nat. Genet., 33:19-20 (Jan. 2003, e-publication Nov. 2002).
Michaloglou C., et al., "BRAF$^{E600}$-associated senescence-like cell cycle arrest of human naevi", Nature, 436(4):720-724 (Aug. 2005).
Sharkey MS et al, "CD4$^+$ T-cell recognition of mutated B-RAF in melanoma patients harboring the V599E mutation", Cancer Res., 64:1595-1599 (Mar. 2004).
Takahashi M, et al., "Antibody to ras proteins in patients with colon cancer", Clin. Cancer Res., 1:1071-1077 (Oct. 2005).
Davies, H, et al., "Mutations of the BRAF gene in human cancer", Nature, 417:949-954 (Jun. 2002).
Terasaki, PI and Gjertson, DW, "HLA 1997: UCLA Tissue Typing Laboratory", p. 174-427 (1997), Los Angeles, California.

*Primary Examiner*—Sheela J Huff
(74) *Attorney, Agent, or Firm*—Howson & Howson LLP

(57) ABSTRACT

Novel BRAF$^{V600E}$ mutant peptides or a pharmaceutically acceptable salt thereof, that induce MHC Class I-dependent cytotoxic T cell responses in mammals are useful in prophylactic, diagnostic and therapeutic treatments for melanoma. Such compounds are also useful in drug development for non-peptide mimics of the compounds described herein and in the development of therapeutic or diagnostic antibodies.

20 Claims, 6 Drawing Sheets

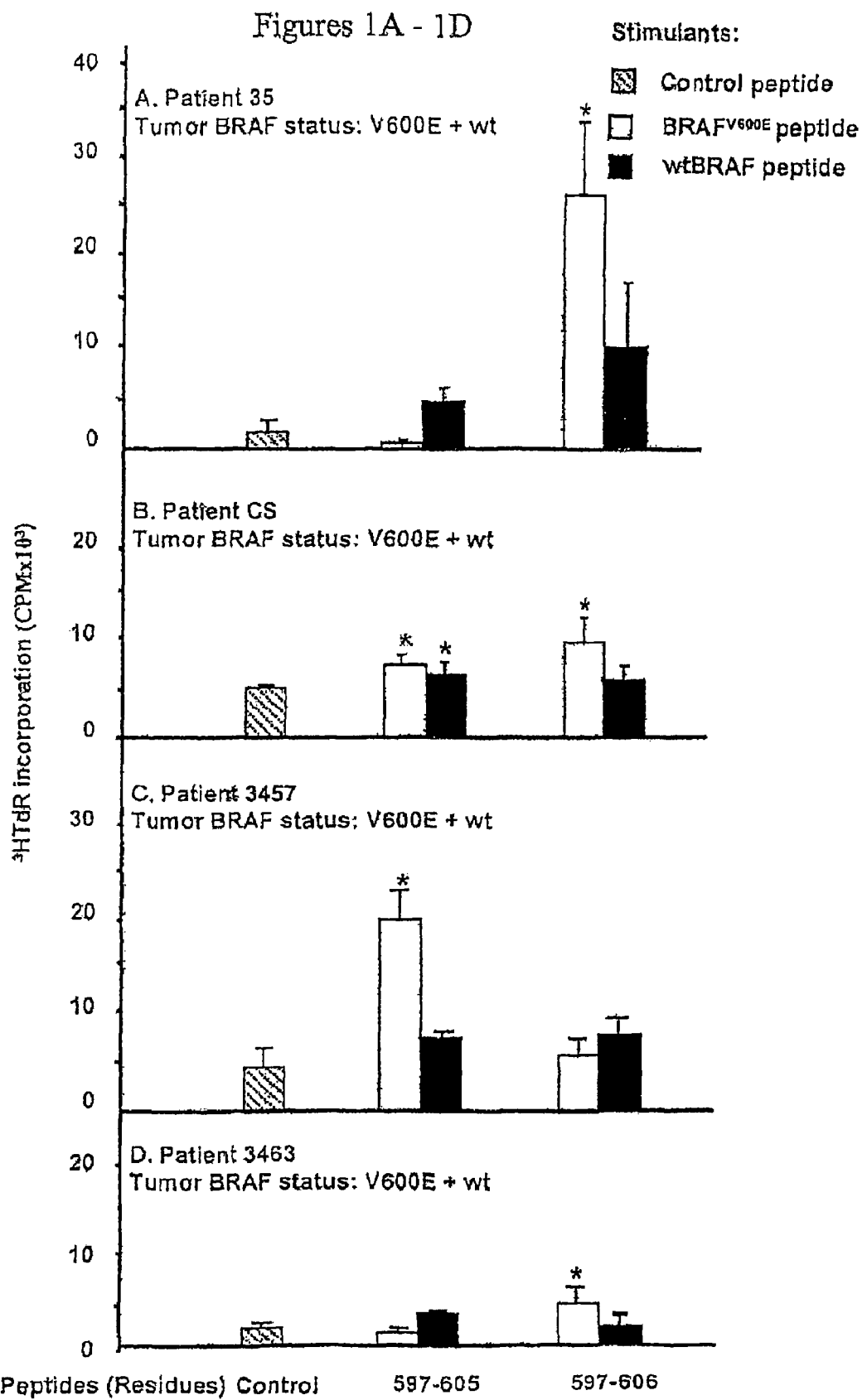

METHODS AND COMPOSITIONS FOR TREATING MELANOMA

CROSS-REFERENCE TO RELATED APPLICATIONS

This is a national stage application under 35 U.S.C. 371 of PCT/US06/025324, filed on Jun. 28, 2006, which claims the benefit under 35 USC 119(e) of U.S. patent application Ser. No. 60/694,871, filed Jun. 29, 2005.

STATEMENT REGARDING FEDERALLY SPONSORED RESEARCH OR DEVELOPMENT

This invention was made with government support under grant Nos. CA25874, CA93372 and CA10815awarded by The National Institutes of Health. The government has certain rights in the invention.

BACKGROUND OF THE INVENTION

Tumor-specific epitopes have been a recent focus in research involving cancer therapeutics. For example, mutated EGF-R (EGF-RvIII) expressed by breast cancer patients' tumors has been noted to be immunogenic in 50% of the patients (Purev E, et al. J Immunol 2004; 173:6472-80). Patients had both humoral and cellular immune responses specific for the mutated epitope. Induction of an idiotypic network against mutated p53 has resulted in tumor growth inhibition in mice (Ruiz P3, et al. Nat Med 1998; 4:710-2). Mutated ras protein/peptide vaccines have induced CTL in mice and cancer patients and have inhibited growth of established tumors in mice (Fenton R G, et al, J. Natl. Cancer Inst 1995; 87:1853-61; Khleif S N, et al. J Immunother 1999; 22:155-65). A peptide of EGF-RvIII has protected mice against challenge with tumor cells and this effect may have been mediated by CTL and/or antibodies (Moscatello D K, et al, Cancer Res 1997; 57:1419-24). Furthermore, anti-idiotypic antibodies mimicking the mutated epitope of EGF-RVIII have inhibited melanoma growth in mice through the induction of mutation-specific antibodies (Pinilla-Ibarz J, et al., Blood Rev 2000; 14:111-20). Circulating antibodies to mutated p21ras, bcr-ab1 and p53 have been observed in cancer patients (van Denderen 3, et al. J Exp Med 1989; 169:87-98; Takahashi M, et al. Clin Cancer Res 1995; 1:1071-7; and Scanlan M J, et al. Int J Cancer 1998; 76:652-8).

However, mutated tumor-specific epitopes recognized by cancer patients' T cells are usually individual-specific (Wang R F, Rosenberg S A. Immunol Rev 1999; 170:85-100; Baurain J F et al. J Immunol 2000; 164:6057-66; and Gambacorti-Passerini C, et al., Blood 1993; 81:1369-75), and therefore they do not provide immunotherapeutic targets for a larger population of patients.

BRAF is an intracellular signaling protein expressing frequently in melanomas for which alleles were identified as somatic mutations in 70% of melanomas, the majority of all types of nevi, and a minority of other cancers including lung, colon and ovary carcinomas, but not in normal cells (Davies H, et al. Nature 2002; 417:949-54; Brose M S et al. Cancer Res 2002; 62:6997-7000; Pollock P M et al. Nat Genet. 2003; 33:19-20.-3). The BRAF mutations were located in exons 11 or 15, with BRAF$^{V600E}$ representing nearly all (92%) the BRAF alleles in melanoma. BRAF$^{V600E}$ was previously known as V599E and was renamed by NCBI based on newly available sequence data; accession number NM_004333.2 (Michaloglou C., et al., Nature, Aug. 4, 2005, Vol. 436, pp. 720-724), replaced by accession number NM_004333.3. BRAF$^{V600E}$ has oncogenic activity (in vitro transformation of NIH/3T3 cells, as demonstrated in colony formation assay) through activation of the MAP kinase pathway (Davies et al, cited above).

A 29-mer BRAF peptide incorporating the V600E mutation and the sequence EDLTVKIGDFGLATEKSRWSG-SHQFEQLS (SEQ ID NO: 1) was used for in vitro stimulation of lymphocytes derived from melanoma patients, generating MHC class II-restricted CD4+ T cells specific for this peptide (Sharkey M S et al, Cancer Res 2004; 64:1595-9). The patients' CD4$^+$T lymphocyte proliferation was HLA class II (DPB1*0401 or DRB1*0404)-dependent. It is unclear from this study whether the T cells were specific for the mutated epitope of BRAF$^{V600E}$.

Additionally, HLA class I (B*2705)-dependent CTL responses specific for BRAF$^{V600E}$ and unrelated to wild type (wt) BRAF have been described in melanoma patients (Andersen M H et al. Cancer Res 2004; 64:5456-60) in experiments using the 9-mer peptides FGLATEKSR and GRFGLATEK (SEQ ID NOs: 2 and 3, respectively). CTL were obtained by stimulation of lymphocytes with a modified BRAF$^{V600E}$ peptide and the CD8$^+$T cells were enriched to demonstrate CTL activity. The HLA restriction element (B*2705) used by the patients' T cells for BRAF$^{V600E}$ recognition is expressed by a low fraction of individuals (3.2% Gjertson D W, et al, HLA. Los Angeles: UCLA Tissue Typing Laboratory; 1997. p. 174-427). This low population frequency (3.2%) of the HLA restriction element (B*2705) limits the potential clinical utility of these peptides as vaccines for melanoma patients, Thus, there remains a need in the art for compounds and pharmaceutical compositions and methods useful for treatment, prevention and diagnosis of melanoma in a large majority of patients.

SUMMARY OF THE INVENTION

To meet the need in the art, novel BRAF$^{V600E}$ based peptides that induce MHC Class I, HLA-A2-dependent cytotoxic T cell responses are provided for use in prophylactic and therapeutic treatments for melanoma. More specifically, the compositions are useful in inducing responses that are not patient-specific, but that are specific for a mutation that occurs in about 70% of all melanoma patients.

In one aspect, therefore, a variety of embodiments are provided of compounds of the formula R1-Leu-AA2-AA3-Glu-AA5-AA6-AA7-Trp-AA9-AA10-R2 (SEQ ID NO: 4), wherein the definitions for the R and AA groups are disclosed below in the detailed description.

In another aspect, a pharmaceutically acceptable salt of a compound of the above formula forms a useful compound.

In still another embodiment, a composition is provided containing one or more of the compounds of the above formula in a pharmaceutically acceptable carrier, adjuvant or diluent or a combination thereof. This composition can contain other pharmaceutically acceptable components for enhancing the penetration of the compound into a cell and/or for extending its bioavailability and increasing its resistance to enzymatic degradation in vivo. Such a composition, in one embodiment, is a pharmaceutical composition. Such a composition in another embodiment is immunogenic.

In still another embodiment, a pharmaceutical composition is provided containing a therapeutically effective amount of a nucleic acid sequence encoding the peptides described herein and a pharmaceutically acceptable carrier, adjuvant or diluent or a combination thereof.

In still another embodiment, a kit is provided containing one or more of the compounds of the above formula, as well as optional components such as suitable pharmaceutically or diagnostically acceptable carriers, penetration enhancers or components for extending bioavailability and increasing its resistance to enzymatic degradation in vivo, fusion peptides, detectable reagents, physical delivery means and other similar items.

In yet another embodiment, a method of treating or preventing the development of melanoma in a mammalian subject is provided comprising administering to said subject a composition as described above.

In a further aspect, the use of a compound or composition described above in the preparation of a medicament for the treatment or prophylaxis of melanoma in a mammalian subject is provided.

In still a further aspect, vaccine compositions are provided for preventing the development of melanoma in a mammalian subject containing a compound as described herein.

Other aspects and advantages are described further in the following detailed description of the preferred embodiments thereof.

BRIEF DESCRIPTION OF THE FIGURES

FIG. 1A is a bar graph demonstrating proliferative responses of PBMC from Patient 35 to stimulation with HLA-A*0201-binding peptides of $BRAF^{V600E}$ (clear bar) and wtBRAF (black bar) and the control peptide (cross-hatched bar). The peptides along the X axis are the control (SEQ ID NO: 532); peptide 597-605, both wild type [□] (SEQ ID NO: 530) and mutant [□] (SEQ ID NO: 8); and peptide 597-606, both wild type [□] (SEQ ID NO: 531) and mutant [□] (SEQ ID NO: 9) (see Table 3). Adherent monocytes ($5 \times 10^4$/well) were pulsed for 8 h with peptides (25 μg/ml) in PLG microspheres (1 μg/ml). At the end of incubation, excess peptides were removed and the monocytes were cultured with PBMC ($1 \times 10^5$) for 5 days. Proliferative responses were determined by standard [$^3$H]TdR incorporation assay. Data are expressed as mean cpm (triplicate determinations) plus SD (bar) of [$^3$H]TdR incorporation, along the Y axis. The asterisk indicates that the value is significantly (p<0.01) different from the value obtained with the control peptide.

FIG. 1B is a bar graph illustrating the results from the experiments described in FIG. 1A for Patient CS.

FIG. 1C is a bar graph illustrating the results from the experiments described in FIG. 1A for Patient 3457.

FIG. 1D is a bar graph illustrating the results from the experiments described in FIG. 1A for Patient 3463.

DETAILED DESCRIPTION OF THE INVENTION

Figures 1E, 1F, 1G, 1H, 1I:
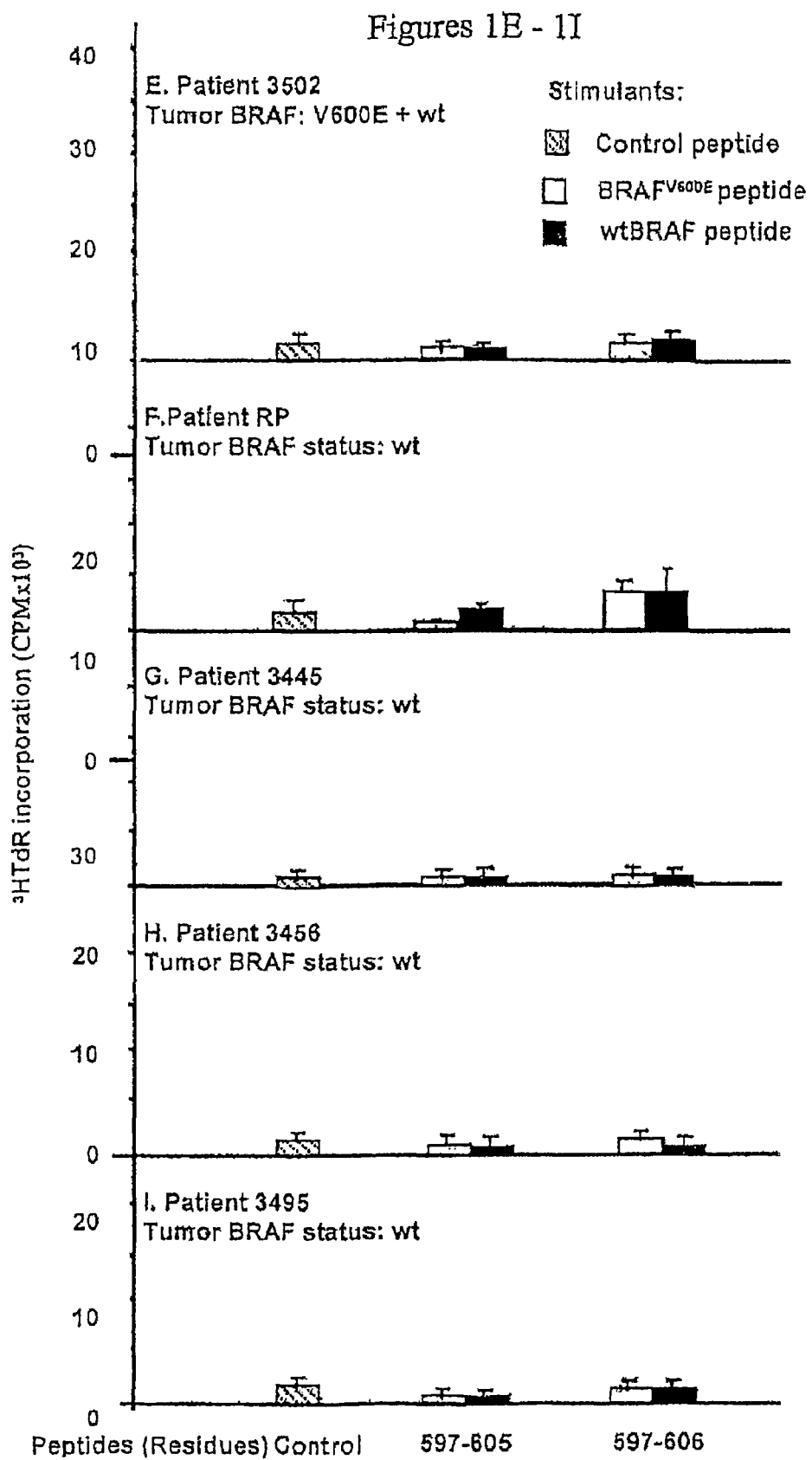
FIG. 1E is a bar graph illustrating the results from the experiments described in FIG. 1A for Patient 3502.
FIG. 1F is a bar graph illustrating the results from the experiments described in FIG. 1A for Patient RP.
FIG. 1G is a bar graph illustrating the results from the experiments described in FIG. 1A for Patient 3445.
FIG. 1H is a bar graph illustrating the results from the experiments described in FIG. 1A for Patient 3456.
FIG. 1I is a bar graph illustrating the results from the experiments described in FIG. 1A for Patient 3495.

Compositions and novel BRAF$^{V600E}$ based peptides that induce MHC Class I-dependent cytotoxic T cell responses in mammals are provided, as well as methods for using such compositions and peptides in prophylactic and therapeutic treatments for melanoma. Novel BRAF$^{V600E}$ peptides are provided, preferably 9 through 12 amino acids in length, having HLA-A*0201 binding sites.

An important question for the consideration of immunotherapies targeting mutated epitopes in cancer patients is whether the epitope expressed by patients' tumors is immunogenic in the patients. BRAF$^{V600E}$ mutation has been shown by two studies to be expressed by 70% of specimens derived from melanoma patients or in 35% of melanoma patients (Pollock et al, cited above and Marincola F M, et al. J Immunother Emphasis Tumor Immunol 1996; 19:192-205, respectively). Thus, the peptides and compositions described are designed to induce useful CTL responses in at least 50% of melanoma patients.

The following examples provide evidence supporting the use of the mutant peptides described herein as immunotherapeutic agents for such patients. For ease of discussion, the examples below employ the peptide compounds SEQ ID NO: 8 and SEQ ID NO: 9. However, as discussed herein, a wide variety of peptide analogs, as well as peptide mimetics, may be employed for the same purposes. Specifically, the inventors demonstrate use of an exemplary peptide described herein and reveal that 4 of 5 melanoma patients with BRAF$^{V600E}$-positive lesions developed lymphoproliferative responses to stimulation with the novel BRAF$^{V600E}$ peptide. These responses were specific for the mutated epitope (absence of responses to wtBRAF peptide). Proliferating lymphocytes were cytotoxic against HLA-A2positive/ BRAF$^{V600E}$-positive melanoma cells and anti-HLA-A2 antibody inhibited the proliferative lymphocyte responses in 3 patients tested. This supports the use of such peptides in compositions and methods for vaccinating HLA-A2-positive melanoma patients with the BRAF$^{V600E}$ peptides described herein.

The inventors obtained CD8$^+$CTL responses to unmodified BRAF$^{V600E}$ peptides in non-enriched CD8$^+$T cells, which is in contrast to other published peptides (see Anderson, cited above). Lymphocytes (CTL) from these 3 patients were cytotoxic against HLA-A2 matched BRAF$^{V600E}$-positive melanoma cells. CTL responses to BRAF$^{V600E}$ peptide stimulation were observed in the same 3 patients. These responses were HLA class I restricted. The BRAF$^{V600E}$ peptides described herein with binding sites for human leukocyte antigen (HLA)-A2 were used to stimulate T lymphocytes of HLA-A2-positive melanoma patients. Four of 5 patients with BRAF$^{V600E}$-positive lesions showed lymphoproliferative responses to BRAF$^{V600E}$ peptide stimulation. None of 5 patients with BRAF$^{V600E}$-negative lesions and none of 5 healthy donors had lymphoproliferative responses specific for the mutated epitope. The high prevalence (approximately 50%) of HLA-A2 among melanoma patients renders HLA-A2 restricted BRAF$^{V600E}$ peptides described herein useful in vaccine compositions and other therapeutic compositions and regimens for the treatment or prevention of melanoma. Because lymphocytic infiltration of melanoma tissues in vivo is associated with prognostically favorable disease outcome (Clemente C G, et al, Cancer 1996; 77:1303-10; Fischer W H et al., Cancer Immunol Immunother 1999; 48:363-70; Clark W H, Jr., et al. J Natl Cancer Inst 1989; 81:1893-904) and melanoma patients generally are not immunosuppressed by their tumors, immunotherapy of melanoma patients using the peptides described herein is desirable.

A. Peptides

In the following discussion, amino acids may be referred to by their conventional 3 letter designations or, for convenience, by their single letter designations. One of skill in the art is readily able to interpret the intended amino acid residue by either name.

In one aspect compounds are defined by the following formula:

(SEQ ID NO: 4)
R1-Leu-AA2-AA3-Glu-AA5-AA6-AA7-Trp-AA9-AA10-R2.

In this formula, the residue at AA2 is desirably an anchor for human lymphocyte antigen (HLA) class 1 molecules and serves to assist induction of CD8$^+$ HLA class I-restricted CTL by peptides of this formula. Such an anchor has special spatial, electronic and van-der-Waals interactions with the MHC. Thus, in one embodiment, AA2 is a substituted or unsubstituted Ala. In another embodiment, AA2 is a substituted or unsubstituted Leu. In another embodiment, AA2 is a substituted or unsubstituted Met. In another embodiment, AA2 is a substituted or unsubstituted Val. In another embodiment, AA2 is a substituted or unsubstituted Pro. In another embodiment, AA2 is a substituted or unsubstituted Gly.

In one embodiment of this formula, the residue at AA3 a substituted or unsubstituted Thr. In another embodiment, AA3 is a substituted or unsubstituted Ser.

In this formula in one embodiment the amino acid residue at AA5 is a substituted or unsubstituted Lys. In another embodiment, AA5 is a substituted or unsubstituted, Arg. In another embodiment, AA5 is a substituted or unsubstituted or His.

In this formula in one embodiment the amino acid residue at AA6 is a substituted or unsubstituted Ser. In another embodiment the amino acid residue at AA6 is a substituted or unsubstituted Thr.

In this formula in one embodiment the amino acid residue at AA7 is a substituted or unsubstituted Arg. In another embodiment the amino acid residue at AA7 is a substituted or unsubstituted Lys. In another embodiment the amino acid residue at AA7 is a substituted or unsubstituted His.

In this formula the amino acid residue at AA9 is desirably an anchor for human lymphocyte antigen (HLA) class I molecules and serves to assist induction of CD8$^+$HLA class I-restricted CTL by peptides of this formula. Thus in one embodiment, AA9 is a substituted or unsubstituted Thr. In another embodiment the amino acid residue at AA9 is a substituted or unsubstituted Val. In another embodiment the amino acid residue at AA9 is a substituted or unsubstituted Leu. In another embodiment the amino acid residue at AA9 is a substituted or unsubstituted Ser.

In this formula in one embodiment the amino acid residue at AA10 is absent. In another embodiment the amino acid residue at AA10 is a substituted or unsubstituted Gly. In another embodiment the amino acid residue at AA10 is a substituted or unsubstituted Pro. In another embodiment the amino acid residue at AA10 is a substituted or unsubstituted Leu.

Also, according to this formula, R1 and R2 are each independently absent or provide a spacer for coupling of a peptide of this formula to a second peptide or protein at the N- or C-termini of the peptide. Such spacers may be amino acid sequences or chemical compounds ordinarily used as spacers. For example, in one embodiment, R1 is a Cys; in another embodiment, R1 is a Gly-Ser. In another embodiment R2 is a Cys. In still another embodiment, R2 is a Gly-Ser. In still further embodiments, R1 and R2 are identical. In another embodiment, R1 and R2 are different.

In certain embodiments peptides, flanked by the above-described optional spacers R1 and R2, are defined by the formula Leu-AA2-Thr-Glu-Lys-Ser-Arg-Trp-Ser-AA10 (SEQ ID NO: 5), wherein AA2 is independently substituted or unsubstituted Ala, Leu, Val, Met, Pro or Gly; and wherein AA10 is independently absent, or substituted or unsubstituted Gly, Cys, Pro, or Leu. This embodiment includes peptides such as Leu-Ala-Thr-Glu-Lys-Ser-Arg-Trp-Ser (SEQ ID NO: 8), Leu-Ala-Thr-Glu-Lys-Ser-Arg-Trp-Ser-Gly (SEQ ID NO: 9), Leu-Leu-Thr-Glu-Lys-Ser-Arg-Trp-Ser-Gly (SEQ ID NO: 15), Leu-Val-Thr-Glu-Lys-Ser-Arg-Trp-Ser-Gly (SEQ ID NO: 21), Leu-Met-Thr-Glu-Lys-Ser-Arg-Trp-Ser-Gly (SEQ ID NO: 27), and Leu-Pro-Thr-Glu-Lys-Ser-Arg-Trp-Ser-Gly (SEQ ID NO: 33). Representative peptides falling within this embodiment include SEQ ID NOS: 8 to 43 of Table 1.

Still a further embodiment includes peptides Leu-Ala-Thr-Glu-Lys-Ser-Arg-Trp-Ser (SEQ ID NO: 8) and Leu Ala-Thr-Glu-Lys-Ser-Arg-Trp-Ser-Gly (SEQ ID NO: 9). Another embodiment includes peptides R1-Leu-Ala-Thr-Glu-Lys-Ser-Arg-Trp-Ser-R2 (SEQ ID NO: 533) and R1-Leu Ala-Thr-Glu-Lys-Ser-Arg-Trp-Ser-Gly-R2 (SEQ ID NO: 534). In a further embodiment, R1 or R2 are, individually, Cys or absent. In still another embodiment, both R1 and R2 are Cys. In another embodiment, R1 and R2 are both absent.

In another embodiment, peptides are defined by the formula R1-Leu-AA2-Thr-Glu-Lys-Ser-Arg-Trp-AA9-AA10-R2 (SEQ ID NO: 6), wherein R1 and R2 are described above, AA2 is independently substituted or unsubstituted Ala, Leu, Val or Met; wherein AA9 is independently substituted or unsubstituted Ser, Leu, Val, Thr, and wherein AA10 is independently absent, or substituted or unsubstituted Gly, Cys, Pro, or Leu. This embodiment includes peptides such as Leu-Ala-Thr-Glu-Lys-Ser-Arg-Trp-Leu (SEQ ID NO: 44), Leu-Ala-Thr-Glu-Lys-Ser-Arg-Trp-Leu-Gly (SEQ ID NO: 45), Leu-Ala-Thr-Glu-Lys-Ser-Arg-Trp-Val-Cys (SEQ ID NO: 54), and Leu-Ala-Thr-Glu-Lys-Ser-Arg-Trp-Thr (SEQ ID NO: 56). Representative peptides falling within this embodiment include SEQ ID NOS: 44 to 73 of Table 1.

In a further embodiment, R1 or R2 are, individually, Cys or absent. In still another embodiment, both R1 and R2 are Cys. In another embodiment, R1 and R2 are both absent.

In yet another embodiment, peptides flanked by the above-described optional spacers R1 and R2, are defined by the formula Leu-AA2-Ser-Glu-Lys-Ser-Arg-Trp-AA9-AA10 (SEQ ID NO: 7), wherein AA2 is independently substituted or unsubstituted Ala, Leu, Val or Met; wherein AA9 is independently substituted or unsubstituted Ser, Leu, Val, and wherein AA10 is independently absent, or substituted or unsubstituted Gly, Cys, Pro, or Leu. This embodiment includes peptides, such as Leu-Ala-Ser-Glu-Lys-Ser-Arg-Trp-Ser (SEQ ID NO: 74), Leu-Ala-Ser-Glu-Lys-Ser-Arg-Trp-Ser-Gly (SEQ ID NO: 75), Leu-Leu-Ser-Glu-Lys-Ser-Arg-Trp-Ser (SEQ ID NO: 80), Leu-Ala-Ser-Glu-Lys-Ser-Arg-Trp-Leu (SEQ ID NO: 111), Leu-Ala-Ser-Glu-Lys-Ser-Arg-Trp-Ser-Cys (SEQ ID NO: 78), and Leu-Leu-Ser-Glu-Lys-Ser-Arg-Trp-Val (SEQ ID NO: 123). Representative peptides falling within this embodiment include SEQ ID NOS: 74 to 134 of Table 1.

In another embodiment, peptides include R1-Leu-Ala-Thr-Glu-Lys-Ser-Arg-Trp-Ser-R2 (SEQ ID NO: 533), R1-Leu-Ala-Thr-Glu-Lys-Ser-Arg-Trp-Ser-Gly-R2 (SEQ ID NO: 534), R1-Leu-Ala-Thr-Glu-Lys-Ser-Arg-Trp-Val-R2 (SEQ ID NO: 535), R1-Leu-Ala-Thr-Glu-Lys-Ser-Arg-Trp-Val-Gly-R2 (SEQ ID NO: 536), R1-Leu-Ala-Thr-Glu-Lys-Ser-Arg-Trp-Leu-R2 (SEQ ID NO: 537), R1-Leu-Ala-Thr-Glu-Lys-Ser-Arg-Trp-Leu-Gly-R2 (SEQ ID NO: 538), R1-Leu-Leu-Thr-Glu-Lys-Ser-Arg-Trp-Ser-R2 (SEQ ID NO: 539), R1-Leu-Leu-Thr-Glu-Lys-Ser-Arg-Trp-Ser-Gly-R2 (SEQ ID NO: 540), R1-Leu-Leu-Thr-Glu-Lys-Ser-Arg-Trp-Val-R2 (SEQ ID NO: 541), R1-Leu-Leu-Thr-Glu-Lys-Ser-Arg-Trp-Val-Gly-R2 (SEQ ID NO: 542), R1-Leu-Leu-Thr-Glu-Lys-Ser-Arg-Trp-Leu-R2 (SEQ ID NO: 543), R1-Leu-Leu-Thr-Glu-Lys-Ser-Arg-Trp-Leu-Gly-R2 (SEQ ID NO: 544); R1-Leu-Val-Thr-Glu-Lys-Ser-Arg-Trp-Ser-R2 (SEQ ID NO: 545), R1-Leu-Val-Thr-Glu-Lys-Ser-Arg-Trp-Ser-Gly-R2 SEQ ID NO: 546), R1-Leu-Val-Thr-Glu-Lys-Ser-Arg-Trp-Val-R2 (SEQ ID NO: 547), R1-Leu-Val-Thr-Glu-Lys-Ser-Arg-Trp-Val-Gly-R2 (SEQ ID NO: 548), R1-Leu-Val-Thr-Glu-Lys-Ser-Arg-Trp-Leu-R2 (SEQ ID NO: 549), and R1-Leu-Val-Thr-Glu-Lys-Ser-Arg-Trp-Leu-Gly-R2 (SEQ ID NO: 550), wherein R1 and R2 are as defined above. In a further embodiment, R1 or R2 are, individually, Cys or absent. In still another embodiment, both R1 and R2 are Cys. In another embodiment, R1 and R2 are both absent.

In still other embodiments, peptides employing naturally-occurring amino acids flanked by the above-described optional spacers R1 and R2, are defined by the formulae reflected in Table 1. Still other peptides according to the formulae above are readily obvious to one of skill in the art.

TABLE 1

| Peptide | SEQ ID NO: |
|---|---|
| Leu-Ala-Thr-Glu-Lys-Ser-Arg-Trp-Ser- | 8 |
| Leu-Ala-Thr-Glu-Lys-Ser-Arg-Trp-Ser-Gly | 9 |
| Cys-Leu-Ala-Thr-Glu-Lys-Ser-Arg-Trp-Ser- | 10 |
| Cys-Leu-Ala-Thr-Glu-Lys-Ser-Arg-Trp-Ser-Gly | 11 |
| Leu-Ala-Thr-Glu-Lys-Ser-Arg-Trp-Ser-Cys | 12 |
| Leu-Ala-Thr-Glu-Lys-Ser-Arg-Trp-Ser-Gly-Cys | 13 |
| Leu-Leu-Thr-Glu-Lys-Ser-Arg-Trp-Ser- | 14 |
| Leu-Leu-Thr-Glu-Lys-Ser-Arg-Trp-Ser-Gly | 15 |

TABLE 1-continued

| Peptide | SEQ ID NO: |
|---|---|
| Cys-Leu-Leu-Thr-Glu-Lys-Ser-Arg-Trp-Ser- | 16 |
| Cys-Leu-Leu-Thr-Glu-Lys-Ser-Arg-Trp-Ser-Gly | 17 |
| Leu-Leu-Thr-Glu-Lys-Ser-Arg-Trp-Ser-Cys | 18 |
| Leu-Leu-Thr-Glu-Lys-Ser-Arg-Trp-Ser-Gly-Cys | 19 |
| Leu-Val-Thr-Glu-Lys-Ser-Arg-Trp-Ser- | 20 |
| Leu-Val-Thr-Glu-Lys-Ser-Arg-Trp-Ser-Gly | 21 |
| Cys-Leu-Val-Thr-Glu-Lys-Ser-Arg-Trp-Ser- | 22 |
| Cys-Leu-Val-Thr-Glu-Lys-Ser-Arg-Trp-Ser-Gly | 23 |
| Leu-Val-Thr-Glu-Lys-Ser-Arg-Trp-Ser-Cys | 24 |
| Leu-Val-Thr-Glu-Lys-Ser-Arg-Trp-Ser-Gly-Cys | 25 |
| Leu-Met-Thr-Glu-Lys-Ser-Arg-Trp-Ser- | 26 |
| Leu-Met-Thr-Glu-Lys-Ser-Arg-Trp-Ser-Gly | 27 |
| Cys-Leu-Met-Thr-Glu-Lys-Ser-Arg-Trp-Ser- | 28 |
| Cys-Leu-Met-Thr-Glu-Lys-Ser-Arg-Trp-Ser-Gly | 29 |
| Leu-Met-Thr-Glu-Lys-Ser-Arg-Trp-Ser-Cys | 30 |
| Leu-Met-Thr-Glu-Lys-Ser-Arg-Trp-Ser-Gly-Cys | 31 |
| Leu-Pro-Thr-Glu-Lys-Ser-Arg-Trp-Ser- | 32 |
| Leu-Pro-Thr-Glu-Lys-Ser-Arg-Trp-Ser-Gly | 33 |
| Cys-Leu-Pro-Thr-Glu-Lys-Ser-Arg-Trp-Ser- | 34 |
| Cys-Leu-Pro-Thr-Glu-Lys-Ser-Arg-Trp-Ser-Gly | 35 |
| Leu-Pro-Thr-Glu-Lys-Ser-Arg-Trp-Ser-Cys | 36 |
| Leu-Pro-Thr-Glu-Lys-Ser-Arg-Trp-Ser-Gly-Cys | 37 |
| Leu-Gly-Thr-Glu-Lys-Ser-Arg-Trp-Ser- | 38 |
| Leu-Gly-Thr-Glu-Lys-Ser-Arg-Trp-Ser-Gly | 39 |
| Cys-Leu-Gly-Thr-Glu-Lys-Ser-Arg-Trp-Ser- | 40 |
| Cys-Leu-Gly-Thr-Glu-Lys-Ser-Arg-Trp-Ser-Gly | 41 |
| Leu-Gly-Thr-Glu-Lys-Ser-Arg-Trp-Ser-Cys | 42 |
| Leu-Gly-Thr-Glu-Lys-Ser-Arg-Trp-Ser-Gly-Cys | 43 |
| Leu-Ala-Thr-Glu-Lys-Ser-Arg-Trp-Leu- | 44 |
| Leu-Ala-Thr-Glu-Lys-Ser-Arg-Trp-Leu-Gly | 45 |
| Cys-Leu-Ala-Thr-Glu-Lys-Ser-Arg-Trp-Leu- | 46 |
| Cys-Leu-Ala-Thr-Glu-Lys-Ser-Arg-Trp-Leu-Gly | 47 |
| Leu-Ala-Thr-Glu-Lys-Ser-Arg-Trp-Leu-Cys | 48 |
| Leu-Ala-Thr-Glu-Lys-Ser-Arg-Trp-Leu-Gly-Cys | 49 |
| Leu-Ala-Thr-Glu-Lys-Ser-Arg-Trp-Val- | 50 |
| Leu-Ala-Thr-Glu-Lys-Ser-Arg-Trp-Val-Gly | 51 |

TABLE 1-continued

| Peptide | SEQ ID NO: |
|---|---|
| Cys-Leu-Ala-Thr-Glu-Lys-Ser-Arg-Trp-Val- | 52 |
| Cys-Leu-Ala-Thr-Glu-Lys-Ser-Arg-Trp-Val-Gly | 53 |
| Leu-Ala-Thr-Glu-Lys-Ser-Arg-Trp-Val-Cys | 54 |
| Leu-Ala-Thr-Glu-Lys-Ser-Arg-Trp-Val-Gly-Cys | 55 |
| Leu-Ala-Thr-Glu-Lys-Ser-Arg-Trp-Thr- | 56 |
| Leu-Ala-Thr-Glu-Lys-Ser-Arg-Trp-Thr-Gly | 57 |
| Cys-Leu-Ala-Thr-Glu-Lys-Ser-Arg-Trp-Thr- | 58 |
| Cys-Leu-Ala-Thr-Glu-Lys-Ser-Arg-Trp-Thr-Gly | 59 |
| Leu-Ala-Thr-Glu-Lys-Ser-Arg-Trp-Thr-Cys | 60 |
| Leu-Ala-Thr-Glu-Lys-Ser-Arg-Trp-Thr-Gly-Cys | 61 |
| Leu-Leu-Thr-Glu-Lys-Ser-Arg-Trp-Val- | 62 |
| Leu-Leu-Thr-Glu-Lys-Ser-Arg-Trp-Val-Gly | 63 |
| Cys-Leu-Leu-Thr-Glu-Lys-Ser-Arg-Trp-Val- | 64 |
| Cys-Leu-Leu-Thr-Glu-Lys-Ser-Arg-Trp-Val-Gly | 65 |
| Leu-Leu-Thr-Glu-Lys-Ser-Arg-Trp-Val-Cys | 66 |
| Leu-Leu-Thr-Glu-Lys-Ser-Arg-Trp-Val-Gly-Cys | 67 |
| Leu-Val-Thr-Glu-Lys-Ser-Arg-Trp-Leu- | 68 |
| Leu-Val-Thr-Glu-Lys-Ser-Arg-Trp-Leu-Gly | 69 |
| Cys-Leu-Val-Thr-Glu-Lys-Ser-Arg-Trp-Leu- | 70 |
| Cys-Leu-Val-Thr-Glu-Lys-Ser-Arg-Trp-Leu-Gly | 71 |
| Leu-Val-Thr-Glu-Lys-Ser-Arg-Trp-Leu-Cys | 72 |
| Leu-Val-Thr-Glu-Lys-Ser-Arg-Trp-Leu-Gly-Cys | 73 |
| Leu-Ala-Ser-Glu-Lys-Ser-Arg-Trp-Ser- | 74 |
| Leu-Ala-Ser-Glu-Lys-Ser-Arg-Trp-Ser-Gly | 75 |
| Cys-Leu-Ala-Ser-Glu-Lys-Ser-Arg-Trp-Ser- | 76 |
| Cys-Leu-Ala-Ser-Glu-Lys-Ser-Arg-Trp-Ser-Gly | 77 |
| Leu-Ala-Ser-Glu-Lys-Ser-Arg-Trp-Ser-Cys | 78 |
| Leu-Ala-Ser-Glu-Lys-Ser-Arg-Trp-Ser-Gly-Cys | 79 |
| Leu-Leu-Ser-Glu-Lys-Ser-Arg-Trp-Ser- | 80 |
| Leu-Leu-Ser-Glu-Lys-Ser-Arg-Trp-Ser-Gly | 81 |
| Cys-Leu-Leu-Ser-Glu-Lys-Ser-Arg-Trp-Ser- | 82 |
| Cys-Leu-Leu-Ser-Glu-Lys-Ser-Arg-Trp-Ser-Gly | 83 |
| Leu-Leu-Ser-Glu-Lys-Ser-Arg-Trp-Ser-Cys | 84 |
| Leu-Leu-Ser-Glu-Lys-Ser-Arg-Trp-Ser-Gly-Cys | 85 |
| Leu-Leu-Ser-Glu-Lys-Ser-Arg-Trp-Ser- | 86 |
| Leu-Val-Ser-Glu-Lys-Ser-Arg-Trp-Ser- | 87 |
| Leu-Val-Ser-Glu-Lys-Ser-Arg-Trp-Ser-Gly | 88 |

TABLE 1-continued

| Peptide | SEQ ID NO: |
|---|---|
| Cys-Leu-Val-Ser-Glu-Lys-Ser-Arg-Trp-Ser- | 89 |
| Cys-Leu-Val-Ser-Glu-Lys-Ser-Arg-Trp-Ser-Gly | 90 |
| Leu-Val-Ser-Glu-Lys-Ser-Arg-Trp-Ser-Cys | 91 |
| Leu-Val-Ser-Glu-Lys-Ser-Arg-Trp-Ser-Gly-Cys | 92 |
| Leu-Met-Ser-Glu-Lys-Ser-Arg-Trp-Ser- | 93 |
| Leu-Met-Ser-Glu-Lys-Ser-Arg-Trp-Ser-Gly | 94 |
| Cys-Leu-Met-Ser-Glu-Lys-Ser-Arg-Trp-Ser- | 95 |
| Cys-Leu-Met-Ser-Glu-Lys-Ser-Arg-Trp-Ser-Gly | 96 |
| Leu-Met-Ser-Glu-Lys-Ser-Arg-Trp-Ser-Cys | 97 |
| Leu-Met-Ser-Glu-Lys-Ser-Arg-Trp-Ser-Gly-Cys | 98 |
| Leu-Pro-Ser-Glu-Lys-Ser-Arg-Trp-Ser- | 99 |
| Leu-Pro-Ser-Glu-Lys-Ser-Arg-Trp-Ser-Gly | 100 |
| Cys-Leu-Pro-Ser-Glu-Lys-Ser-Arg-Trp-Ser- | 101 |
| Cys-Leu-Pro-Ser-Glu-Lys-Ser-Arg-Trp-Ser-Gly | 102 |
| Leu-Pro-Ser-Glu-Lys-Ser-Arg-Trp-Ser-Cys | 103 |
| Leu-Pro-Ser-Glu-Lys-Ser-Arg-Trp-Ser-Gly-Cys | 104 |
| Leu-Gly-Ser-Glu-Lys-Ser-Arg-Trp-Ser- | 105 |
| Leu-Gly-Ser-Glu-Lys-Ser-Arg-Trp-Ser-Gly | 106 |
| Cys-Leu-Gly-Ser-Glu-Lys-Ser-Arg-Trp-Ser- | 107 |
| Cys-Leu-Gly-Ser-Glu-Lys-Ser-Arg-Trp-Ser-Gly | 108 |
| Leu-Gly-Ser-Glu-Lys-Ser-Arg-Trp-Ser-Cys | 109 |
| Leu-Gly-Ser-Glu-Lys-Ser-Arg-Trp-Ser-Gly-Cys | 110 |
| Leu-Ala-Ser-Glu-Lys-Ser-Arg-Trp-Leu- | 111 |
| Leu-Ala-Ser-Glu-Lys-Ser-Arg-Trp-Leu-Gly | 112 |
| Cys-Leu-Ala-Ser-Glu-Lys-Ser-Arg-Trp-Leu- | 113 |
| Cys-Leu-Ala-Ser-Glu-Lys-Ser-Arg-Trp-Leu-Gly | 114 |
| Leu-Ala-Ser-Glu-Lys-Ser-Arg-Trp-Leu-Cys | 115 |
| Leu-Ala-Ser-Glu-Lys-Ser-Arg-Trp-Leu-Gly-Cys | 116 |
| Leu-Ala-Ser-Glu-Lys-Ser-Arg-Trp-Val- | 117 |
| Leu-Ala-Ser-Glu-Lys-Ser-Arg-Trp-Val-Gly | 118 |
| Cys-Leu-Ala-Ser-Glu-Lys-Ser-Arg-Trp-Val- | 119 |
| Cys-Leu-Ala-Ser-Glu-Lys-Ser-Arg-Trp-Val-Gly | 120 |
| Leu-Ala-Ser-Glu-Lys-Ser-Arg-Trp-Val-Cys | 121 |
| Leu-Ala-Ser-Glu-Lys-Ser-Arg-Trp-Val-Gly-Cys | 122 |
| Leu-Leu-Ser-Glu-Lys-Ser-Arg-Trp-Val- | 123 |
| Leu-Leu-Ser-Glu-Lys-Ser-Arg-Trp-Val-Gly | 124 |

TABLE 1-continued

| Peptide | SEQ ID NO: |
|---|---|
| Cys-Leu-Leu-Ser-Glu-Lys-Ser-Arg-Trp-Val- | 125 |
| Cys-Leu-Leu-Ser-Glu-Lys-Ser-Arg-Trp-Val-Gly | 126 |
| Leu-Leu-Ser-Glu-Lys-Ser-Arg-Trp-Val-Cys | 127 |
| Leu-Leu-Ser-Glu-Lys-Ser-Arg-Trp-Val-Gly-Cys | 128 |
| Leu-Val-Ser-Glu-Lys-Ser-Arg-Trp-Leu- | 129 |
| Leu-Val-Ser-Glu-Lys-Ser-Arg-Trp-Leu-Gly | 130 |
| Cys-Leu-Val-Ser-Glu-Lys-Ser-Arg-Trp-Leu- | 131 |
| Cys-Leu-Val-Ser-Glu-Lys-Ser-Arg-Trp-Leu-Gly | 132 |
| Leu-Val-Ser-Glu-Lys-Ser-Arg-Trp-Leu-Cys | 133 |
| Leu-Val-Ser-Glu-Lys-Ser-Arg-Trp-Leu-Gly-Cys | 134 |
| Leu-Ala-Thr-Glu-Arg-Ser-Arg-Trp-Ser- | 135 |
| Leu-Ala-Thr-Glu-Arg-Ser-Arg-Trp-Ser-Gly | 136 |
| Cys-Leu-Ala-Thr-Glu-Arg-Ser-Arg-Trp-Ser- | 137 |
| Cys-Leu-Ala-Thr-Glu-Arg-Ser-Arg-Trp-Ser-Gly | 138 |
| Leu-Ala-Thr-Glu-Arg-Ser-Arg-Trp-Ser-Cys | 139 |
| Leu-Ala-Thr-Glu-Arg-Ser-Arg-Trp-Ser-Gly-Cys | 140 |
| Leu-Leu-Thr-Glu-Arg-Ser-Arg-Trp-Ser- | 141 |
| Leu-Leu-Thr-Glu-Arg-Ser-Arg-Trp-Ser-Gly | 142 |
| Cys-Leu-Leu-Thr-Glu-Arg-Ser-Arg-Trp-Ser- | 143 |
| Cys-Leu-Leu-Thr-Glu-Arg-Ser-Arg-Trp-Ser-Gly | 144 |
| Leu-Leu-Thr-Glu-Arg-Ser-Arg-Trp-Ser-Cys | 145 |
| Leu-Leu-Thr-Glu-Arg-Ser-Arg-Trp-Ser-Gly-Cys | 146 |
| Leu-Leu-Thr-Glu-Arg-Ser-Arg-Trp-Ser- | 147 |
| Leu-Val-Thr-Glu-Arg-Ser-Arg-Trp-Ser- | 148 |
| Leu-Val-Thr-Glu-Arg-Ser-Arg-Trp-Ser-Gly | 149 |
| Cys-Leu-Val-Thr-Glu-Arg-Ser-Arg-Trp-Ser- | 150 |
| Cys-Leu-Val-Thr-Glu-Arg-Ser-Arg-Trp-Ser-Gly | 151 |
| Leu-Val-Thr-Glu-Arg-Ser-Arg-Trp-Ser-Cys | 152 |
| Leu-Val-Thr-Glu-Arg-Ser-Arg-Trp-Ser-Gly-Cys | 153 |
| Leu-Met-Thr-Glu-Arg-Ser-Arg-Trp-Ser- | 154 |
| Leu-Met-Thr-Glu-Arg-Ser-Arg-Trp-Ser-Gly | 155 |
| Cys-Leu-Met-Thr-Glu-Arg-Ser-Arg-Trp-Ser- | 156 |
| Cys-Leu-Met-Thr-Glu-Arg-Ser-Arg-Trp-Ser-Gly | 157 |
| Leu-Met-Thr-Glu-Arg-Ser-Arg-Trp-Ser-Cys | 158 |
| Leu-Met-Thr-Glu-Arg-Ser-Arg-Trp-Ser-Gly-Cys | 159 |
| Leu-Pro-Thr-Glu-Arg-Ser-Arg-Trp-Ser- | 160 |
| Leu-Pro-Thr-Glu-Arg-Ser-Arg-Trp-Ser-Gly | 161 |

TABLE 1-continued

| Peptide | SEQ ID NO: |
|---|---|
| Cys-Leu-Pro-Thr-Glu-Arg-Ser-Arg-Trp-Ser- | 162 |
| Cys-Leu-Pro-Thr-Glu-Arg-Ser-Arg-Trp-Ser-Gly | 163 |
| Leu-Pro-Thr-Glu-Arg-Ser-Arg-Trp-Ser-Cys | 164 |
| Leu-Pro-Thr-Glu-Arg-Ser-Arg-Trp-Ser-Gly-Cys | 165 |
| Leu-Gly-Thr-Glu-Arg-Ser-Arg-Trp-Ser- | 166 |
| Leu-Gly-Thr-Glu-Arg-Ser-Arg-Trp-Ser-Gly | 167 |
| Cys-Leu-Gly-Thr-Glu-Arg-Ser-Arg-Trp-Ser- | 168 |
| Cys-Leu-Gly-Thr-Glu-Arg-Ser-Arg-Trp-Ser-Gly | 169 |
| Leu-Gly-Thr-Glu-Arg-Ser-Arg-Trp-Ser-Cys | 170 |
| Leu-Gly-Thr-Glu-Arg-Ser-Arg-Trp-Ser-Gly-Cys | 171 |
| Leu-Ala-Thr-Glu-Arg-Ser-Arg-Trp-Leu- | 172 |
| Leu-Ala-Thr-Glu-Arg-Ser-Arg-Trp-Leu-Gly | 173 |
| Cys-Leu-Ala-Thr-Glu-Arg-Ser-Arg-Trp-Leu- | 174 |
| Cys-Leu-Ala-Thr-Glu-Arg-Ser-Arg-Trp-Leu-Gly | 175 |
| Leu-Ala-Thr-Glu-Arg-Ser-Arg-Trp-Leu-Cys | 176 |
| Leu-Ala-Thr-Glu-Arg-Ser-Arg-Trp-Leu-Gly-Cys | 177 |
| Leu-Ala-Thr-Glu-Arg-Ser-Arg-Trp-Val- | 178 |
| Leu-Ala-Thr-Glu-Arg-Ser-Arg-Trp-Val-Gly | 179 |
| Cys-Leu-Ala-Thr-Glu-Arg-Ser-Arg-Trp-Val- | 180 |
| Cys-Leu-Ala-Thr-Glu-Arg-Ser-Arg-Trp-Val-Gly | 181 |
| Leu-Ala-Thr-Glu-Arg-Ser-Arg-Trp-Val-Cys | 182 |
| Leu-Ala-Thr-Glu-Arg-Ser-Arg-Trp-Val-Gly-Cys | 183 |
| Leu-Ala-Thr-Glu-Arg-Ser-Arg-Trp-Thr- | 184 |
| Leu-Ala-Thr-Glu-Arg-Ser-Arg-Trp-Thr-Gly | 185 |
| Cys-Leu-Ala-Thr-Glu-Arg-Ser-Arg-Trp-Thr- | 186 |
| Cys-Leu-Ala-Thr-Glu-Arg-Ser-Arg-Trp-Thr-Gly | 187 |
| Leu-Ala-Thr-Glu-Arg-Ser-Arg-Trp-Thr-Cys | 188 |
| Leu-Ala-Thr-Glu-Arg-Ser-Arg-Trp-Thr-Gly-Cys | 189 |
| Leu-Leu-Thr-Glu-Arg-Ser-Arg-Trp-Val- | 190 |
| Leu-Leu-Thr-Glu-Arg-Ser-Arg-Trp-Val-Gly | 191 |
| Cys-Leu-Leu-Thr-Glu-Arg-Ser-Arg-Trp-Val- | 192 |
| Cys-Leu-Leu-Thr-Glu-Arg-Ser-Arg-Trp-Val-Gly | 193 |
| Leu-Leu-Thr-Glu-Arg-Ser-Arg-Trp-Val-Cys | 194 |
| Leu-Leu-Thr-Glu-Arg-Ser-Arg-Trp-Val-Gly-Cys | 195 |
| Leu-Val-Thr-Glu-Arg-Ser-Arg-Trp-Leu- | 196 |
| Leu-Val-Thr-Glu-Arg-Ser-Arg-Trp-Leu-Gly | 197 |

TABLE 1-continued

| Peptide | SEQ ID NO: |
|---|---|
| Cys-Leu-Val-Thr-Glu-Arg-Ser-Arg-Trp-Leu- | 198 |
| Cys-Leu-Val-Thr-Glu-Arg-Ser-Arg-Trp-Leu-Gly | 199 |
| Leu-Val-Thr-Glu-Arg-Ser-Arg-Trp-Leu-Cys | 200 |
| Leu-Val-Thr-Glu-Arg-Ser-Arg-Trp-Leu-Gly-Cys | 201 |
| Leu-Ala-Thr-Glu-His-Ser-Arg-Trp-Ser- | 202 |
| Leu-Ala-Thr-Glu-His-Ser-Arg-Trp-Ser-Gly | 203 |
| Cys-Leu-Ala-Thr-Glu-His-Ser-Arg-Trp-Ser- | 204 |
| Cys-Leu-Ala-Thr-Glu-His-Ser-Arg-Trp-Ser-Gly | 205 |
| Leu-Ala-Thr-Glu-His-Ser-Arg-Trp-Ser-Cys | 206 |
| Leu-Ala-Thr-Glu-His-Ser-Arg-Trp-Ser-Gly-Cys | 207 |
| Leu-Leu-Thr-Glu-His-Ser-Arg-Trp-Ser- | 208 |
| Leu-Leu-Thr-Glu-His-Ser-Arg-Trp-Ser-Gly | 209 |
| Cys-Leu-Leu-Thr-Glu-His-Ser-Arg-Trp-Ser- | 210 |
| Cys-Leu-Leu-Thr-Glu-His-Ser-Arg-Trp-Ser-Gly | 211 |
| Leu-Leu-Thr-Glu-His-Ser-Arg-Trp-Ser-Cys | 212 |
| Leu-Leu-Thr-Glu-His-Ser-Arg-Trp-Ser-Gly-Cys | 213 |
| Leu-Leu-Thr-Glu-His-Ser-Arg-Trp-Ser- | 214 |
| Leu-Val-Thr-Glu-His-Ser-Arg-Trp-Ser- | 215 |
| Leu-Val-Thr-Glu-His-Ser-Arg-Trp-Ser-Gly | 216 |
| Cys-Leu-Val-Thr-Glu-His-Ser-Arg-Trp-Ser- | 217 |
| Cys-Leu-Val-Thr-Glu-His-Ser-Arg-Trp-Ser-Gly | 218 |
| Leu-Val-Thr-Glu-His-Ser-Arg-Trp-Ser-Cys | 219 |
| Leu-Val-Thr-Glu-His-Ser-Arg-Trp-Ser-Gly-Cys | 220 |
| Leu-Met-Thr-Glu-His-Ser-Arg-Trp-Ser- | 221 |
| Leu-Met-Thr-Glu-His-Ser-Arg-Trp-Ser-Gly | 222 |
| Cys-Leu-Met-Thr-Glu-His-Ser-Arg-Trp-Ser- | 223 |
| Cys-Leu-Met-Thr-Glu-His-Ser-Arg-Trp-Ser-Gly | 224 |
| Leu-Met-Thr-Glu-His-Ser-Arg-Trp-Ser-Cys | 225 |
| Leu-Met-Thr-Glu-His-Ser-Arg-Trp-Ser-Gly-Cys | 226 |
| Leu-Pro-Thr-Glu-His-Ser-Arg-Trp-Ser- | 227 |
| Leu-Pro-Thr-Glu-His-Ser-Arg-Trp-Ser-Gly | 228 |
| Cys-Leu-Pro-Thr-Glu-His-Ser-Arg-Trp-Ser- | 229 |
| Cys-Leu-Pro-Thr-Glu-His-Ser-Arg-Trp-Ser-Gly | 230 |
| Leu-Pro-Thr-Glu-His-Ser-Arg-Trp-Ser-Cys | 231 |
| Leu-Pro-Thr-Glu-His-Ser-Arg-Trp-Ser-Gly-Cys | 232 |
| Leu-Gly-Thr-Glu-His-Ser-Arg-Trp-Ser- | 233 |
| Leu-Gly-Thr-Glu-His-Ser-Arg-Trp-Ser-Gly | 234 |

TABLE 1-continued

| Peptide | SEQ ID NO: |
|---|---|
| Cys-Leu-Gly-Thr-Glu-His-Ser-Arg-Trp-Ser- | 235 |
| Cys-Leu-Gly-Thr-Glu-His-Ser-Arg-Trp-Ser-Gly | 236 |
| Leu-Gly-Thr-Glu-His-Ser-Arg-Trp-Ser-Cys | 237 |
| Leu-Gly-Thr-Glu-His-Ser-Arg-Trp-Ser-Gly-Cys | 238 |
| Leu-Ala-Thr-Glu-His-Ser-Arg-Trp-Leu- | 239 |
| Leu-Ala-Thr-Glu-His-Ser-Arg-Trp-Leu-Gly | 240 |
| Cys-Leu-Ala-Thr-Glu-His-Ser-Arg-Trp-Leu- | 241 |
| Cys-Leu-Ala-Thr-Glu-His-Ser-Arg-Trp-Leu-Gly | 242 |
| Leu-Ala-Thr-Glu-His-Ser-Arg-Trp-Leu-Cys | 243 |
| Leu-Ala-Thr-Glu-His-Ser-Arg-Trp-Leu-Gly-Cys | 244 |
| Leu-Ala-Thr-Glu-His-Ser-Arg-Trp-Val- | 245 |
| Leu-Ala-Thr-Glu-His-Ser-Arg-Trp-Val-Gly | 246 |
| Cys-Leu-Ala-Thr-Glu-His-Ser-Arg-Trp-Val- | 247 |
| Cys-Leu-Ala-Thr-Glu-His-Ser-Arg-Trp-Val-Gly | 248 |
| Leu-Ala-Thr-Glu-His-Ser-Arg-Trp-Val-Cys | 249 |
| Leu-Ala-Thr-Glu-His-Ser-Arg-Trp-Val-Gly-Cys | 250 |
| Leu-Ala-Thr-Glu-His-Ser-Arg-Trp-Thr- | 251 |
| Leu-Ala-Thr-Glu-His-Ser-Arg-Trp-Thr-Gly | 252 |
| Cys-Leu-Ala-Thr-Glu-His-Ser-Arg-Trp-Thr- | 253 |
| Cys-Leu-Ala-Thr-Glu-His-Ser-Arg-Trp-Thr-Gly | 254 |
| Leu-Ala-Thr-Glu-His-Ser-Arg-Trp-Thr-Cys | 255 |
| Leu-Ala-Thr-Glu-His-Ser-Arg-Trp-Thr-Gly-Cys | 256 |
| Leu-Leu-Thr-Glu-His-Ser-Arg-Trp-Val- | 257 |
| Leu-Leu-Thr-Glu-His-Ser-Arg-Trp-Val-Gly | 258 |
| Cys-Leu-Leu-Thr-Glu-His-Ser-Arg-Trp-Val- | 259 |
| Cys-Leu-Leu-Thr-Glu-His-Ser-Arg-Trp-Val-Gly | 260 |
| Leu-Leu-Thr-Glu-His-Ser-Arg-Trp-Val-Cys | 261 |
| Leu-Leu-Thr-Glu-His-Ser-Arg-Trp-Val-Gly-Cys | 262 |
| Leu-Val-Thr-Glu-His-Ser-Arg-Trp-Leu- | 263 |
| Leu-Val-Thr-Glu-His-Ser-Arg-Trp-Leu-Gly | 264 |
| Cys-Leu-Val-Thr-Glu-His-Ser-Arg-Trp-Leu- | 265 |
| Cys-Leu-Val-Thr-Glu-His-Ser-Arg-Trp-Leu-Gly | 266 |
| Leu-Val-Thr-Glu-His-Ser-Arg-Trp-Leu-Cys | 267 |
| Leu-Val-Thr-Glu-His-Ser-Arg-Trp-Leu-Gly-Cys | 268 |
| Leu-Ala-Thr-Glu-Lys-Thr-Arg-Trp-Ser- | 269 |
| Leu-Ala-Thr-Glu-Lys-Thr-Arg-Trp-Ser-Gly | 270 |

TABLE 1-continued

| Peptide | SEQ ID NO: |
|---|---|
| Cys-Leu-Ala-Thr-Glu-Lys-Thr-Arg-Trp-Ser- | 271 |
| Cys-Leu-Ala-Thr-Glu-Lys-Thr-Arg-Trp-Ser-Gly | 272 |
| Leu-Ala-Thr-Glu-Lys-Thr-Arg-Trp-Ser-Cys | 273 |
| Leu-Ala-Thr-Glu-Lys-Thr-Arg-Trp-Ser-Gly-Cys | 274 |
| Leu-Leu-Thr-Glu-Lys-Thr-Arg-Trp-Ser- | 275 |
| Leu-Leu-Thr-Glu-Lys-Thr-Arg-Trp-Ser-Gly | 276 |
| Cys-Leu-Leu-Thr-Glu-Lys-Thr-Arg-Trp-Ser- | 277 |
| Cys-Leu-Leu-Thr-Glu-Lys-Thr-Arg-Trp-Ser-Gly | 278 |
| Leu-Leu-Thr-Glu-Lys-Thr-Arg-Trp-Ser-Cys | 279 |
| Leu-Leu-Thr-Glu-Lys-Thr-Arg-Trp-Ser-Gly-Cys | 280 |
| Leu-Leu-Thr-Glu-Lys-Thr-Arg-Trp-Ser- | 281 |
| Leu-Val-Thr-Glu-Lys-Thr-Arg-Trp-Ser- | 282 |
| Leu-Val-Thr-Glu-Lys-Thr-Arg-Trp-Ser-Gly | 283 |
| Cys-Leu-Val-Thr-Glu-Lys-Thr-Arg-Trp-Ser- | 284 |
| Cys-Leu-Val-Thr-Glu-Lys-Thr-Arg-Trp-Ser-Gly | 285 |
| Leu-Val-Thr-Glu-Lys-Thr-Arg-Trp-Ser-Cys | 286 |
| Leu-Val-Thr-Glu-Lys-Thr-Arg-Trp-Ser-Gly-Cys | 287 |
| Leu-Met-Thr-Glu-Lys-Thr-Arg-Trp-Ser- | 288 |
| Leu-Met-Thr-Glu-Lys-Thr-Arg-Trp-Ser-Gly | 289 |
| Cys-Leu-Met-Thr-Glu-Lys-Thr-Arg-Trp-Ser- | 290 |
| Cys-Leu-Met-Thr-Glu-Lys-Thr-Arg-Trp-Ser-Gly | 291 |
| Leu-Met-Thr-Glu-Lys-Thr-Arg-Trp-Ser-Cys | 292 |
| Leu-Met-Thr-Glu-Lys-Thr-Arg-Trp-Ser-Gly-Cys | 293 |
| Leu-Pro-Thr-Glu-Lys-Thr-Arg-Trp-Ser- | 294 |
| Leu-Pro-Thr-Glu-Lys-Thr-Arg-Trp-Ser-Gly | 295 |
| Cys-Leu-Pro-Thr-Glu-Lys-Thr-Arg-Trp-Ser- | 296 |
| Cys-Leu-Pro-Thr-Glu-Lys-Thr-Arg-Trp-Ser-Gly | 297 |
| Leu-Pro-Thr-Glu-Lys-Thr-Arg-Trp-Ser-Cys | 298 |
| Leu-Pro-Thr-Glu-Lys-Thr-Arg-Trp-Ser-Gly-Cys | 299 |
| Leu-Gly-Thr-Glu-Lys-Thr-Arg-Trp-Ser- | 300 |
| Leu-Gly-Thr-Glu-Lys-Thr-Arg-Trp-Ser-Gly | 301 |
| Cys-Leu-Gly-Thr-Glu-Lys-Thr-Arg-Trp-Ser- | 302 |
| Cys-Leu-Gly-Thr-Glu-Lys-Thr-Arg-Trp-Ser-Gly | 303 |
| Leu-Gly-Thr-Glu-Lys-Thr-Arg-Trp-Ser-Cys | 304 |
| Leu-Gly-Thr-Glu-Lys-Thr-Arg-Trp-Ser-Gly-Cys | 305 |
| Leu-Ala-Thr-Glu-Lys-Thr-Arg-Trp-Leu- | 306 |
| Leu-Ala-Thr-Glu-Lys-Thr-Arg-Trp-Leu-Gly | 307 |

TABLE 1-continued

| Peptide | SEQ ID NO: |
|---|---|
| Cys-Leu-Ala-Thr-Glu-Lys-Thr-Arg-Trp-Leu- | 308 |
| Cys-Leu-Ala-Thr-Glu-Lys-Thr-Arg-Trp-Leu-Gly | 309 |
| Leu-Ala-Thr-Glu-Lys-Thr-Arg-Trp-Leu-Cys | 310 |
| Leu-Ala-Thr-Glu-Lys-Thr-Arg-Trp-Leu-Gly-Cys | 311 |
| Leu-Ala-Thr-Glu-Lys-Thr-Arg-Trp-Val- | 312 |
| Leu-Ala-Thr-Glu-Lys-Thr-Arg-Trp-Val-Gly | 313 |
| Cys-Leu-Ala-Thr-Glu-Lys-Thr-Arg-Trp-Val- | 314 |
| Cys-Leu-Ala-Thr-Glu-Lys-Thr-Arg-Trp-Val-Gly | 315 |
| Leu-Ala-Thr-Glu-Lys-Thr-Arg-Trp-Val-Cys | 316 |
| Leu-Ala-Thr-Glu-Lys-Thr-Arg-Trp-Val-Gly-Cys | 317 |
| Leu-Ala-Thr-Glu-Lys-Thr-Arg-Trp-Thr- | 318 |
| Leu-Ala-Thr-Glu-Lys-Thr-Arg-Trp-Thr-Gly | 319 |
| Cys-Leu-Ala-Thr-Glu-Lys-Thr-Arg-Trp-Thr- | 320 |
| Cys-Leu-Ala-Thr-Glu-Lys-Thr-Arg-Trp-Thr-Gly | 321 |
| Leu-Ala-Thr-Glu-Lys-Thr-Arg-Trp-Thr-Cys | 322 |
| Leu-Ala-Thr-Glu-Lys-Thr-Arg-Trp-Thr-Gly-Cys | 323 |
| Leu-Leu-Thr-Glu-Lys-Thr-Arg-Trp-Val- | 324 |
| Leu-Leu-Thr-Glu-Lys-Thr-Arg-Trp-Val-Gly | 325 |
| Cys-Leu-Leu-Thr-Glu-Lys-Thr-Arg-Trp-Val- | 326 |
| Cys-Leu-Leu-Thr-Glu-Lys-Thr-Arg-Trp-Val-Gly | 327 |
| Leu-Leu-Thr-Glu-Lys-Thr-Arg-Trp-Val-Cys | 328 |
| Leu-Leu-Thr-Glu-Lys-Thr-Arg-Trp-Val-Gly-Cys | 329 |
| Leu-Val-Thr-Glu-Lys-Thr-Arg-Trp-Leu- | 330 |
| Leu-Val-Thr-Glu-Lys-Thr-Arg-Trp-Leu-Gly | 331 |
| Cys-Leu-Val-Thr-Glu-Lys-Thr-Arg-Trp-Leu- | 332 |
| Cys-Leu-Val-Thr-Glu-Lys-Thr-Arg-Trp-Leu-Gly | 333 |
| Leu-Val-Thr-Glu-Lys-Thr-Arg-Trp-Leu-Cys | 334 |
| Leu-Val-Thr-Glu-Lys-Thr-Arg-Trp-Leu-Gly-Cys | 335 |
| Leu-Ala-Thr-Glu-Lys-Ser-Lys-Trp-Ser- | 336 |
| Leu-Ala-Thr-Glu-Lys-Ser-Lys-Trp-Ser-Gly | 337 |
| Cys-Leu-Ala-Thr-Glu-Lys-Ser-Lys-Trp-Ser- | 338 |
| Cys-Leu-Ala-Thr-Glu-Lys-Ser-Lys-Trp-Ser-Gly | 339 |
| Leu-Ala-Thr-Glu-Lys-Ser-Lys-Trp-Ser-Cys | 340 |
| Leu-Ala-Thr-Glu-Lys-Ser-Lys-Trp-Ser-Gly-Cys | 341 |
| Leu-Leu-Thr-Glu-Lys-Ser-Lys-Trp-Ser- | 342 |
| Leu-Leu-Thr-Glu-Lys-Ser-Lys-Trp-Ser-Gly | 343 |

TABLE 1-continued

| Peptide | SEQ ID NO: |
|---|---|
| Cys-Leu-Leu-Thr-Glu-Lys-Ser-Lys-Trp-Ser- | 344 |
| Cys-Leu-Leu-Thr-Glu-Lys-Ser-Lys-Trp-Ser-Gly | 345 |
| Leu-Leu-Thr-Glu-Lys-Ser-Lys-Trp-Ser-Cys | 346 |
| Leu-Leu-Thr-Glu-Lys-Ser-Lys-Trp-Ser-Gly-Cys | 347 |
| Leu-Leu-Thr-Glu-Lys-Ser-Lys-Trp-Ser- | 348 |
| Leu-Val-Thr-Glu-Lys-Ser-Lys-Trp-Ser- | 349 |
| Leu-Val-Thr-Glu-Lys-Ser-Lys-Trp-Ser-Gly | 350 |
| Cys-Leu-Val-Thr-Glu-Lys-Ser-Lys-Trp-Ser- | 351 |
| Cys-Leu-Val-Thr-Glu-Lys-Ser-Lys-Trp-Ser-Gly | 352 |
| Leu-Val-Thr-Glu-Lys-Ser-Lys-Trp-Ser-Cys | 353 |
| Leu-Val-Thr-Glu-Lys-Ser-Lys-Trp-Ser-Gly-Cys | 354 |
| Leu-Met-Thr-Glu-Lys-Ser-Lys-Trp-Ser- | 355 |
| Leu-Met-Thr-Glu-Lys-Ser-Lys-Trp-Ser-Gly | 356 |
| Cys-Leu-Met-Thr-Glu-Lys-Ser-Lys-Trp-Ser- | 357 |
| Cys-Leu-Met-Thr-Glu-Lys-Ser-Lys-Trp-Ser-Gly | 358 |
| Leu-Met-Thr-Glu-Lys-Ser-Lys-Trp-Ser-Cys | 359 |
| Leu-Met-Thr-Glu-Lys-Ser-Lys-Trp-Ser-Gly-Cys | 360 |
| Leu-Pro-Thr-Glu-Lys-Ser-Lys-Trp-Ser- | 361 |
| Leu-Pro-Thr-Glu-Lys-Ser-Lys-Trp-Ser-Gly | 362 |
| Cys-Leu-Pro-Thr-Glu-Lys-Ser-Lys-Trp-Ser- | 363 |
| Cys-Leu-Pro-Thr-Glu-Lys-Ser-Lys-Trp-Ser-Gly | 364 |
| Leu-Pro-Thr-Glu-Lys-Ser-Lys-Trp-Ser-Cys | 365 |
| Leu-Pro-Thr-Glu-Lys-Ser-Lys-Trp-Ser-Gly-Cys | 366 |
| Leu-Gly-Thr-Glu-Lys-Ser-Lys-Trp-Ser- | 367 |
| Leu-Gly-Thr-Glu-Lys-Ser-Lys-Trp-Ser-Gly | 368 |
| Cys-Leu-Gly-Thr-Glu-Lys-Ser-Lys-Trp-Ser- | 369 |
| Cys-Leu-Gly-Thr-Glu-Lys-Ser-Lys-Trp-Ser-Gly | 370 |
| Leu-Gly-Thr-Glu-Lys-Ser-Lys-Trp-Ser-Cys | 371 |
| Leu-Gly-Thr-Glu-Lys-Ser-Lys-Trp-Ser-Gly-Cys | 372 |
| Leu-Ala-Thr-Glu-Lys-Ser-Lys-Trp-Leu- | 373 |
| Leu-Ala-Thr-Glu-Lys-Ser-Lys-Trp-Leu-Gly | 374 |
| Cys-Leu-Ala-Thr-Glu-Lys-Ser-Lys-Trp-Leu- | 375 |
| Cys-Leu-Ala-Thr-Glu-Lys-Ser-Lys-Trp-Leu-Gly | 376 |
| Leu-Ala-Thr-Glu-Lys-Ser-Lys-Trp-Leu-Cys | 377 |
| Leu-Ala-Thr-Glu-Lys-Ser-Lys-Trp-Leu-Gly-Cys | 378 |
| Leu-Ala-Thr-Glu-Lys-Ser-Lys-Trp-Val- | 379 |
| Leu-Ala-Thr-Glu-Lys-Ser-Lys-Trp-Val-Gly | 380 |

TABLE 1-continued

| Peptide | SEQ ID NO: |
|---|---|
| Cys-Leu-Ala-Thr-Glu-Lys-Ser-Lys-Trp-Val- | 381 |
| Cys-Leu-Ala-Thr-Glu-Lys-Ser-Lys-Trp-Val-Gly | 382 |
| Leu-Ala-Thr-Glu-Lys-Ser-Lys-Trp-Val-Cys | 383 |
| Leu-Ala-Thr-Glu-Lys-Ser-Lys-Trp-Val-Gly-Cys | 384 |
| Leu-Ala-Thr-Glu-Lys-Ser-Lys-Trp-Thr- | 385 |
| Leu-Ala-Thr-Glu-Lys-Ser-Lys-Trp-Thr-Gly | 386 |
| Cys-Leu-Ala-Thr-Glu-Lys-Ser-Lys-Trp-Thr- | 387 |
| Cys-Leu-Ala-Thr-Glu-Lys-Ser-Lys-Trp-Thr-Gly | 388 |
| Leu-Ala-Thr-Glu-Lys-Ser-Lys-Trp-Thr-Cys | 389 |
| Leu-Ala-Thr-Glu-Lys-Ser-Lys-Trp-Thr-Gly-Cys | 390 |
| Leu-Leu-Thr-Glu-Lys-Ser-Lys-Trp-Val- | 391 |
| Leu-Leu-Thr-Glu-Lys-Ser-Lys-Trp-Val-Gly | 392 |
| Cys-Leu-Leu-Thr-Glu-Lys-Ser-Lys-Trp-Val- | 393 |
| Cys-Leu-Leu-Thr-Glu-Lys-Ser-Lys-Trp-Val-Gly | 394 |
| Leu-Leu-Thr-Glu-Lys-Ser-Lys-Trp-Val-Cys | 395 |
| Leu-Leu-Thr-Glu-Lys-Ser-Lys-Trp-Val-Gly-Cys | 396 |
| Leu-Val-Thr-Glu-Lys-Ser-Lys-Trp-Leu- | 397 |
| Leu-Val-Thr-Glu-Lys-Ser-Lys-Trp-Leu-Gly | 398 |
| Cys-Leu-Val-Thr-Glu-Lys-Ser-Lys-Trp-Leu- | 399 |
| Cys-Leu-Val-Thr-Glu-Lys-Ser-Lys-Trp-Leu-Gly | 400 |
| Leu-Val-Thr-Glu-Lys-Ser-Lys-Trp-Leu-Cys | 401 |
| Leu-Val-Thr-Glu-Lys-Ser-Lys-Trp-Leu-Gly-Cys | 402 |
| Leu-Ala-Thr-Glu-Lys-Ser-His-Trp-Ser- | 403 |
| Leu-Ala-Thr-Glu-Lys-Ser-His-Trp-Ser-Gly | 404 |
| Cys-Leu-Ala-Thr-Glu-Lys-Ser-His-Trp-Ser- | 405 |
| Cys-Leu-Ala-Thr-Glu-Lys-Ser-His-Trp-Ser-Gly | 406 |
| Leu-Ala-Thr-Glu-Lys-Ser-His-Trp-Ser-Cys | 407 |
| Leu-Ala-Thr-Glu-Lys-Ser-His-Trp-Ser-Gly-Cys | 408 |
| Leu-Leu-Thr-Glu-Lys-Ser-His-Trp-Ser- | 409 |
| Leu-Leu-Thr-Glu-Lys-Ser-His-Trp-Ser-Gly | 410 |
| Cys-Leu-Leu-Thr-Glu-Lys-Ser-His-Trp-Ser- | 411 |
| Cys-Leu-Leu-Thr-Glu-Lys-Ser-His-Trp-Ser-Gly | 412 |
| Leu-Leu-Thr-Glu-Lys-Ser-His-Trp-Ser-Cys | 413 |
| Leu-Leu-Thr-Glu-Lys-Ser-His-Trp-Ser-Gly-Cys | 414 |
| Leu-Leu-Thr-Glu-Lys-Ser-His-Trp-Ser- | 415 |
| Leu-Val-Thr-Glu-Lys-Ser-His-Trp-Ser- | 416 |
| Leu-Val-Thr-Glu-Lys-Ser-His-Trp-Ser-Gly | 417 |

TABLE 1-continued

| Peptide | SEQ ID NO: |
|---|---|
| Cys-Leu-Val-Thr-Glu-Lys-Ser-His-Trp-Ser- | 418 |
| Cys-Leu-Val-Thr-Glu-Lys-Ser-His-Trp-Ser-Gly | 419 |
| Leu-Val-Thr-Glu-Lys-Ser-His-Trp-Ser-Cys | 420 |
| Leu-Val-Thr-Glu-Lys-Ser-His-Trp-Ser-Gly-Cys | 421 |
| Leu-Met-Thr-Glu-Lys-Ser-His-Trp-Ser- | 422 |
| Leu-Met-Thr-Glu-Lys-Ser-His-Trp-Ser-Gly | 423 |
| Cys-Leu-Met-Thr-Glu-Lys-Ser-His-Trp-Ser- | 424 |
| Cys-Leu-Met-Thr-Glu-Lys-Ser-His-Trp-Ser-Gly | 425 |
| Leu-Met-Thr-Glu-Lys-Ser-His-Trp-Ser-Cys | 426 |
| Leu-Met-Thr-Glu-Lys-Ser-His-Trp-Ser-Gly-Cys | 427 |
| Leu-Pro-Thr-Glu-Lys-Ser-His-Trp-Ser- | 428 |
| Leu-Pro-Thr-Glu-Lys-Ser-His-Trp-Ser-Gly | 429 |
| Cys-Leu-Pro-Thr-Glu-Lys-Ser-His-Trp-Ser- | 430 |
| Cys-Leu-Pro-Thr-Glu-Lys-Ser-His-Trp-Ser-Gly | 431 |
| Leu-Pro-Thr-Glu-Lys-Ser-His-Trp-Ser-Cys | 432 |
| Leu-Pro-Thr-Glu-Lys-Ser-His-Trp-Ser-Gly-Cys | 433 |
| Leu-Gly-Thr-Glu-Lys-Ser-His-Trp-Ser- | 434 |
| Leu-Gly-Thr-Glu-Lys-Ser-His-Trp-Ser-Gly | 435 |
| Cys-Leu-Gly-Thr-Glu-Lys-Ser-His-Trp-Ser- | 436 |
| Cys-Leu-Gly-Thr-Glu-Lys-Ser-His-Trp-Ser-Gly | 437 |
| Leu-Gly-Thr-Glu-Lys-Ser-His-Trp-Ser-Cys | 438 |
| Leu-Gly-Thr-Glu-Lys-Ser-His-Trp-Ser-Gly-Cys | 439 |
| Leu-Ala-Thr-Glu-Lys-Ser-His-Trp-Leu- | 440 |
| Leu-Ala-Thr-Glu-Lys-Ser-His-Trp-Leu-Gly | 441 |
| Cys-Leu-Ala-Thr-Glu-Lys-Ser-His-Trp-Leu- | 442 |
| Cys-Leu-Ala-Thr-Glu-Lys-Ser-His-Trp-Leu-Gly | 443 |
| Leu-Ala-Thr-Glu-Lys-Ser-His-Trp-Leu-Cys | 444 |
| Leu-Ala-Thr-Glu-Lys-Ser-His-Trp-Leu-Gly-Cys | 445 |
| Leu-Ala-Thr-Glu-Lys-Ser-His-Trp-Val- | 446 |
| Leu-Ala-Thr-Glu-Lys-Ser-His-Trp-Val-Gly | 447 |
| Cys-Leu-Ala-Thr-Glu-Lys-Ser-His-Trp-Val- | 448 |
| Cys-Leu-Ala-Thr-Glu-Lys-Ser-His-Trp-Val-Gly | 449 |
| Leu-Ala-Thr-Glu-Lys-Ser-His-Trp-Val-Cys | 450 |
| Leu-Ala-Thr-Glu-Lys-Ser-His-Trp-Val-Gly-Cys | 451 |
| Leu-Ala-Thr-Glu-Lys-Ser-His-Trp-Thr- | 452 |
| Leu-Ala-Thr-Glu-Lys-Ser-His-Trp-Thr-Gly | 453 |

TABLE 1-continued

| Peptide | SEQ ID NO: |
|---|---|
| Cys-Leu-Ala-Thr-Glu-Lys-Ser-His-Trp-Thr- | 454 |
| Cys-Leu-Ala-Thr-Glu-Lys-Ser-His-Trp-Thr-Gly | 455 |
| Leu-Ala-Thr-Glu-Lys-Ser-His-Trp-Thr-Cys | 456 |
| Leu-Ala-Thr-Glu-Lys-Ser-His-Trp-Thr-Gly-Cys | 457 |
| Leu-Leu-Thr-Glu-Lys-Ser-His-Trp-Val- | 458 |
| Leu-Leu-Thr-Glu-Lys-Ser-His-Trp-Val-Gly | 459 |
| Cys-Leu-Leu-Thr-Glu-Lys-Ser-His-Trp-Val- | 460 |
| Cys-Leu-Leu-Thr-Glu-Lys-Ser-His-Trp-Val-Gly | 461 |
| Leu-Leu-Thr-Glu-Lys-Ser-His-Trp-Val-Cys | 462 |
| Leu-Leu-Thr-Glu-Lys-Ser-His-Trp-Val-Gly-Cys | 463 |
| Leu-Val-Thr-Glu-Lys-Ser-His-Trp-Leu- | 464 |
| Leu-Val-Thr-Glu-Lys-Ser-His-Trp-Leu-Gly | 465 |
| Cys-Leu-Val-Thr-Glu-Lys-Ser-His-Trp-Leu- | 466 |
| Cys-Leu-Val-Thr-Glu-Lys-Ser-His-Trp-Leu-Gly | 467 |
| Leu-Val-Thr-Glu-Lys-Ser-His-Trp-Leu-Cys | 468 |
| Leu-Val-Thr-Glu-Lys-Ser-His-Trp-Leu-Gly-Cys | 469 |
| Leu-Ala-Thr-Glu-Lys-Ser-Arg-Trp-Ser-Pro | 470 |
| Cys-Leu-Ala-Thr-Glu-Lys-Ser-Arg-Trp-Ser-Pro | 471 |
| Leu-Ala-Thr-Glu-Lys-Ser-Arg-Trp-Ser-Pro-Cys | 472 |
| Leu-Leu-Thr-Glu-Lys-Ser-Arg-Trp-Ser-Pro | 473 |
| Cys-Leu-Leu-Thr-Glu-Lys-Ser-Arg-Trp-Ser-Pro | 474 |
| Leu-Leu-Thr-Glu-Lys-Ser-Arg-Trp-Ser-Pro-Cys | 475 |
| Leu-Val-Thr-Glu-Lys-Ser-Arg-Trp-Ser-Pro | 476 |
| Cys-Leu-Val-Thr-Glu-Lys-Ser-Arg-Trp-Ser-Pro | 477 |
| Leu-Val-Thr-Glu-Lys-Ser-Arg-Trp-Ser-Pro-Cys | 478 |
| Leu-Met-Thr-Glu-Lys-Ser-Arg-Trp-Ser-Pro | 479 |
| Cys-Leu-Met-Thr-Glu-Lys-Ser-Arg-Trp-Ser-Pro | 480 |
| Leu-Met-Thr-Glu-Lys-Ser-Arg-Trp-Ser-Pro-Cys | 481 |
| Leu-Gly-Thr-Glu-Lys-Ser-Arg-Trp-Ser-Pro | 482 |
| Cys-Leu-Gly-Thr-Glu-Lys-Ser-Arg-Trp-Ser-Pro | 483 |
| Leu-Gly-Thr-Glu-Lys-Ser-Arg-Trp-Ser-Pro-Cys | 484 |
| Leu-Ala-Thr-Glu-Lys-Ser-Arg-Trp-Leu-Pro | 485 |
| Cys-Leu-Ala-Thr-Glu-Lys-Ser-Arg-Trp-Leu-Pro | 486 |
| Leu-Ala-Thr-Glu-Lys-Ser-Arg-Trp-Leu-Pro-Cys | 487 |
| Leu-Ala-Thr-Glu-Lys-Ser-Arg-Trp-Val-Pro | 488 |
| Cys-Leu-Ala-Thr-Glu-Lys-Ser-Arg-Trp-Val-Pro | 489 |
| Leu-Ala-Thr-Glu-Lys-Ser-Arg-Trp-Val-Pro-Cys | 490 |
| Leu-Ala-Thr-Glu-Lys-Ser-Arg-Trp-Thr-Pro | 491 |

TABLE 1-continued

| Peptide | SEQ ID NO: |
|---|---|
| Cys-Leu-Ala-Thr-Glu-Lys-Ser-Arg-Trp-Thr-Pro | 492 |
| Leu-Ala-Thr-Glu-Lys-Ser-Arg-Trp-Thr-Pro-Cys | 493 |
| Leu-Leu-Thr-Glu-Lys-Ser-Arg-Trp-Val-Pro | 494 |
| Cys-Leu-Leu-Thr-Glu-Lys-Ser-Arg-Trp-Val-Pro | 495 |
| Leu-Leu-Thr-Glu-Lys-Ser-Arg-Trp-Val-Pro-Cys | 496 |
| Leu-Val-Thr-Glu-Lys-Ser-Arg-Trp-Leu-Pro | 497 |
| Cys-Leu-Val-Thr-Glu-Lys-Ser-Arg-Trp-Leu-Pro | 498 |
| Leu-Val-Thr-Glu-Lys-Ser-Arg-Trp-Leu-Pro-Cys | 499 |
| Leu-Ala-Thr-Glu-Lys-Ser-Arg-Trp-Ser-Ala | 500 |
| Cys-Leu-Ala-Thr-Glu-Lys-Ser-Arg-Trp-Ser-Ala | 501 |
| Leu-Ala-Thr-Glu-Lys-Ser-Arg-Trp-Ser-Ala-Cys | 502 |
| Leu-Leu-Thr-Glu-Lys-Ser-Arg-Trp-Ser-Ala | 503 |
| Cys-Leu-Leu-Thr-Glu-Lys-Ser-Arg-Trp-Ser-Ala | 504 |
| Leu-Leu-Thr-Glu-Lys-Ser-Arg-Trp-Ser-Ala-Cys | 505 |
| Leu-Val-Thr-Glu-Lys-Ser-Arg-Trp-Ser-Ala | 506 |
| Cys-Leu-Val-Thr-Glu-Lys-Ser-Arg-Trp-Ser-Ala | 507 |
| Leu-Val-Thr-Glu-Lys-Ser-Arg-Trp-Ser-Ala-Cys | 508 |
| Leu-Met-Thr-Glu-Lys-Ser-Arg-Trp-Ser-Ala | 509 |
| Cys-Leu-Met-Thr-Glu-Lys-Ser-Arg-Trp-Ser-Ala | 510 |
| Leu-Met-Thr-Glu-Lys-Ser-Arg-Trp-Ser-Ala-Cys | 511 |
| Leu-Gly-Thr-Glu-Lys-Ser-Arg-Trp-Ser-Ala | 512 |
| Cys-Leu-Gly-Thr-Glu-Lys-Ser-Arg-Trp-Ser-Ala | 513 |
| Leu-Gly-Thr-Glu-Lys-Ser-Arg-Trp-Ser-Ala-Cys | 514 |
| Leu-Ala-Thr-Glu-Lys-Ser-Arg-Trp-Leu-Ala | 515 |
| Cys-Leu-Ala-Thr-Glu-Lys-Ser-Arg-Trp-Leu-Ala | 516 |
| Leu-Ala-Thr-Glu-Lys-Ser-Arg-Trp-Leu-Ala-Cys | 517 |
| Leu-Ala-Thr-Glu-Lys-Ser-Arg-Trp-Val-Ala | 518 |
| Cys-Leu-Ala-Thr-Glu-Lys-Ser-Arg-Trp-Val-Ala | 519 |
| Leu-Ala-Thr-Glu-Lys-Ser-Arg-Trp-Val-Ala-Cys | 520 |
| Leu-Ala-Thr-Glu-Lys-Ser-Arg-Trp-Thr-Ala | 521 |
| Cys-Leu-Ala-Thr-Glu-Lys-Ser-Arg-Trp-Thr-Ala | 522 |
| Leu-Ala-Thr-Glu-Lys-Ser-Arg-Trp-Thr-Ala-Cys | 523 |
| Leu-Leu-Thr-Glu-Lys-Ser-Arg-Trp-Val-Ala | 524 |
| Cys-Leu-Leu-Thr-Glu-Lys-Ser-Arg-Trp-Val-Ala | 525 |
| Leu-Leu-Thr-Glu-Lys-Ser-Arg-Trp-Val-Ala-Cys | 526 |
| Leu-Val-Thr-Glu-Lys-Ser-Arg-Trp-Leu-Ala | 527 |
| Cys-Leu-Val-Thr-Glu-Lys-Ser-Arg-Trp-Leu-Ala | 528 |
| Leu-Val-Thr-Glu-Lys-Ser-Arg-Trp-Leu-Ala-Cys | 529 |

Thus peptides of the above formulae also encompass homologous or analogous modified sequences, wherein non-variable amino acids, except for the HLA anchors in amino acid positions AA2 and AA9, in the formula may be conservatively replaced individually by amino acid residues having similar characteristics. For example, the non-variable amino acid residues may be replaced by other amino acid residues bearing the same charge and/or similar side chain lengths. Similarly the non-variable naturally-occurring amino acids may be replaced by non-naturally occurring amino acid residues. In one embodiment, the T cell receptor binding residues are preferably those residues that are present in the naturally occurring BRAF protein. For compounds of the formulae above, an amino acid residue may be a naturally-occurring amino acids, meaning one of the twenty amino acids that occur in nature in L form, which include alanine, cysteine, aspartate, glutamate, phenylalanine, glycine, histidine, isoleucine, lysine, leucine, methionine, aspargine, proline, glutamine, arginine, serine, threonine, valine, tryptophan, and tyrosine, or any derivative thereof produced through a naturally-occurring biological process or pathway.

Also encompassed by the formulae above are non-naturally-occurring amino acids. This latter term is used herein to refer to an amino acid other than a naturally-occurring amino acid as defined above, which can be synthesized or "man-made", and including a derivative thereof, whether produced synthetically or via a biological process or pathway. Non-naturally occurring amino acids include, without limitation, D amino acids, amino acids containing unnaturally substituted side chains, e.g., an N-methylated amino acid, cyclic amino acids, diamino acids, B-amino acids, homo amino acids. In some embodiments, the non-naturally occurring amino acids used in the above formulae are only those that do not strain the binding formation by adding extra atoms to the peptide backbone, because backbone hydrogen bonding contact with the MHC is desirable for these peptides.

Non-naturally-occurring or unnatural amino acids may be characterized by novel backbone and side chain structures and are widely available from commercial reagent suppliers, such as Sigma-Aldrich (on the world-wide web at sigmaaldrich.com), on the world-wide web at Netchem.com, and other sites. See also a broad literature on such structures including, without limitation, Han S and Viola R E, Protein Pept. Lett. 2004 11(2):104-14; Ishida et al, Biopolymers 2004 76(1):69-82; Sasaki et al, Biol. Pharm. Bull. 2004 27(2):244-7; Pascal R et al, Meth. Enzymol. 2003 369:182-94; Yoder N C and Kumar K, Chem. Soc. Rev. 2002 31(6):335-41; and Ager D J, Curr. Opin. Drug Discov. Devel. 2002 5(6):892-905; L. Aurelio et al, 2002 Organic Letters, 4(21):3767-3769 and references cited therein, incorporated by reference herein.

Such non-naturally occurring amino acid(s) when employed in the compounds above are anticipated to make the compounds more resistant to degradation by mammalian enzymes in serum, saliva, stomach and intestines, and thus compounds that are composed of one or more such amino acids may confer upon the compound enhanced stability and bioavailability in vivo. A variety of methods for producing non-natural amino acids are known and may be selected by one of skill in the art.

For example, one class of non-naturally occurring amino acids are L amino acids that effect stereochemistry. Thus, in one embodiment of compounds, one or more of the amino acids in the peptide may be in L form, while others may be in D form. Another non-naturally occurring amino acid is an amino acid which is modified to contain a substitution on the alpha-carbon in the amino acid structure. For example the alpha-carbon may be substituted by a suitable hydrocarbon moiety, such as aminoisobutyrate. Still another class of non-naturally occurring amino acids is amino acids which are modified or mutated to extend their carbon chain length. For example, an amino acid with a single alpha-carbon chain, may be extended with at least one additional carbon, i.e., a beta-carbon, and so on. An additional modification to an amino acid is the insertion of a substituent on the nitrogen of the amino group. An example of this type of modification is an N-methyl amino acid. The addition of substituents on the alpha carbon or additional carbons or on the nitrogen of the amino acid molecule may occur in any of the amino acids of the formulae above.

Among useful substituents for creating the non-naturally occurring amino acids are a straight chain, branched, cyclic or heterocyclic $C_{1-12}$ alkyl group, and straight chain, branched, cyclic, or heterocyclic $C_{1-12}$ alkanoyl group. The amino acid may be also modified by the insertion of modifying sugars, imide groups and the like. Other amino acids are substituted in the ortho or meta position by a substituent such as H, OH, $CH_3$, halogen, $OCH_3$, $NH_2$, CH or $NO_2$.

A non-exclusive list of modified or non-naturally occurring amino acids for inclusion in compounds fitting the formulae above include amino acids modified by N-terminal acetylation, C-terminal amidation, formylation of the N-terminal methionine, gamma-carboxyglutamic acid hydroxylation of Asp, Asn, Pro or Lys residues in the compound, methylation of Lys or Arg, preferably; phosphorylation of Ser, Thr, Tyr, Asp or His in the compound, use of a pyrrolidone carboxylic acid, which is an N-terminal glutamate which has formed an internal cyclic lactam, sulfatation of Tyr, generally. Still other modifications of non-naturally occurring amino acids include use of or substitution with the following moieties: a 2-aminoadipic acid group, a 3-aminoadipic acid group, beta-Ala or beta-aminopropionic acid group, 2-aminobutryic acid, 4-aminobutyric acid, piperidinic acid, 6-aminocaproic acid, 2-aminoheptanoic acid, 2-aminoisobutryic acid, 3-aminoisobutyric acid, 2-aminopimelic acid, 2, 4 diaminobutyric acid, desmosine, 2,2'-diaminopimelic acid, 2,3-diaminopropionic acid, N-ethylglycine, N-ethylglycine, N-ethyl asparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, 6-N-methyllysine, norvaline, norleucine, and ornithine.

In another embodiment, peptides of the formulae described above may be organized in multimeric constructs or compositions, when either R1 or R2 are optional amino acids (e.g., Cys, -Gly-Ser-) or other amino acid or chemical compound spacers may be included at the N- or C-termini of the peptide for the purpose of linking two or more peptides together or linking a peptide to a second protein, peptide or carrier. Preferably, the spacer of R1 or R2 is a proteolytically sensitive spacer to permit cleavage of the epitope before it enters the cell compartment where it associates with MHC. The peptide may be prepared as a synthetic peptide coupled to a carrier protein. Alternatively, the selected peptides may be linked sequentially and expressed as a recombinantly produced protein or polypeptide. In one embodiment, multiple peptides are linked sequentially, with and without spacer amino acids therebetween, to form a larger recombinant protein. Alternatively, the recombinant protein may be fused in frame with a carrier protein or transporter protein, such as described herein.

In another embodiment, one or more of said peptides is a synthetic peptide fused to a carrier protein. Still alternatively multiple of the above-described peptides with or without flanking sequences, may be combined sequentially in a polypeptide. The peptides or this polypeptide may be coupled to the same carrier, or different peptides may be coupled individually as peptides to the same or a different carrier protein.

Suitable carrier proteins may enhance stability or delivery, improve the production, or change the activity spectrum of the peptide. As a few well-known examples, such carriers may be human albumin, keyhole limpet hemocyanin, polyethylene glycol, other biopolymers or other naturally or non-naturally occurring polymers. In one embodiment, the moiety is desirably a protein or other molecule which can enhance the stability of the peptide or enhance its penetration into the targeted cell. One of skill in the art can readily select an appropriate conjugation moiety. Still other proteins or peptides to which the $BRAF^{v600E}$ peptides described herein may be linked via the spacer include keyhole limpet hemocyanin or additional MHC molecules. Still other carriers include a live antigen-presenting cell, such as a dendritic cell, which presents the peptides described herein.

Still alternative carriers or peptide-carrier constructs utilize lipopeptides, and with the BRAF mutants peptides, form chimeric peptides, designed according to procedures described in, e.g., Weiguang Zeng et al, J. Immunol., 2002, 169: 4905-4912 and A. Vitiello et al, J. Clin. Invest., 1995, 95:341-349, incorporated herein by reference.

In yet another embodiment, the peptides may be in the form of a multiple antigenic peptide ("MAP"). Such a construct may be designed employing the MAP system described by Tam, Proc. Natl. Acad. Sci. USA, 1988 85:5409-5413. This system makes use of a core matrix of lysine residues onto which multiple copies of the same peptide are synthesized as described [see, e.g., D. Posnett et al., J. Biol. Chem., 1988 263(4):1719-1725]. Each MAP contains multiple copies of one or more of the peptides described herein. One embodiment of a MAP contains at least three, and preferably four or more peptides. One preferred embodiment contains a β-alanine substituent on the poly-lysine core.

In yet another embodiment, a multimeric construct involves BRAY peptide-HLA tetrameric constructs. Such constructs are comprised of four of the same or different BRAF peptides bound to fluorochrome-conjugated HLA molecules. Such constructs can be used to detect T cells reacting to the BRAF peptides. Such tetrameric constructs may be prepared employing peptides described herein, fluorochromes such as FITC or phycoerthrin, among other known fluorochromes, by conventional techniques, such as described in J. D. Altman et al, Science, 1996; 280(5371):94-6; and M. V. Maus et al, Clin Immunol., 2003; 106(1):16-22, among others known to those of skill in the art.

One of skill in the art may readily make any number of multimeric constructs from the peptides of the formulae described herein with resort to only conventional skills and knowledge in light of this specification. All such multimeric compositions and constructs are intended to be included.

Such peptides and multimeric compositions may be produced synthetically or recombinantly by conventional methods. Specific embodiments of peptides are disclosed in detail in Table 1 above and the Examples below. Preferably, the peptides are prepared conventionally by known chemical synthesis techniques. Among such preferred techniques known to one of skill in the art are included the synthetic methods described by Merrifield, J. Amer. Chem. Soc., 1963 85:2149-2154 or as detailed in Example 1.

The modified compounds specifically identified herein and others within the teachings of this specification can all be readily tested for the required biological function, e.g., in mammalian cells in vitro and in vivo. The resulting peptide or multimeric construct is screened for biological activity and/or metabolic stability by in vitro and in vivo assays, such as those described in the examples and in the art. These peptides generally have "significant" metabolic stability in mammalian serum, i.e., the peptides are stable for at least 2 hours in serum. More preferred peptides are stable for at least 4 hours in serum. Still more preferred peptides are stable in serum for greater than 8 hours.

B. Nucleic Acid Sequences

A related embodiment is a nucleic acid sequence or sequences that encode one or more of the peptide compounds or constructs described herein. Such nucleic acid sequences may be generated by conventional techniques and useful in prophylactic, diagnostic, and therapeutic compositions and methods designed for delivery of the nucleic acid in vivo and expression of the peptide in vivo.

Nucleic acid sequences encoding the peptides or multimeric compositions described herein may be prepared by known recombinant DNA techniques and used to clone and express the peptides within a host microorganism or cell.

Alternatively, such nucleic acid sequences encoding these peptides may be delivered as nucleic acid constructs to a subject, e.g., as naked DNA or other DNA vaccine forms. For example, a suitable plasmid may be constructed containing a nucleic acid sequence encoding the selected mutant BRAF peptide under the control of regulatory sequences directing expression thereof in a mammalian or vertebrate cell. The components of the plasmid itself are conventional.

Non-viral, plasmid vectors useful contain isolated and purified DNA sequences comprising DNA sequences that encode the selected mutant BRAF peptide. The DNA molecule may be derived from viral or non-viral, e.g., bacterial species that have been designed to encode an exogenous or heterologous nucleic acid sequence. Such plasmids or vectors can include sequences from viruses or phages. A variety of non-viral vectors are known in the art and may include, without limitation, plasmids, bacterial vectors, bacteriophage vectors, "naked" DNA and DNA condensed with cationic lipids or polymers.

Examples of bacterial vectors include, but are not limited to, sequences derived from *bacille Calmette Guérin* (BCG), *Salmonella, Shigella, E. coli,* and *Listeria*, among others. Suitable plasmid vectors include, for example, pBR322, pBR325, pACYC177, pACYC184, pUC8, pUC9, pUC18, pUC19, pLG339, pR290, pK37, pKC101, pAC105, pVA51, pKH47, pUB110, pMB9, pBR325, Col E1, pSC101, pBR313, pML21, RSF2124, pCR1, RP4, pBAD18, and pBR328.

Examples of suitable inducible *Escherichia coli* expression vectors include pTrc (Amann et al., 1988 *Gene,* 69:301-315), the arabinose expression vectors (e.g., pBAD18, Guzman et al, 1995 *J. Bacteriol.,* 177:4121-4130), and pETIId (Studier et al., 1990 *Methods in Enzymology,* 185:60-89). Target gene expression from the pTrc vector relies on host RNA polymerase transcription from a hybrid trp-lac fusion promoter. Target gene expression from the pETIId vector relies on transcription from a T7 gn10-lac fusion promoter mediated by a coexpressed viral RNA polymerase T7 gn 1. This viral polymerase is supplied by host strains BL21 (DE3) or HMS I 74(DE3) from a resident prophage harboring a T7 gn1 gene under the transcriptional control of the lacUV5 promoter. The pBAD system relies on the inducible arabinose promoter that is regulated by the araC gene. The promoter is induced in the presence of arabinose The promoter and other regulatory sequences that drive expression of the peptide in the desired mammalian or vertebrate host may similarly be selected from a wide list of promoters known to be useful for that purpose. A variety of such promoters are disclosed below. In one embodiment of a DNA plasmid composition, useful promoters are the human cytomegalovirus (HCMV) promoter/enhancer (described in, e.g., U.S. Pat. Nos. 5,158,062 and 5,385,839, incorporated herein by reference) and the SCMV promoter enhancer.

Additional regulatory sequences for inclusion in a nucleic acid sequence, molecule or vector include, without limitation, an enhancer sequence, a polyadenylation sequence, a splice donor sequence and a splice acceptor sequence, a site for transcription initiation and termination positioned at the beginning and end, respectively, of the polypeptide to be translated, a ribosome binding site for translation in the transcribed region, an epitope tag, a nuclear localization sequence, an IRES element, a Goldberg-Hogness "TATA" element, a restriction enzyme cleavage site, a selectable marker and the like. Enhancer sequences include, e.g., the 72 by tandem repeat of SV40 DNA or the retroviral long terminal repeats or LTRs, etc. and are employed to increase transcriptional efficiency.

These other components useful in DNA plasmids, including, e.g., origins of replication, polyadenylation sequences (e.g., BGH polyA, SV40 polyA), drug resistance markers (e.g., kanamycin resistance), and the like may also be selected from among widely known sequences. Selection of promoters and other common vector elements are conventional and many such sequences are available with which to design the plasmids useful. See, e.g., Sambrook et al, *Molecular Cloning. A Laboratory Manual*, Cold Spring Harbor Laboratory, New York, (1989) and references cited therein at, for example, pages 3.18-3.26 and 16.17-16.27 and Ausubel et al., *Current Protocols in Molecular Biology*, John Wiley & Sons, New York (1989). All components of the nucleic acid sequences or molecules useful may be readily selected by one of skill in the art from among known materials in the art and available from the pharmaceutical industry. Selection of plasmid components and regulatory sequences are not considered a limitation.

Examples of suitable DNA plasmid constructs for use in nucleic acid compositions, for example, are described in detail in the following patent publications, which are incorporated by reference herein for such disclosures, e.g., International Patent Publication Nos. WO98/17799, WO99/43839 and WO98/17799; and U.S. Pat. Nos. 5,593,972; 5,817,637; 5,830,876; and 5,891,505, among others.

In yet another embodiment, the nucleic acid sequences or molecules encoding the BRAF mutant peptides described herein may be transduced into an antigen-presenting cell, e.g., a dendritic cell.

C. Antibodies

Also included is an isolated antibody that specifically binds a $BRAF^{V600E}$ peptide, compound or construct described herein. As used herein, the term "antibody" refers to an intact immunoglobulin having two light and two heavy chains. Thus a single isolated antibody or fragment may be a high affinity polyclonal antibody, a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, an Fv construct, a Fab construct, an Fc construct, a light chain variable or complementarity determining region (CDR) sequence, etc. Such antibodies or fragments may be generated synthetically or recombinantly, using now conventional techniques.

For example, a recombinant antibody or fragment described herein must contain variable regions that are capable of mediating binding to the $BRAF^{V600E}$ peptide. However, the constant regions can be altered by now conventional means. For example, the variable region of a selected anti-$BRAF^{V600E}$ antibody may be inserted into a constant region backbone, such as a human IgG1 backbone. Thus the resulting antibody may be a chimeric antibody containing human light chain variable regions associated with heavy chains from human or non-human sources, e.g., monkeys, etc., or a humanized antibody, using human IgG antibody backbones, or an antibody fragment. Selection of a suitable antibody backbone and insertion of the antibody variable sequences are within the skill of the art, provided with this specification and the conventional teachings of immunology.

D. Pharmaceutical Compositions and Methods of Treatment

The peptide and peptide compounds, antibody compositions or nucleic acid compositions described herein are designed to treat or prevent the development or progression of certain melanomas in mammalian subjects, e.g., humans. At least one, or alternatively, several of the peptides or other constructs may be formulated into a pharmaceutical composition with a pharmaceutically acceptable carrier, adjuvant, diluent, other optional components, or some combination thereof. For use in such compositions, the selected peptide may be produced preferably synthetically, but also recombinantly, as disclosed above. Similarly the antibodies or fragments may be produced as described above.

1. Peptide Compositions

The compounds may be employed in pharmaceutical compositions individually or in combination. Alternatively, for the purposes of enhancing pharmacokinetics or bioavailability, one or more peptides may be fused or conjugated to other moieties as described above. Any number of single peptides or multimeric constructs may be mixed together to form a single composition.

Similarly the peptide compounds may be coupled to penetration enhancer or transporter compounds to enhance transport of the compound into the cell. Proper transport and localization is demonstrated by a variety of detection methods such as, for example, fluorescence microscopy, confocal microscopy, electron microscopy, autoradiography, or immunohistochemistry.

It should also be added that other methods that have also been employed for delivery of proteins, may be useful. Such methods of protein delivery into a cell include scrape loading, calcium phosphate precipitates, liposomes, electroporation, membrane fusion with liposomes, high velocity bombardment with peptide-coated microprojectiles, incubation with calcium-phosphate-peptide precipitate, DEAE-dextran mediated transfection, and direct micro-injection into single cells. Chemical addition of a lipopeptide (P. Hoffmann et al., Immunobiol., 1988 177, pp. 158-70) or a basic polymer such as polylysine or polyarginine (W.-C. Chen et al., Proc. Natl. Acad. Sci. USA, 1978 75, pp. 1872-76). Folic acid has been used as a transport moiety (C. P. Leamon and Low, Proc. Natl. Acad. Sci. USA, 1991 88, pp. 5572-76). *Pseudomonas* exotoxin has also been used as a transport moiety (T. I. Prior et al., Cell, 1991 64, pp. 1017-23).

Such methods may be substituted for the peptide/protein transport moiety, if desirable.

As pharmaceutical compositions, the compounds can be utilized by themselves or as functionally effective derivatives. These compounds are admixed with a pharmaceutically acceptable vehicle or carrier suitable for administration as a protein composition. These peptides may be combined in a single pharmaceutical preparation for administration.

Suitable pharmaceutically acceptable carriers for use in a pharmaceutical proteinaceous composition are well known to those of skill in the art and include carriers that enhance stability and carriers that enhance immunogenicity. Such carriers include, for example, water, saline, buffered saline, alcohols, gum Arabic, vegetable oils, benzyl alcohols, polyethylene glycols, gelatin, carbohydrates, such as lactose, amylase or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, liposomes, oil in water emulsions and others. The compositions may further include a detergent to make the peptide more bioavailable, e.g., octylglucoside. The selection of the carrier or detergent is not a limitation.

The peptide compounds are also useful in the form of a salt with an acid. The compounds have at least one amino/amine groups which can form salts. Where two or more amino groups are present in the compound, a formulation of mixed salts can be prepared. Acids which can be used preferably include compatible inorganic acids such as hydrochloric and organic acids (or salts thereof) more preferably those occurring in living organisms, including but not limited to oxalic acid, glucuronic acid, pyruvic acid, lactic acid, citric acid, isocitric acid-ketoglutaric acid, succinic acid, malic acid, and oxaloacetic acid. In the preferred case of an aqueous solution, the desired anion can be added either as the free acid, or a salt, preferably one which is highly soluble in water, for example the sodium or potassium salts, but also the lithium, magnesium, calcium or ammonium salts. Moreover, these salts can be used either in anhydrous or hydrated forms. For example citric acid can be used as the anhydrous free acid, the monohydrate free acid, the anhydrous trisodium salt, or the dihydrate trisodium salt. These salts can be prepared by the methods described in International Patent Publication No. WO 96/02269.

Alternatively, the pharmaceutical compositions contain sequences which express the peptide or proteins described herein in the host cell, which peptides are then secreted from the host cells.

Suitable vehicles for direct DNA, plasmid nucleic acid, or recombinant vector administration include, without limitation, saline, sucrose, protamine, polybrene, polylysine, polycations, proteins, or spermidine, etc. [See e.g, International Patent Publication No. WO94/01139].

The pharmaceutical compositions may also be formulated to suit a selected route of administration, and may contain ingredients specific to the route of administration [see, e.g., Remington: The Science and Practice of Pharmacy, Vol. 2, 19$^{th}$ edition (1995)]. A non-exclusive list of auxiliary agents are lubricants, preservatives, stabilizers, wetting agents, emulsifiers, salts for influencing osmotic pressure, buffers, coloring, flavoring and/or aromatic substances and the like that do not deleteriously react with the active compounds. The preparation of these pharmaceutically acceptable compositions, from the above-described components, having appropriate pH isotonicity, stability and other conventional characteristics is within the skill of the art.

Preferably, the peptide compounds are administered with suitable adjuvants. An adjuvant is a substance that enhances the immune response when administered together with an immunogen or antigen. A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms), the interferons-α, β and γ, granulocyte-macrophage colony stimulating factor (see, e.g., U.S. Pat. No. 5,078,996 and ATCC Accession Number 39900), macrophage colony stimulating factor, granulocyte colony stimulating factor, GSF, and the tumor necrosis factors α and β. Still other adjuvants useful include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, incorporated herein by reference.

Suitable adjuvants include, without limitation, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form or as a stable emulsion.

Still other adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed *Bordetella*, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants are cholera toxins and mutants thereof, e.g., as described in International Patent Publication Nos. WO 02/098368 and WO 02/098369.

Adjuvants also include Freund's complete adjuvant and Montanide ISA 51 (Seppie, Paris, France).

A method of treating or preventing the development of a melanoma involves administering to a mammalian subject, preferably a human, an effective amount of a pharmaceutical composition described above. This method is useful to generate or activate T cells useful in attacking cancer cells. See, for example, the methods described in U.S. Published Patent Application No. US 2005/0119185, incorporated by reference herein. The method is useful in the treatment of melanomas to induce an MHC class I, HLA-A2 restricted CTL response by the patient against the cancer. A pharmaceutical composition as described above may be administered by any appropriate route, such as subcutaneous injection. Still other routes of administration include routes which transmits the peptide directly into the blood, e.g., intravenous injection. Other routes of administration include, without limitation, oral, intradermal, transdermal, intraperitoneal, intramuscular, intrathecal, mucosal (e.g., intranasal), and by inhalation.

The amount of the protein, peptide or nucleic acid sequences present in each effective dose is selected with regard to consideration to the half-life of the compound, the identity and/or stage of the melanoma, the patient's age, weight, sex, general physical condition and the like. The amount of active component required to induce an effective CTL response against the melanoma cells without significant adverse side effects varies depending upon the pharmaceutical composition employed and the optional presence of other components. Generally, for the compositions containing protein/peptide, or fusion protein, each dose will comprise between about 5 µg peptide/kg patient body weight to about 10 mg/kg. Generally, a useful therapeutic dosage is between 1 to 5 mg peptide/kg body weight. Another embodiment of a useful dosage may be about 500 µg/kg of peptide. Other dosage ranges may also be contemplated by one of skill in the art. For example, dosages of the peptides may be similar to the dosages discussed for other peptide cancer therapeutics.

Initial doses of a composition may be optionally followed by repeated administration for a duration selected by the attending physician. Dosage frequency may also depend upon the factors identified above, and may range from 1 to 6 doses per day for a duration of about 3 days to a maximum of no more than about 1 week. The compositions may also be administered as a continuous infusion for about 3-5 days, the specific dosage of the infusion depending upon the half-life of the compound. The compounds may also be incorporated into chemotherapy protocols, involving repetitive cycles of dosing. Selection of the appropriate dosing method would be made by the attending physician.

In another embodiment, vaccine compositions are provided for preventing the development of melanoma in a mammalian subject containing a compound as described herein and a pharmaceutically acceptable carrier. In other embodiments, the composition contains several compounds described herein. In a further embodiment, the vaccine contains two compounds as described herein. In still a further embodiment, the vaccine contains the compounds on SEQ ID NO: 8 and SEQ ID NO: 9. In still other embodiments, the vaccine contains three, four, five, six, seven, eight, nine, or ten compounds described herein. In a further embodiment, the composition also contains an adjuvant. Still other embodiments utilize multiple adjuvants. Still other vaccine compositions containing other components as described above or known to those of skill in the art of vaccine formulation are provided.

2. Antibody Compositions

Thus, another aspect is a pharmaceutical composition useful for the treatment of melanoma that contains an antibody or fragment that specifically binds a peptide described herein, and a pharmaceutically acceptable carrier. Such a pharmaceutical composition may preferably contain a single anti-BRAF$^{V600E}$ antibody or fragment. Additional embodiments of pharmaceutical compositions may contain two or more different anti-BRAF$^{V600E}$ antibodies or fragments, e.g., two or three antibodies that each bind different peptides. A variety of such combinations may be readily prepared by one of skill in the art given this disclosure.

As defined herein, the pharmaceutically acceptable carrier suitable for use in an immunogenic proteinaceous composition are well known to those of skill in the art. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents, inert gases and the like may also be provided in the pharmaceutical carriers. The selection of the carrier is not a limitation. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, 4$^{th}$ edit., eds. R. C. Rowe et al, APhA Publications, 2003, incorporated herein by reference.

Thus use of a anti-BRAF$^{V600E}$ antibody or fragment as described herein in the preparation of a medicament for treating or preventing the spread of melanoma in a human subject is provided.

The method of treating a patient prophylactically or therapeutically with antibody compositions described herein can involve chronically administering the composition. These anti-BRAF$^{V600E}$ antibody compositions are administered as passive immunotherapy, if desired. According to this method, the patient may be chronically treated with the antibody composition for a long treatment regimen. In the above-described methods, these compositions are administered by an appropriate route, e.g., by the subcutaneous, oral, mucosal, intravenous, intraperitoneal, intramuscular, nasal, or inhalation routes. The presently preferred route of administration is subcutaneous, intravenous or intramuscular.

The amount of the anti-BRAF$^{V600E}$ antibody, with or without other antibodies or chemotherapeutic agents present in each dose is selected with regard to consideration of the patient's age, weight, sex, general physical condition and the like. The amount of antibody required to produce an exogenous effect in the patient without significant adverse side effects varies depending upon the pharmaceutical composition employed. In infected patients, generally, each dose will comprise between about 5 to 400 mg/mL injection of the anti-BRAF$^{V600E}$ antibody in a sterile solution. Another dosage is about 200 mg of the antibody. Still another dosage is about 100 mg of the antibody. Still another embodiment is a dosage of about 50 mg of the antibody. A more preferred dosage may be about 10 mg of the antibody.

The frequency of chronic administration may range from daily dosages to once or twice a week to once a month, and may depend upon the half-life of the antibody (e.g., about 7-21 days). However, the duration of chronic treatment for such infected patients is anticipated to be an indefinite, but prolonged period. Other dosage ranges may also be contemplated by one of skill in the art, particularly where administration of the antibody composition is in conjunction or sequential with other chemotherapeutic treatments.

E. Drug Screening and Development

The peptides and polynucleotide sequences described herein may also be used in the screening and development of chemical compounds, small molecules or proteins which mimic the structure or activity of the peptides, and thus have utility as therapeutic drugs for the treatment of melanoma. In one such embodiment, the peptides are employed in a suitable competitive assay method with test compounds to assess the ability of the test compound to bind the mutated BRAF peptides. The steps of such a competitive assay may be readily determined by one of skill in the art. As another example, an assay may be performed using an animal model or in vitro assay such as those described in the Examples below, or employing a MHC Class 1, HLA-A2-restricted melanoma cell lines known in the art.

The compounds described herein can be used to identify other molecules or analogs that bind to the same BRAF peptides. Identification of useful test compounds permit the screening and development of identification, e.g., the screening of combinatorial libraries, of non-peptide libraries which mimic the activity of a peptide compound, antibody or anti-idiotype. For example, one of the peptides described herein may be employed to screen a small non-peptide molecule library for compounds that bind using a high throughput in vitro assay. The candidate molecules are then tested in melanoma cell lines, such as described below in the Examples. The candidate small molecule may be further tested in mouse models of human melanoma or a melanoma human xenograft. Other animal models of melanoma can also be employed.

Other assays and techniques also exist for the identification and development of compounds and drugs which mimic the structure or activity of a peptide described herein. These include the use of phage display system for expressing the peptide(s), and the use of a culture of transfected *E. coli* or other microorganisms to produce the peptides for binding studies of potential binding compounds. See, for example, the techniques described in G. Cesarini, FEBS Letters, 1992 307(1):66-70; H. Gram et al, J. Immunol. Meth., 1993 161: 169-176; C. Summer et al, Proc. Natl. Acad. Sci., USA, 1992 89:3756-3760, incorporated by reference herein.

Other conventional drug screening techniques may be employed using the peptides described herein. As one example, a method for identifying compounds which specifically bind to a peptide can include simply the steps of contacting a selected peptide with a test compound to permit binding of the test compound to the peptide; and determining the amount of test compound, if any, which is bound to the peptide. Such a method may involve the incubation of the test compound and the peptide immobilized on a solid support.

Typically, the surface containing the immobilized ligand is permitted to come into contact with a solution containing the peptide and binding is measured using an appropriate detection system. Suitable detection systems include the streptavidin horseradish peroxidase conjugate, direct conjugation by a tag, e.g., fluorescein. Other systems are well known to those of skill in the art. The detection system used is not a limitation.

Another method of identifying compounds which specifically bind to the peptides described herein includes the steps of contacting the peptide, immobilized on a solid support with both a test compound and a proposed receptor for the peptide to permit binding of the receptor to the peptide; and determining the amount of the receptor which is bound to the peptide.

A compound which has structural similarity to the peptide may also be computationally evaluated and designed by means of a series of steps in which chemical entities or fragments are screened and selected for their ability to associate with the peptides described herein. One skilled in the art may use one of several methods to screen chemical entities or fragments for their ability to mimic the structure of these peptides and more particularly to identify the peptide structure that binds with the stereospecific receptor of the compounds specifically described herein. This process may begin by visual inspection of, for example, a three dimensional structure of the peptides on a computer screen. Selected fragments or chemical entities may then be positioned in a variety of orientations to determining structural similarities, or docked, within a putative binding site of the peptide.

Specialized computer programs that may also assist in the process of selecting fragments or chemical entities similar to the peptides, or entities which can interact with the peptides and thus mimic the receptor, include the GRID program available from Oxford University, Oxford, UK. (P. J. Goodford, J. Med. Chem., 1985 28:849-857); the MCSS program available from Molecular Simulations, Burlington, Mass. (A. Miranker and M. Karplus, Proteins: Structure, Function and Genetics, 1991 11:29-34); the AUTODOCK program available from Scripps Research Institute, La Jolla, Calif. (D. S. Goodsell and A. J. Olsen, Proteins: Structure, Function, and Genetics, 1990 8:195-202); and the DOCK program available from University of California, San Francisco, Calif. (I. D. Kuntz et al, J. Mol. Biol., 1982 161:269-288), and software such as Quanta and Sybyl, followed by energy minimization and molecular dynamics with standard molecular mechanics force fields, such as CHARMM and AMBER. Additional commercially available computer databases for small molecular compounds include Cambridge Structural Database, Fine Chemical Database, and CONCORD database (for a review see Rusinko, A., Chem. Des. Auto. News, 1993 8:44-47 (1993).

Once suitable chemical entities or fragments have been selected, they can be assembled into a single compound, or an agonist of the mutant BRAF protein that increases T cell production to eliminate the BRAF protein on the melanoma cell, or an antagonist of the wild-type BRAF protein. Assembly may proceed by visual inspection of the relationship of the fragments to each other on the three-dimensional image displayed on a computer screen in relation to the structure of the peptide. Useful programs to aid one of skill in the art in connecting the individual chemical entities or fragments include the CAVEAT program [P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc. 78, pp. 182-196 (1989)], which is available from the University of California, Berkeley, Calif.; 3D Database systems such as MACCS-3D database (MDL Information Systems, San Leandro, Calif.) (see, e.g., Y. C. Martin, J. Med. Chem., 1992 35:2145-2154); and the HOOK program, available from Molecular Simulations, Burlington, Mass.

Compounds that mimic a peptide described herein may be designed as a whole or "de novo" using methods such as the LUDI program (H.-J. Bohm, J. Comp. Aid. Molec. Design, 1992 6:61-78), available from Biosym Technologies, San Diego, Calif.; the LEGEND program (Y. Nishibata and A. Itai, Tetrahedron, 1991 47:8985), available from Molecular Simulations, Burlington, Mass.; and the LeapFrog program, available from Tripos Associates, St. Louis, Mo. Other molecular modeling techniques may also be employed. See, e.g., N. C. Cohen et al, J. Med. Chem., 1990 33:883-894. See also, M. A. Navia and M. A. Murcko, Current Opinions in Structural Biology, 1992 2:202-210. For example, where the structures of test compounds are known, a model of the test compound may be superimposed over the model of the peptide. Numerous methods and techniques are known in the art for performing this step, any of which may be used. See, e.g., P. S. Farmer, Drug Design, Ariens, E. J., ed., Vol. 10, pp 119-143 (Academic Press, New York, 1980); U.S. Pat. No. 5,331,573; U.S. Pat. No. 5,500,807; C. Verlinde, Structure, 1994 2:577-587; and I. D. Kuntz, Science, 1992 257:1078-1082. The model building techniques and computer evaluation systems described herein are not a limitation.

Thus, using these computer evaluation systems, a large number of compounds may be quickly and easily examined and expensive and lengthy biochemical testing avoided. Moreover, the need for actual synthesis of many compounds is effectively eliminated.

Once identified by the modeling techniques, the proposed new compound may be tested for bioactivity using standard techniques, such as the in vitro assay of the examples. Suitable assays for use herein include, but are not limited to, the assays shown below in the examples to detect the CTL inductive effect of the peptides described herein. However, other assay formats may be used and the assay formats are not a limitation.

F. Diagnostic Reagents, Kits and Assays

As an additional embodiment, the $BRAF^{V600E}$ peptides or antibodies or fragments are useful as diagnostic assay reagents, and may be used in association with a detectable label or label systems, or be immobilized on a substrate, or be associated with another agent that mediates immobilization. In one particular embodiment, the BRAF peptide—HLA tetramer constructs are useful as reagents to detect immune reactive cells, and thus monitor patients for disease progression or response to therapy. Still another embodiment includes diagnostic kits which may contain $BRAF^{V600E}$ a peptides, multimeric constructs, or antibodies or fragments described herein, or several different such reagents. A variety of such combinations may be readily prepared by one of skill in the art given this disclosure. Such diagnostic or assay kits may also contain other melanoma-relevant peptides, or antibodies.

Such reagents and kits containing them are useful for the measurement and detection of melanoma in patients. The antibodies or peptides may be immobilized on suitable substrates, e.g., bound to an avidin-coated solid support, e.g., plates, sticks, or beads. Of course, other binding agents known to those of skill in the diagnostic assay art may also be employed for the same purposes. Also provided in the kit are reagents which detect the binding of peptide or antibody to the melanoma cell. Such reagents include a non-human antibody, e.g., goat anti-human immunoglobulin, or the like. Other reagents include conventional diagnostic labels or label systems. For example, the antibodies or peptides may be labeled directly or indirectly, with e.g., radioactive compounds, radioisotopes, such as $^{32}P$, $^{125}I$, tecnhicium; fluorescent or chemiluminescent compounds, such as FITC, rhodamine or luciferin; and proteins such as biotin or enzymes and enzyme co-factors, such as alkaline phosphatase, beta-glactosidase or horseradish peroxidase; and/or molecular labels such as FLAG, etc. See, e.g., Chubet R G, Brizzard B L. 1996 Biotechniques 20(1):136-141; and Knappik A, Pluckthun A. 1994 Biotechniques 1994; 17(4):754-761. Other elements of the label systems include substrates useful for generating the signals upon interaction with the other components of the label system, e.g., a streptavidin and horseradish peroxidase system. Any method known in the art for separately conjugating the antibody to the detectable moiety may be employed, including those methods described by Hunter et al, 1962 Nature 133:945; Pain et al 1981 J. Immunol., Meth. 40:219 and other conventional texts.

Alternatively, the labels may be used apart from the antibodies. The kit thus also contains miscellaneous reagents and apparatus for reading labels, e.g., certain substrates that interact with an enzymatic label to produce a color signal, etc., apparatus for taking blood samples, as well as appropriate vials and other diagnostic assay components.

The antibodies may be employed in any known assay method, such as competitive binding assays, direct and indirect sandwich assays, and immunoprecipitation assays. See, e.g., Zola, Monoclonal Antibodies: A Manual of Techniques, pp 147-158 (CRC Press, Inc. 1987) and other conventional assay texts for a variety of assay protocols. As one embodiment, a kit for use in diagnosing melanoma in patients may contain one or more of the peptides, antibodies or fragments described herein, and one or more detectable labels or label systems for identifying binding of these peptides or antibodies. One of skill in the art may also readily select other conventional diagnostic components for this kit. Any conventional assay format employing the peptides or antibodies may be employed to determine the efficacy of therapeutic treatment, as well as original diagnosis of disease.

EXAMPLES

The following examples illustrate various aspects described herein. These examples do not limit the scope of this application which is defined by the appended claims.

The following examples demonstrate a positive correlation between $BRAF^{V600E}$ mutation status in melanoma lesions and immune responses to the mutated epitope. Thus, 3 of 5 patients with $BRAF^{V600E}$-positive lesions demonstrated lymphoproliferative responses to stimulation with $BRAF^{V600E}$, but not wtBRAF peptide. One patient with a $BRAF^{V600E}$-positive lesion demonstrated lymphoproliferative responses to stimulation with both $BRAF^{V600E}$ and wtBRAF peptides. The uncloned lymphocyte population may react with both mutated and wtBRAF epitopes or with wt epitopes only, although immunological tolerance of lymphocytes to wtBRAF sequences would be expected. Only 1 of the 5 patients with $BRAF^{V600E}$-positive lesions demonstrated absence of lymphoproliferative responses to stimulation with $BRAF^{V600E}$ or wtBRAF peptides. None of 4 patients with $BRAF^{V600E}$-negative lesions had a lymphoproliferative response to stimulation with $BRAF^{V600E}$ or wtBRAF peptide. In one patient (#3463), the primary lesion expressed $BRAF^{V600E}$ (Table 2) where as the metastatic lesion did not (not shown).

Lymphoproliferative responses to $BRAF^{V600E}$ peptide stimulation were positive at the time of metastasis occurrence. The lymphoproliferative response to $BRAF^{V600E}$ peptide stimulation of this patient most likely was elicited by expressed by the primary lesion. Thus, the loss of the $BRAF^{V600E}$ genotype during progression from primary to metastatic melanoma in patients with $BRAF^{V600E}$-specific T cell responses suggests an active immune selection of non-mutated melanoma clones by the tumor-bearing host.

Example 1

BRAF$^{V600E}$ Status of Melanoma Cells

BRAF mutation (BRAF$^{V600E}$) status was determined by PCR of genomic DNA obtained from fresh tumor (patients: 3457, 3463, 3495, 3502), or from formalin fixed, paraffin-embedded tissue blocks (patients: CS and RP) or from cultured tumor cell lines (patients: 35, 3445, 3451) of melanoma patients.

A. Patients

Nine HLA-A*0201 positive melanoma patients (1 with primary melanoma and 8 with metastatic disease, see Table 2) and 5 HLA-A*0201 positive normal healthy donors were included in this study. All human blood samples were obtained under informed consent using a protocol approved by the Institutional Review Boards of the Hospital of the University of Pennsylvania and the Wistar Institute.

B. Cell Lines

Melanoma cell lines WM35, WM278 and WM793 were established from three patients' primary melanomas (Satyamoorthy K, et al. Melanoma Res 1997; 7 Suppl 2:S35-42). WM3456 and WM3457 were established from patients' metastatic melanomas as described in the reference above. All melanoma cells were maintained in MCDB153-L15 medium (Sigma, St. Louis, Mo.) supplemented with 2% fetal bovine serum (FBS).

C. Detection of BRAF$^{V600E}$

DNA isolated from fresh or paraffin embedded tissue blocks or cell lines of melanoma patients was used for detection of BRAF$^{V600E}$ (Brose et al, cited above). Briefly, genomic DNA was screened for mutations using heteroduplex and sequence analysis. Primers spanning the mutation were used for the polymerase chain reaction (PCR) and sequence analysis of the PCR product confirmed the mutation or wt status. The primers described in Brose et al. were designed to amplify exon 15, and genomic DNA was used as template for detection of somatic changes. PCR reactions were performed using standard PCR conditions with fluorescence-labeled primers. Products were denatured followed by incubation at 68° C. for 1 hour to allow for reannealing and the generation of heteroduplexes. The samples were then analyzed by the ABI PRISM 3100 automated capillary sequencer under semidenaturing conditions using polymer provided by ABI and optimized run conditions. Data were captured using GeneScan to identify samples that produced a shift in peak migration relative to either the matched normal control from the same individual or a standard normal control, indicating the presence of a putative sequence variation. Amplicons, selected by the presence of a heteroduplex shift, were then sequenced directly in both the forward and reverse directions by the automated sequencer to confirm the presence of a mutation.

D. Results

Five of nine melanoma samples (including one cell line) were positive for BRAF$^{V600E}$ (Table 2).

All five samples also expressed wtBRAF. It is unclear whether in 3 of the 4 samples (3457, 3502, CS) and in the other exclusively wtBRAF-positive samples, wtBRAF is expressed by tumor cells or normal cells present in the tumor tissues. However, in 3 specimens (##35, 3445 and 3451), wtBRAF and BRAF$^{V600E}$ were detected in the tumor cells as these specimens represent patients' tumor cell lines. These results are consistent with earlier observations of the inventors (Davies, 2002 and Brose 2002, both cited above) and the observations of other investigators (Sharkey 2004, cited above; Dong J et al Cancer Res 2003; 63:3883-5; and Gorden A et al. Cancer Res 2003; 63:3955-7).

TABLE 2

Patients' HLA type and BRAF status

| Patient no. | Stage of melanoma | HLA type | BRAF status[a] |
|---|---|---|---|
| 35 | Primary | A*0201; B18; B51; C2; C1203; DRb1*0701; DR1602; DQb1 0303; DQb1 05; DRb4* 01: DRb5* 02 | V600E + wt |
| CS | Metastatic | A*0201; A29; B44; B50; Cw06; Cw160; DRb1 11; DRb1 13; DRb3*02; DQb1 03 | V600E + wt |
| 3457 | Metastatic | A*0201; A03; B18; B40; Cw03; Cw05; DRb1 03; DQb1 02 | V600E + wt |
| 3463 | Primary | A01; A*0201; B08; B15; Cw04; Cw07; DRb1 03; DRb1 12; DQb1 02; DQb1 03 | V600E + wt |
| 3502 | Metastatic | A*0201; A24; B07; Cw07; DRb1 0301; DRb1 11; DQb1 02; DQb1 03 | V600E + wt |
| RP | Metastatic | A*02, A31, B40, Cw02, Cw03, DRb1 1101, DRb1 1302, DQb1 03, DQb1 06 | Wt |
| 3445 | Metastatic | A*0201; A68; B14; B18 Cw08; Cw12; DRb1 0201; DRb1 | Wt |
| 3456 | Metastatic | A*0201; A03 B27; B40; Cw01; Cw02; DRb1 0103; DRb1 1101 | Wt |
| 3495 | Metastatic | A*0201; A31; B27; B44; Cw02; Cw05; DRb1 04; DRb1 13; DQb1 03; DQb1 06 | Wt |

Example 2

Identification of Putative HLA-A*0201 Anchor Residues in BRAF$^{V600E}$ Peptides MHC class I binding algorithm was used to analyze BRAF$^{V600E}$ amino acid (aa) fragment 582-623 for potential HLA-A*0201 binding residues. The MHC binding prediction scores in Table 3 were based on the database ("SYFPEITHI") developed by Rammensee et al. (found on the world-wide web at syfpeithi.de). Two putatively HLA-A*0201 binding peptides (residues: 597-605 (SEQ ID NO: 8) and 597-606 (SEQ ID NO: 9)) were identified (Table 3). Bold letters indicate HLA-A*0201 anchor residues.

Two algorithms predicting proteasome cleavage (PAProc and FRAGPREDICT) did not reveal any possible cleavage sites within the identified peptide fragments. Two wtBRAF peptides corresponding to the two BRAF$^{V600E}$ peptides and one control peptide with BRAF-unrelated sequence, but expressing HLA-A*0201 anchors are also shown in Table 3.

These BRAF$^{V600E}$ or wtBRAF peptides were synthesized, HPLC purified and encapsulated in poly (DL-lactide-co-glycolide) (PLG) microspheres (Ertl H C et al, Vaccine 1996; 14:879-85). These encapsulated peptides were used in the following lymphoproliferation assays.

TABLE 3

HLA-A*0201-binding peptides of BRAF$^{V600E}$ and human wtBRAF

| SEQ ID NO: | BRAF Residues | BRAF Mutation Status | Amino Acid Sequence | MHC Binding Prediction Score |
|---|---|---|---|---|
| 8 | 597-605 | V600E | LATEKSRWS | 8 |
| 9 | 597-606 | V600E | LATEKSRWSG | 9 |
| 530 | 597-605 | wt | LATVKSRWS | 6 |

TABLE 3-continued

HLA-A*0201-binding peptides of BRAF$^{V600E}$ and human wtBRAF

| SEQ ID NO: | BRAF Residues | Mutation Status | Amino Acid Sequence | MHC Binding Prediction Score |
|---|---|---|---|---|
| 531 | 597-606 | wt | LATVKSRWSG | 7 |
| 532 | Control peptide, EGF-R | Not applicable | KALEEKKGNY | 9 |

Example 3

In Vitro Lymphocyte Proliferative Response to Stimulation with BRAF$^{V600E}$ and wtBRAF Peptides Nine HLA-A*0201 positive melanoma patients and five HLA-A*0201 positive normal healthy donors were analyzed for their lymphoproliferative responses to stimulation with HLA-A*0201 binding BRAF$^{V600E}$ and wtBRAF peptides (FIG. 1).

A. T-Cell Proliferation Assay

This assay was performed as described (Somasundaram R., et al. J Immunol 1995; 155:3253-61). Briefly, peripheral blood mononuclear cells (PBMC) were isolated by Ficoll-Hypaque density gradient centrifugation of heparinized blood and cryopreserved. Adherent monocytes ($5 \times 10^4$ per well of a 96-well round-bottom microtiter plate; Corning, N.Y.) were pulsed for 8 h with BRAF$^{V600E}$, wtBRAF or control peptides (25 µg/ml) in PLG microspheres (1 µg/ml; see Table 3). All preparations were in RPMI 1640 with GlutaMAX™ medium (GIBCO-Invitrogen, Carlsbad, Calif.) supplemented with 10% heat inactivated human AB serum (Gemini Bioproducts, Calabasas, Calif.), 10 mM HEPES and $5 \times 10^{-5}$ M 2-β-mercaptoethanol (both from Sigma Chemical Co., St. Louis, Mo.). After the incubation, excess peptides were removed and the peptide-pulsed monocytes were co-cultured with PBMC ($10^5$ cells/well) in T cell medium (RPMI 1640 with GlutaMAX™, 10% human AB serum, 10 mM HEPES, $5 \times 10^{-5}$ M 2-β-mercaptoethanol, L-arginine [116 mg/l; GIBCO-Invitrogen] and L-asparagine [36 mg/l; GIBCO-Invitrogen]). Proliferative responses of the PBMC were determined on day 5 by [$^3$H]-thymidine (TdR) incorporation assay. All determinations were performed in triplicate.

B. Results

Four patients (##35, CS, 3457 and 3463) had significant lymphoproliferative responses to stimulation with BRAF$^{V600E}$ peptides. In one of the 4 patients (CS), the wtBRAF peptide also induced a low but statistically significant lymphoproliferative response. Similarly, lymphoproliferative responses have been observed in breast cancer patients following stimulation of the lymphocytes not only with mutated, but also wt peptides of epidermal growth factor receptor (EGF-R) (Purev E, et al. J Immunol 2004; 173:6472-80).

All 4 patients (## CS, 35, 3457 and 3463) with lymphoproliferative responses to BRAF$^{V600E}$ peptide stimulation expressed BRAF$^{V600E}$ on tumor cells. Lymphocytes of patient 3457 responded to stimulation with 9-mer, but not 10-mer BRAF$^{V600E}$ peptide. Thus, one amino acid difference has a profound effect on lymphocyte stimulation by BRAF$^{V600E}$ peptide, in agreement with the results reported by other investigators (Shih F F, Allen P M., Mol Immunol 2004; 40:1041-6). Patient 3502 showed no lymphoproliferative response to BRAF$^{V600E}$ peptide stimulation despite the presence of BRAF$^{V600E}$ mutation in tumor cells.

Example 4

CD Markers and Cytokine Secretion

A. Cytokine Measurements

Supernatants obtained from PBMC stimulated with peptide-pulsed monocytes after 2-4 days were tested for the presence of interferon (IFN)-γ and IL-4. All cytokine determinations were performed using ELISA kits (Endogen, Rockford, Ill.).

B. Phenotyping of Lymphocytes

Cultured lymphocytes were incubated with saturating concentrations (5 µg/ml) of fluoresceinated isothiocyanate (FITC) or phycoerythrin (PE)-labeled anti-CD4, -CD8 or -CD25 mAb in RPMI-1640 medium supplemented with 5% human AB serum for 1 hr at 4° C. Antibody binding was analyzed in a cytofluorograph. Differences between experimental and control values were analyzed for significance by Student's 2-sided t-test.

C. Generation of Anti-BRAF$^{V600E}$ CTL

Growing T cells from BRAF$^{V600E}$ peptide-stimulated lymphocytes were periodically restimulated in T-cell medium with BRAF$^{V600E}$ peptide and 20 U/ml of recombinant IL-2 (gift from Biological Resources Branch, NCI-Frederick Cancer Research and Development Center, Frederick, Md.). This process was repeated every 7 days until day 56 when lymphocytes were harvested and tested for cytolytic activity.

D. Cytotoxicity Assay

Labeled target cells (25 µCi of $^{51}$Cr, as Na$_2$CrO$_4$, per $2 \times 10^4$ cells) were mixed in 96-well round-bottom microtiter plates with effector cells at various effector-to-target ratios (E:T) and incubated at 37° C. for 6 hours (Somasundaram R, et al. Int J Cancer 2000; 85:253-9). Supernatants were harvested and tested for $^{51}$Cr release (experimental release). For maximal release, target cells were treated with 10N HCl. Spontaneous release of radioactivity by target cells was determined in the absence of effector cells. The percentage of cytotoxicity was determined by the following formula:

$$\% \text{ cytotoxicity} = \frac{\text{Experimental release} - \text{Spontaneous release}}{\text{Maximal release} - \text{Spontaneous release}} \times 100$$

E. Blocking of Lymphocyte Proliferative Response to BRAF$^{V600E}$ Peptide Stimulation Peptide-pulsed monocytes (proliferation assay) or tumor targets (CTL assay) were incubated with anti-HLA class I-specific monoclonal antibody (mAb) W6/32 (IgG$_{2a}$; 10 µg/ml), anti-HLA class II-specific mAb B33.1 (both obtained from Dr. B. Perussia, Thomas Jefferson University and Dr. G. Trinchieri, The Wistar Institute); or anti-HLA-B57/HLA-A2 mAb MA2.1 (IgG$_1$; 10 µg/ml) (Takahashi M, et al. Clin Cancer Res 1995; 1:1071-7; American Type Culture Collection, Manassas, Va.). Mouse IgG at similar concentration was used as control (Somasundaram R, et al. Int J Cancer 2000; 85:253-9). All incubations were performed for 1 hr at room temperature. For CTL assay, excess blocking antibody was removed from tumor cells and for proliferation assay excess antibody was left with monocytes in culture medium for the entire duration of the experiment. Following blocking, T cell proliferation or cytotoxicity assays were performed as described above.

F. Results

Proliferating lymphocytes from patients 35, 3457 and 3463 predominantly expressed the cytotoxic T cell marker CD8 (80%, 62% and 49% of the cells positive, respectively). Lymphocytes of patient CS could not be phenotyped because of lack of sufficient number of cells. Lymphocytes from all three patients stained positive for Granzyme B (using FITC-conjugated mAb GB11 to granzyme B and PE-conjugated mAb δG9 to perforin; BD Pharmingen, San Diego, Calif.).

Supernatants from lymphocytes which proliferated to stimulation with BRAF$^{V600E}$ peptide contained high amounts of IFN-γ (>300 pg/ml) but not IL-4 (<20 pg/ml). WtBRAF peptide did not induce IFN-γ release in any of the patients' lymphocytes. Patient CS could not be included in those studies, because sufficient number of lymphocytes was not available. This finding is consistent with the absence of lymphoproliferative responses to stimulation with wtBRAF (see FIG. 1).

Figures 2A, 2B, 2C:
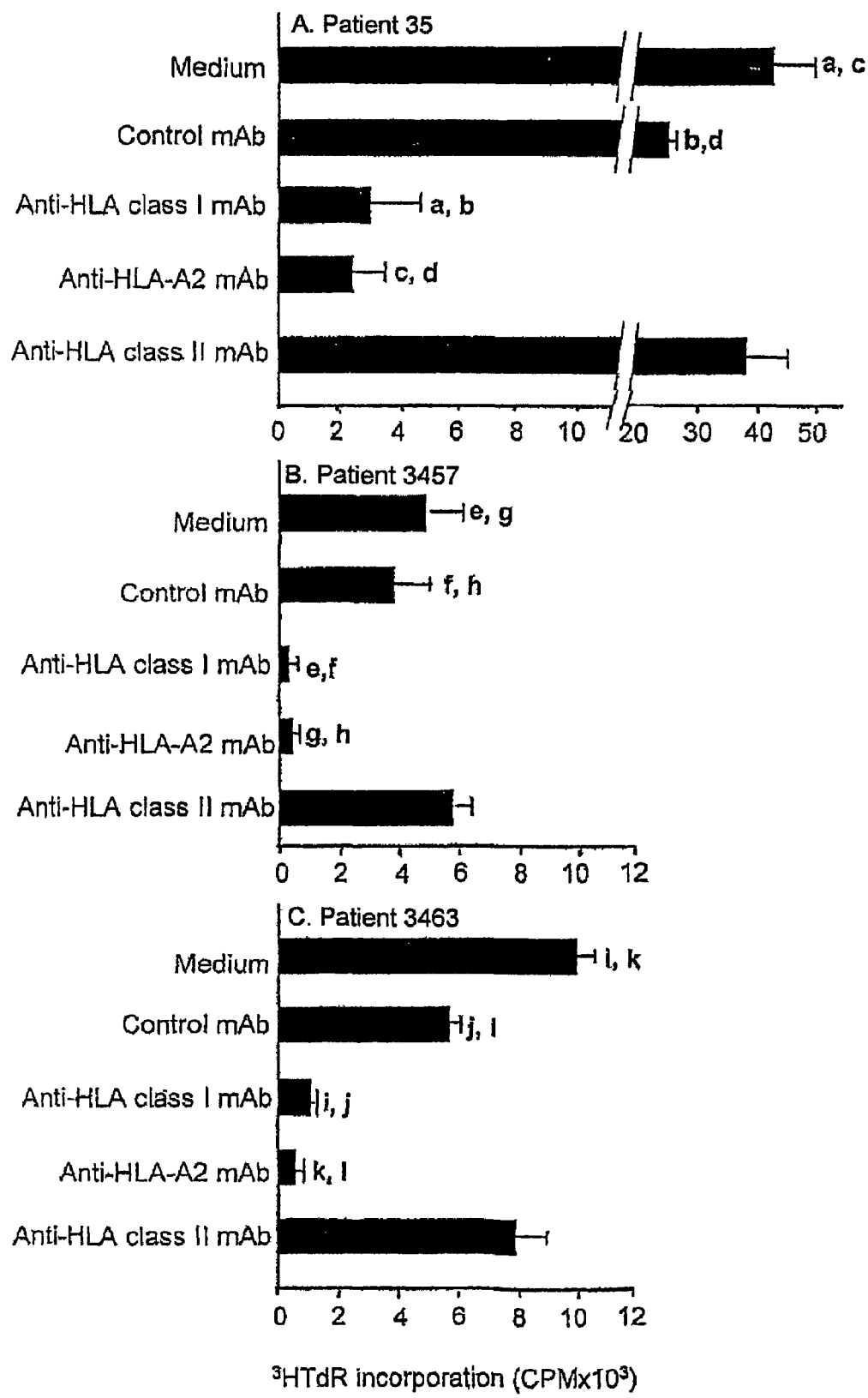
FIG. 2A is a bar graph showing inhibition of lymphoproliferative responses in Patient 35 to $BRAF^{V600E}$ peptide stimulation by anti-HLA class I and anti-HLA-A2 antibodies. Monocytes were pulsed with peptides as described in FIG. 1A and Table 3. At the end of incubation, excess peptides were removed and the peptide-pulsed monocytes were incubated with anti-HLA class I, anti-HLA class II or anti-HLA-A2 antibodies or control normal mouse immunoglobulin (all antibodies at 10 μg/ml) for 1 h at room temperature. At the end of incubation, monocytes were cultured with PBMC to determine lymphoproliferative responses as described in FIG. 1. Values with the same symbols (a-1) differ significantly from each other. Antibodies are described on the Y axis, and $^3$HTdR incorporation on the X axis.
FIG. 2B is a bar graph similar to that of FIG. 2A for Patient 3457.
FIG. 2C is a bar graph similar to that of FIG. 2A for Patient 3463.

Patients' (35, 3457 and 3463) lymphoproliferative responses to stimulation with BRAF$^{V600E}$ peptide were significantly (p<0.01) blocked by anti-HLA class I and anti-HLA-A2 (but not anti-HLA class antibodies, indicating that the proliferative responses are HLA-A2 restricted (FIG. 2).

Figures 3A, 3B, 3C, 3D, 3E:
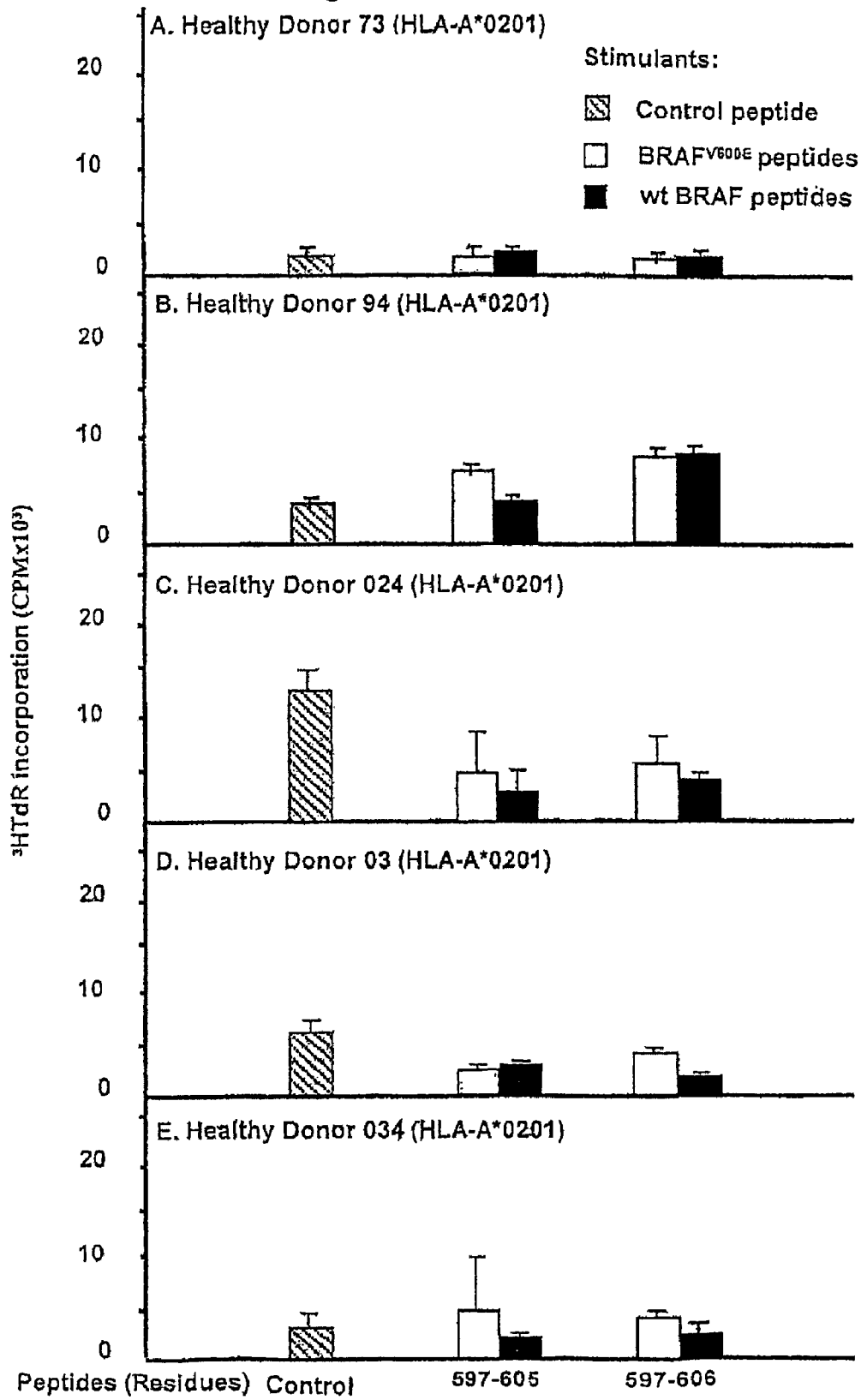
FIG. 3A is a bar graph showing absence of lymphoproliferative responses to $BRAF^{V600E}$ peptide stimulation in healthy donor 73. Proliferation assay was performed using HLA-A*0201 positive healthy donor lymphocytes as described in FIG. 1A. The same symbols are used for the stimulants and peptides. The Y axis shows $^3$HTdR incorporation; the X axis indicates the same peptides identified in FIG. 1 and Table 3.
FIG. 3B is a bar graph similar to that of FIG. 3A for Donor 94.
FIG. 3C is a bar graph similar to that of FIG. 3A for Donor 024.
FIG. 3D is a bar graph similar to that of FIG. 3A for Donor 03.
FIG. 3E is a bar graph similar to that of FIG. 3A for Donor 034.

None of the five HLA-A*0201 positive healthy donors had lymphoproliferative responses to stimulation with BRAF$^{V600E}$ or wt peptides (FIG. 3). In one donor (024), lymphocytes showed significant (p<0.05) proliferative responses to stimulation with control peptide (PLG-encapsulated EGF-R peptide) when compared to unstimulated T cells (FIG. 3), but there was no proliferative response to stimulation with BRAF$^{V600E}$ or wtBRAF peptides.

Figures 4A, 4B, 4C:
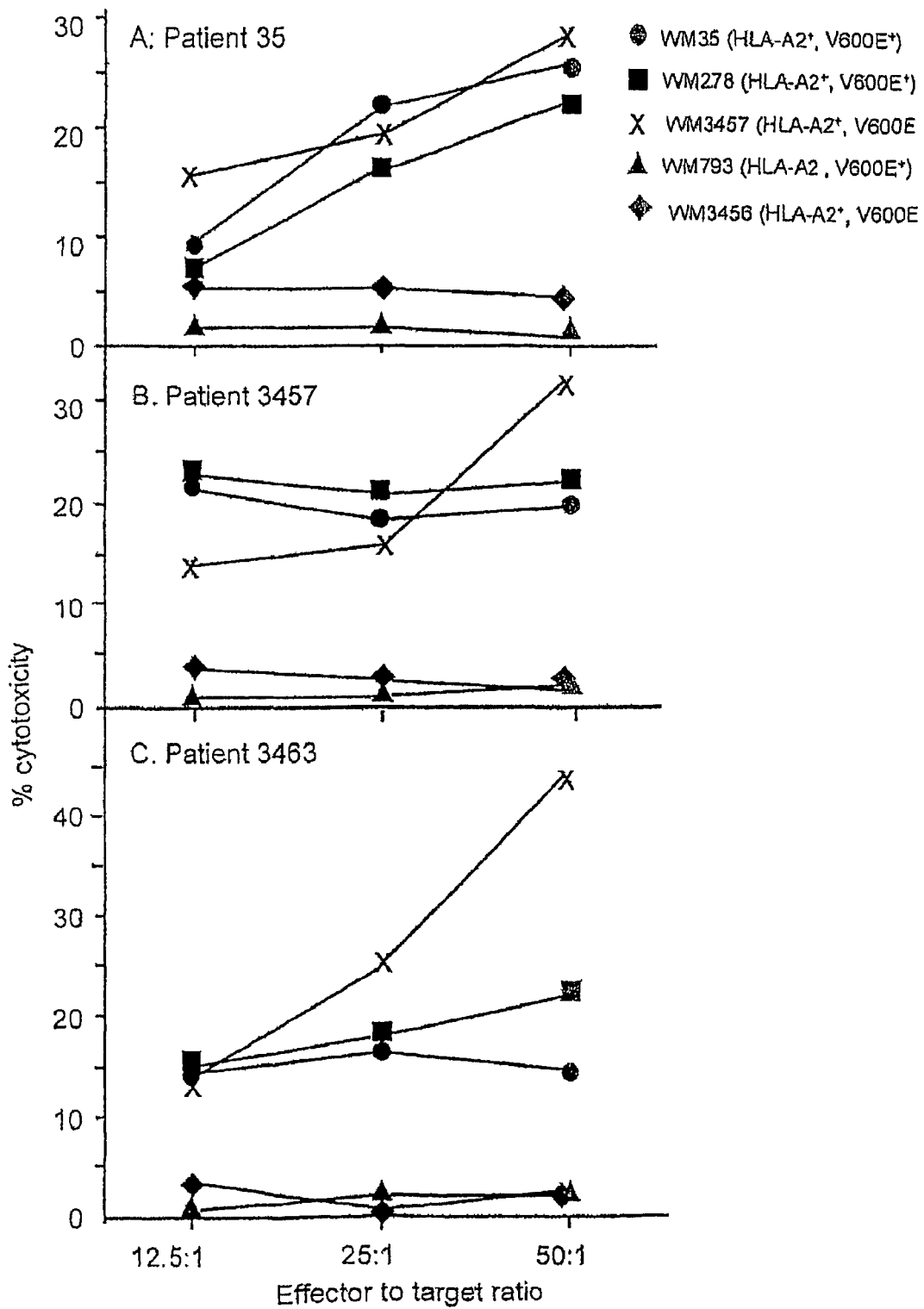
FIG. 4A is a graph showing cytotoxic activity of short-term T cell lines obtained from patient 35. Short-term (8 weeks) T cell lines were established by stimulating PBMCs of patient 35 with autologous adherent monocytes pulsed with $BRAF^{V600E}$ peptide (mutant peptide 597-606 (SEQ ID NO: 9); 25 μg/ml in PLG microspheres). After 7 days, growing lymphocyte cultures were harvested and restimulated with peptide and 20 U/ml of natural human IL-2. This process was repeated every 7 days until day 56, when lymphocytes were harvested and tested for cytotoxic activity against melanoma cells in a standard $^{51}$Cr-release assay. The melanoma cells were WM35 (●); WM278 (□); WM3457 (X); WM793 (▲); WM3456 (♦).
FIG. 4B is a graph showing cytotoxic activity of short-term T cell lines, as described in FIG. 4A, obtained from patient 3457, except that pulsing was performed with $BRAF^{V600E}$ peptide 597-605 (SEQ ID NO: 8) at 25 μg/ml in PLG microspheres.
FIG. 4C is a graph showing cytotoxic activity of short-term T cell lines obtained from patient 3463, as described in FIG. 4A.

Short-term T cell lines (8 weeks in culture) obtained from patients 35 (80% CD8$^+$), 3457 (62% CD8$^+$) and 3463 (49% CD8$^+$) were tested for cytotoxic activity against autologous or allogeneic WM35, WM278 and WM3457 melanoma cells (all cell lines are HLA-A2$^+$ and BRAF$^{V600E+}$), allogeneic WM3456 melanoma cells (HLA-A2$^+$ and BRAF$^{V600E-}$), and allogeneic WM793 melanoma cells (HLA-A2$^-$ and BRAF$^{V600E+}$). All three short-term T cell lines lysed WM35, WM278, and WM3457 cells, but not WM3456 or WM793 cells at E:T as low as 12.5 (FIG. 4). Cytotoxic activity of proliferating lymphocytes from patient CS could not be determined because of the lack of sufficient number of lymphocytes. Thus, CTL activity is dependent on both HLA-A2 and BRAF$^{V600E}$ expression by melanoma cells.

Figures 5A, 5B:
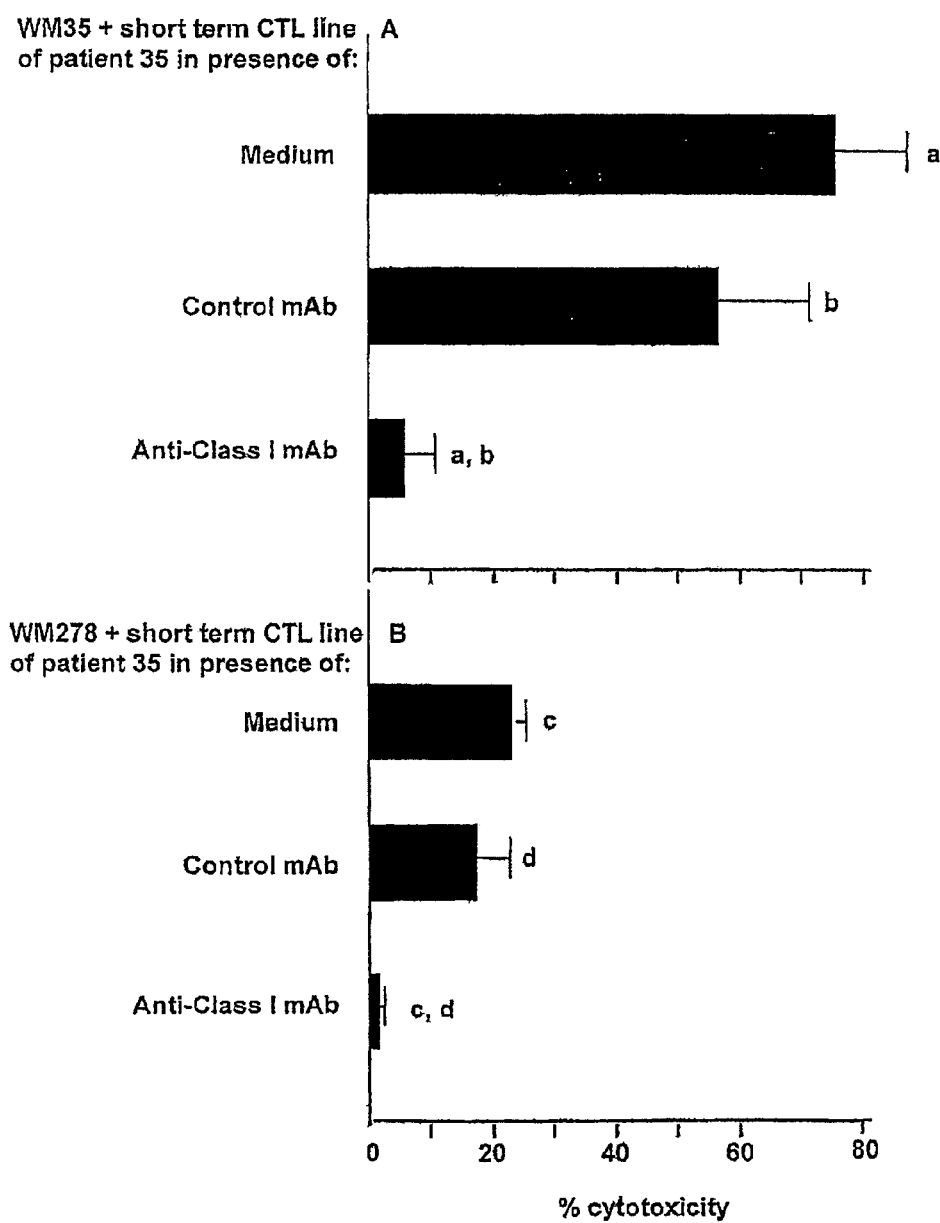
FIG. 5A is a bar graph showing inhibition of cytotoxic activity of short-term patient 35 T cell line (predominantly CD8$^+$) in the presence of anti-HLA class I mAb. Cytotoxic activity of short-term patient 35 T cell line was determined as described in FIG. 4A. WM35 tumor target was incubated with anti-HLA class I (W6/32) or control mouse immunoglobulin antibodies for 1 h at room temperature before the addition of T cells at E: T of 20.
FIG. 5B is a bar graph showing inhibition of cytotoxic activity of short-term patient 35 T cell line (predominantly CD8$^+$) in the presence of anti-HLA class I mAb. Cytotoxic activity of short-term patient 35 T cell line was determined as described in FIG. 4A. WM278 tumor target was incubated with anti-HLA class I (W6/32) or control mouse immunoglobulin antibodies for 1 h at room temperature before the addition of T cells at E: T of 20.

Cytotoxic activity of short-term CTL line from patient 35 against autologous WM35 melanoma cells (FIG. 5A) and allogeneic WM278 melanoma cells (HLA-A2$^+$BRAF$^{V600E+}$; FIG. 5B) was blocked in the presence of anti-HLA class I mAb, indicating that the T cells recognize antigen in an HLA-class I-restricted manner. Anti-HLA-A2 mAb, although able to block peptide-specific proliferation of the lymphocytes (see FIG. 2), was unable to block target cell lysis by the lymphocytes (results not shown), possibly due to the low affinity of the antibody.

Example 5

Antitumor Immunity Induced by Vaccine Compositions

In a typical antitumoral experiment, 10 mice are immunized with 4 doses (120 μg each, days 0, 14, 28, and 42) of a compound described herein using intramuscular injection and with Freund's complete adjuvant and Montanide ISA 51 (Seppie, Paris, France) as adjuvant. In one experiment, C57BL/6 female mice are used. As a control, another group of 10 mice, inoculated with PBS instead of vaccine, are used. On day 21, mice are challenged by subcutaneous injection of B16 murine melanoma cells (10$^3$) whose viability is confirmed in advance by dye exclusion. The mice are observed for 100 days and the size of external tumors developing at the inoculation site are measured twice per week.

Immunized mice are found to survive in significantly greater percentage as compared to non-immunized mice over both 5- and 100 day periods. Similarly, vaccinated mice are not found to have measurable median tumor volume (cm$^3$), i.e., 0, by day 32, as opposed to about 2.5 for non-immunized mice.

All publicly available documents and public databases and publicly available DNA and nucleic acid sequences cited within this specification are incorporated herein by reference. The claims are incorporated herein by reference. The sequence listing is incorporated herein by reference.

The invention claimed is:

1. A compound of the formula R1-Leu-AA2-AA3-Glu-AA5-AA6-AA7-Trp-AA 9-AA10-R2 (SEQ ID NO: 4), or a pharmaceutically acceptable salt thereof,
   wherein AA2 is an amino acid selected from the group consisting of a substituted or unsubstituted Ala, Leu, Met, Val, Pro and Gly;
   wherein AA3 is an amino acid selected from the group consisting of a substituted or unsubstituted Thr and Ser;
   wherein AA5 is an amino acid selected from the group consisting of a substituted or unsubstituted Lys, Arg and His;
   wherein AA6 is an amino acid selected from the group consisting of a substituted or unsubstituted Ser and Thr;
   wherein AA7 is an amino acid selected from the group consisting of a substituted or unsubstituted Arg, Lys, and His;
   wherein AA9 is an amino acid selected from the group consisting of a substituted or unsubstituted Thr, Val, Leu and Ser;
   wherein AA10 is absent or is a substituted or unsubstituted Gly, Pro or Leu;
   wherein R1 is absent or a Cys for coupling to a second peptide or protein; and
   wherein R2 is absent or a Cys for coupling to a second peptide or protein.

2. The compound according to claim 1, wherein one or more of said amino acids in said formula are selected from the group consisting of a D-amino acid, an amino acid containing a substitution for the alpha-carbon in the amino acid structure, an amino acid containing a beta-carbon in its amino acid structure, an amide substituted amino acid, an amino acid substituted with a straight chain, branched, cyclic or heterocyclic $C_{1-12}$ alkyl group, a straight chain, branched, cyclic, or heterocyclic $C_{1-12}$ alkanoyl group.

3. The compound according to claim 1, wherein the isolated peptide is selected from the group consisting of R1-Leu-AA2-Thr-Glu-Lys-Ser-Arg-Trp-AA9-AA10-R2 (SEQ ID NO: 6), wherein AA2 is independently Ala, Leu or Val; wherein AA9 is independently Ser, Val or Leu; and wherein AA10 is independently Gly or absent.

4. The compound according to claim 3, which is selected from the group consisting of the isolated peptides:

(SEQ ID NO: 533)
R1-Leu-Ala-Thr-Glu-Lys-Ser-Arg-Trp-Ser-R2;

(SEQ ID NO: 534)
R1-Leu-Ala-Thr-Glu-Lys-Ser-Arg-Trp-Ser-Gly-R2;

(SEQ ID NO: 535)
R1-Leu-Ala-Thr-Glu-Lys-Ser-Arg-Trp-Val-R2;

(SEQ ID NO: 536)
R1-Leu-Ala-Thr-Glu-Lys-Ser-Arg-Trp-Val-Gly-R2;

(SEQ ID NO: 537)
R1-Leu-Ala-Thr-Glu-Lys-Ser-Arg-Trp-Leu-R2;

(SEQ ID NO: 538)
R1-Leu-Ala-Thr-Glu-Lys-Ser-Arg-Trp-Leu-Gly-R2;

(SEQ ID NO: 539)
R1-Leu-Leu-Thr-Glu-Lys-Ser-Arg-Trp-Ser-R2;

(SEQ ID NO: 540)
R1-Leu-Leu-Thr-Glu-Lys-Ser-Arg-Trp-Ser-Gly-R2;

(SEQ ID NO: 541)
R1-Leu-Leu-Thr-Glu-Lys-Ser-Arg-Trp-Val-R2;

(SEQ ID NO: 542)
R1-Leu-Leu-Thr-Glu-Lys-Ser-Arg-Trp-Val-Gly-R2;

(SEQ ID NO: 543)
R1-Leu-Leu-Thr-Glu-Lys-Ser-Arg-Trp-Leu-R2;

-continued

R1-Leu-Leu-Thr-Glu-Lys-Ser-Arg-Trp-Leu-Gly-R2;  (SEQ ID NO: 544)

R1-Leu-Val-Thr-Glu-Lys-Ser-Arg-Trp-Ser-R2;  (SEQ ID NO: 545)

R1-Leu-Val-Thr-Glu-Lys-Ser-Arg-Trp-Ser-Gly-R2;  (SEQ ID NO: 546)

R1-Leu-Val-Thr-Glu-Lys-Ser-Arg-Trp-Val-R2;  (SEQ ID NO: 547)

R1-Leu-Val-Thr-Glu-Lys-Ser-Arg-Trp-Val-Gly-R2;  (SEQ ID NO: 548)

R1-Leu-Val-Thr-Glu-Lys-Ser-Arg-Trp-Leu-R2;  (SEQ ID NO: 549)
and

R1-Leu-Val-Thr-Glu-Lys-Ser-Arg-Trp-Leu-Gly-R2.  (SEQ ID NO: 550)

5. The compound according to claim 1, wherein the isolated peptide is R1-Leu-Ala-Thr-Glu-Lys-Ser-Arg-Trp-Ser-R2(SEQ ID NO: 533).

6. The compound according to claim 1, wherein the isolated peptide is R1-Leu-Ala-Thr-Glu-Lys-Ser-Arg-Trp-Ser-Gly-R2(SEQ ID NO: 534).

7. The compound according to claim 1, wherein the isolated peptide is Leu-Ala-Thr-Glu-Lys-Ser-Arg-Trp-Ser (SEQ ID NO: 8).

8. The compound according to claim 1, wherein the isolated peptide is Leu-Ala-Thr-Glu-Lys-Ser-Arg-Trp-Ser-Gly (SEQ ID NO: 9).

9. The compound according to claim 1, where said R1 or R2 is Cys.

10. The compound according to claim 1, which is coupled to either the N- or C-termini to a second protein or peptide.

11. The compound according to claim 10, wherein said second protein is keyhole limpet hemocyanin.

12. A pharmaceutical composition comprising one or more of the compounds of claim 1 in a pharmaceutically acceptable carrier.

13. The composition according to claim 12, further comprising a liposome.

14. A composition for retarding the development of melanoma in a mammalian subject comprising a compound of claim 1 and a pharmaceutically acceptable carrier.

15. A method of treating or retarding or preventing the development of melanoma in a mammalian subject comprising administering to said subject a composition of claim 14.

16. The method according to claim 15, wherein said composition comprises one or more peptides, or multimeric peptide constructs containing peptides, wherein said peptides are selected from the group consisting of:

R1-Leu-Ala-Thr-Glu-Lys-Ser-Arg-Trp-Ser-R2;  (SEQ ID NO: 533)

R1-Leu-Ala-Thr-Glu-Lys-Ser-Arg-Trp-Ser-Gly-R2;  (SEQ ID NO: 534)

-continued

R1-Leu-Ala-Thr-Glu-Lys-Ser-Arg-Trp-Val-R2;  (SEQ ID NO: 535)

R1-Leu-Ala-Thr-Glu-Lys-Ser-Arg-Trp-Val-Gly-R2;  (SEQ ID NO: 536)

R1-Leu-Ala-Thr-Glu-Lys-Ser-Arg-Trp-Leu-R2;  (SEQ ID NO: 537)

R1-Leu-Ala-Thr-Glu-Lys-Ser-Arg-Trp-Leu-Gly-R2;  (SEQ ID NO: 538)

R1-Leu-Leu-Thr-Glu-Lys-Ser-Arg-Trp-Ser-R2;  (SEQ ID NO: 539)

R1-Leu-Leu-Thr-Glu-Lys-Ser-Arg-Trp-Ser-Gly-R2;  (SEQ ID NO: 540)

R1-Leu-Leu-Thr-Glu-Lys-Ser-Arg-Trp-Val-R2;  (SEQ ID NO: 541)

R1-Leu-Leu-Thr-Glu-Lys-Ser-Arg-Trp-Val-Gly-R2;  (SEQ ID NO: 542)

R1-Leu-Leu-Thr-Glu-Lys-Ser-Arg-Trp-Leu-R2;  (SEQ ID NO: 543)

R1-Leu-Leu-Thr-Glu-Lys-Ser-Arg-Trp-Leu-Gly-R2;  (SEQ ID NO: 544)

R1-Leu-Val-Thr-Glu-Lys-Ser-Arg-Trp-Ser-R2;  (SEQ ID NO: 545)

R1-Leu-Val-Thr-Glu-Lys-Ser-Arg-Trp-Ser-Gly-R2;  (SEQ ID NO: 546)

R1-Leu-Val-Thr-Glu-Lys-Ser-Arg-Trp-Val-R2;  (SEQ ID NO: 547)

R1-Leu-Val-Thr-Glu-Lys-Ser-Arg-Trp-Val-Gly-R2;  (SEQ ID NO: 548)

R1-Leu-Val-Thr-Glu-Lys-Ser-Arg-Trp-Leu-R2;  (SEQ ID NO: 549)
and

R1-Leu-Val-Thr-Glu-Lys-Ser-Arg-Trp-Leu-Gly-R2,  (SEQ ID NO: 550)

wherein R1 is absent or a Cys for coupling to a second peptide or protein; and
wherein R2 is absent or a spacer for coupling to a second peptide or protein.

17. An isolated antibody that specifically binds a compound of claim 1.

18. A method of diagnosing the progression of melanoma in a mammalian subject comprising analyzing a biological fluid of said subject with a composition comprising a compound of claim 1 or an antibody of claim 17.

19. A diagnostic reagent comprising a compound of claim 1.

20. The diagnostic reagent according to claim 19 comprising a multimeric construct comprising multiple said compounds.

* * * * *

UNITED STATES PATENT AND TRADEMARK OFFICE
CERTIFICATE OF CORRECTION

| | | |
|---|---|---|
| PATENT NO. | : 7,811,993 B2 | Page 1 of 1 |
| APPLICATION NO. | : 11/922467 | |
| DATED | : October 12, 2010 | |
| INVENTOR(S) | : Herlyn et al. | |

It is certified that error appears in the above-identified patent and that said Letters Patent is hereby corrected as shown below:

Col. 217, Claim 15, line 45, delete "or preventing";

Col. 218, Claim 18, line 52, delete "or an antibody of claim 17";

Col. 218, Add after Claim 20, line 57, CLAIM -- 21. A method of diagnosing the progression of melanoma in a mammalian subject comprising analyzing a biological fluid of said subject with a composition comprising an antibody of claim 17. --.

Signed and Sealed this
Fifteenth Day of March, 2011

David J. Kappos
*Director of the United States Patent and Trademark Office*

UNITED STATES PATENT AND TRADEMARK OFFICE
CERTIFICATE OF CORRECTION

PATENT NO. : 7,811,993 B2
APPLICATION NO. : 11/922467
DATED : October 12, 2010
INVENTOR(S) : Herlyn et al.

It is certified that error appears in the above-identified patent and that said Letters Patent is hereby corrected as shown below:

Delete the title page and substitute therefore the attached title page showing the corrected number of claims in patent.

Col. 217, Claim 15, line 45, delete "or preventing";

Col. 218, Claim 18, line 52, delete "or an antibody of claim 17";

Col. 218, Add after Claim 20, line 57, CLAIM -- 21. A method of diagnosing the progression of melanoma in a mammalian subject comprising analyzing a biological fluid of said subject with a composition comprising an antibody of claim 17. --.

This certificate supersedes the Certificate of Correction issued March 15, 2011.

Signed and Sealed this
Twenty-sixth Day of April, 2011

David J. Kappos
*Director of the United States Patent and Trademark Office*

(12) United States Patent
Herlyn et al.

(10) Patent No.: US 7,811,993 B2
(45) Date of Patent: Oct. 12, 2010

(54) METHODS AND COMPOSITIONS FOR TREATING MELANOMA

(75) Inventors: Dorothee Herlyn, Wynnewood, PA (US); Rajasekaran Somasundaram, West Chester, PA (US); Laszlo Otvos, Jr., Audubon, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 551 days.

(21) Appl. No.: 11/922,467

(22) PCT Filed: Jun. 28, 2006

(86) PCT No.: PCT/US2006/025324
§ 371 (c)(1),
(2), (4) Date: Dec. 18, 2007

(87) PCT Pub. No.: WO2007/002811
PCT Pub. Date: Jan. 4, 2007

(65) Prior Publication Data
US 2010/0203109 A1    Aug. 12, 2010

Related U.S. Application Data

(60) Provisional application No. 60/694,871, filed on Jun. 29, 2005.

(51) Int. Cl.
*A61K 38/00* (2006.01)
*C07K 7/00* (2006.01)

(52) U.S. Cl. ............ 514/14; 530/327; 530/328; 435/7.23; 435/7.1; 514/15

(58) Field of Classification Search ............ None
See application file for complete search history.

(56) References Cited

OTHER PUBLICATIONS

Purev E, et al., "Immune responses of breast cancer patients to mutated epidermal growth factor receptor (EGF-RvIII, ΔEGF-R, and de2-7 EGF-R)", J. Immunol. 173(10):6472-6480 (Nov. 2004).
Ruiz PJ, et al. "Idiotypic immunization induces immunity to mutated p53 and tumor rejection", Nat. Med., 4(6):710-712 (Jun. 1998).
Fenton RG, et al, "Induction of T-cell immunity against Ras oncoproteins by soluble protein or Ras-expressing *Escherichia coli*", J. Natl. Cancer. Inst., 87(24):1853-1861 (Dec. 1995).
Khleif SN, et al., "A phase 1 vaccine trial with peptides reflecting *ras* oncogene mutations of solid tumors", J. Immunother., 22(2):155-165 (Mar. 1999).
Moscatello DK, et al., "A naturally occurring mutant human epidermal growth factor receptor as a target for peptide vaccine immunotherapy of tumors", Cancer Res., 57:1419-1424 (Apr. 1997).
Pinilla-Ibarz J, et al., "CML vaccines as a paradigm of the specific immunotherapy of cancer", Blood Rev., 14:111-120 (Jun. 2000).
Van Denderen J, et al., "Antibody recognition of the tumor-specific *bcr-abl* joining region in chronic myeloid leukemia", J. Exp. Med., 169:87-98 (Jan. 1989).
Somasundaram R, et al, "Human Leukocyte Antigen-A2—Restricted CTL responses to Mutated BRAF Peptides in Melanoma Patients", Cancer Res., 66(6):3287-3293 (Mar. 2006).
Andersen MH et al., "Immunogenicity of constitutively active $^{V599E}$BRaf", Cancer Res., 64:5456-5460 (Aug. 2004).
Marincola FM, et al., "Analysis of expression of the melanoma-associated antigens MART-1 and gp100 in metastatic melanoma cell lines and in in situ *lesions*", J. Immunother., 19(3):192-205 (May 1996).
Scanlan MJ, et al., "Characterization of human colon cancer antigens recognized by autologous antibodies", Int. J. Cancer, 76:652-658 (Jan. 1998).
Baurain JF, et al., "High frequency of autologous anti-melanoma CTL directed against an antigen generated by a point mutation in a new helicase gene", J. Immunol., 164(11):6057-6066 (Jun. 2000).
Gambacorti-Passerini C, et al.. "Human CD4 lymphocytes specifically recognize a peptide representing the fusion region of the hybrid protein pml/RARα present in acute promyelocytic leukemia cells" Blood, 81(5):1369-1375 (Mar. 1993).
Wang RF and Rosenberg SA., "Human tumor antigens for cancer vaccine development", Immunol. Rev., 170:85-100 (Aug. 1999).
Brose MS et al., "*BRAF* and *RAS* mutations in human lung cancer and melanoma" Cancer Res., 62:6997-7000 (Dec. 2002).
Pollock PM, et al., "High frequency of BRAF mutations in nevi", Nat. Genet., 33:19-20 (Jan. 2003, e-publication Nov. 2002).
Michaloglou C., et al., "BRAF$^{E600}$-associated senescence-like cell cycle arrest of human naevi", Nature, 436(4):720-724 (Aug. 2005).
Sharkey MS et al, "CD4+ T-cell recognition of mutated B-RAF in melanoma patients harboring the V599E mutation", Cancer Res., 64:1595-1599 (Mar. 2004).
Takahashi M, et al., "Antibody to ras proteins in patients with colon cancer", Clin. Cancer Res., 1:1071-1077 (Oct. 2005).
Davies, H, et al., "Mutations of the BRAF gene in human cancer", Nature, 417:949-954 (Jun. 2002).
Terasaki, PI and Gjertson, DW, "HLA 1997: UCLA Tissue Typing Laboratory", p. 174-427 (1997), Los Angeles, California.

*Primary Examiner*—Sheela J Huff
(74) *Attorney, Agent, or Firm* — Howson & Howson LLP

(57) ABSTRACT

Novel BRAF$^{V600E}$ mutant peptides or a pharmaceutically acceptable salt thereof, that induce MHC Class I-dependent cytotoxic T cell responses in mammals are useful in prophylactic, diagnostic and therapeutic treatments for melanoma. Such compounds are also useful in drug development for non-peptide mimics of the compounds described herein and in the development of therapeutic or diagnostic antibodies.

21 Claims, 6 Drawing Sheets

```
                           SEQUENCE LISTING

<160> NUMBER OF SEQ ID NOS: 550

<210> SEQ ID NO 1
<211> LENGTH: 29
<212> TYPE: PRT
<213> ORGANISM: homo sapiens

<400> SEQUENCE: 1

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu Ser
            20                  25

<210> SEQ ID NO 2
<211> LENGTH: 9
<212> TYPE: PRT
<213> ORGANISM: homo sapiens

<400> SEQUENCE: 2
```

```
Phe Gly Leu Ala Thr Glu Lys Ser Arg
1               5

<210> SEQ ID NO 3
<211> LENGTH: 9
<212> TYPE: PRT
<213> ORGANISM: homo sapiens

<400> SEQUENCE: 3

Gly Arg Phe Gly Leu Ala Thr Glu Lys
1               5

<210> SEQ ID NO 4
<211> LENGTH: 14
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or gly
<220> FEATURE:
<221> NAME/KEY: MISC_FEATURE
<222> LOCATION: (2)..(2)
<223> OTHER INFORMATION: can be absent or cys or ser
<220> FEATURE:
<221> NAME/KEY: MISC_FEATURE
<222> LOCATION: (4)..(4)
<223> OTHER INFORMATION: can be a substituted or unsubstituted Ala or
      Leu or Met or Val or Pro or Gly
<220> FEATURE:
<221> NAME/KEY: MISC_FEATURE
<222> LOCATION: (5)..(5)
<223> OTHER INFORMATION: can be a substituted or unsubstituted Thr or
      Ser
<220> FEATURE:
<221> NAME/KEY: MISC_FEATURE
<222> LOCATION: (7)..(7)
<223> OTHER INFORMATION: can be a substituted or unsubstituted Lys or
      Arg or His
<220> FEATURE:
<221> NAME/KEY: MISC_FEATURE
<222> LOCATION: (8)..(8)
<223> OTHER INFORMATION: can be a substituted or unsubstituted Ser or
      Thr
<220> FEATURE:
<221> NAME/KEY: MISC_FEATURE
<222> LOCATION: (9)..(9)
<223> OTHER INFORMATION: can be a substituted or unsubstituted Arg or
      Lys or His
<220> FEATURE:
<221> NAME/KEY: MISC_FEATURE
<222> LOCATION: (11)..(11)
<223> OTHER INFORMATION: can be a substituted or unsubstituted Thr or
      Val or Leu or Ser
<220> FEATURE:
<221> NAME/KEY: MISC_FEATURE
<222> LOCATION: (12)..(12)
<223> OTHER INFORMATION: can be absent or a substituted or unsubstituted
      Gly or Pro or Leu
<220> FEATURE:
<221> NAME/KEY: MISC_FEATURE
<222> LOCATION: (13)..(13)
<223> OTHER INFORMATION: can be absent or cys or gly
<220> FEATURE:
<221> NAME/KEY: MISC_FEATURE
<222> LOCATION: (14)..(14)
<223> OTHER INFORMATION: can be absent or ser

<400> SEQUENCE: 4

Xaa Xaa Leu Xaa Xaa Glu Xaa Xaa Xaa Trp Xaa Xaa Xaa Xaa
1               5                   10

<210> SEQ ID NO 5
```

```
<211> LENGTH: 10
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: can be a substituted or unsubstituted Ala or
      Leu or Val or Met
<220> FEATURE:
<221> NAME/KEY: MISC_FEATURE
<222> LOCATION: (10)..(10)
<223> OTHER INFORMATION: can be absent or a substituted or unsubstituted
      Gly or Cys or Pro or Leu

<400> SEQUENCE: 5

Leu Xaa Thr Glu Lys Ser Arg Trp Ser Xaa
1               5                   10

<210> SEQ ID NO 6
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (3)..(3)
<223> OTHER INFORMATION: can be a substituted or unsubstituted Ala or
      Leu or Val or Met
<220> FEATURE:
<221> NAME/KEY: MISC_FEATURE
<222> LOCATION: (10)..(10)
<223> OTHER INFORMATION: can be a substituted or unsubstituted Ser or
      Leu or Val or Thr
<220> FEATURE:
<221> NAME/KEY: MISC_FEATURE
<222> LOCATION: (11)..(11)
<223> OTHER INFORMATION: can be absent or a substituted or unsubstituted
      Gly or Cys or Pro or Leu
<220> FEATURE:
<221> NAME/KEY: MISC_FEATURE
<222> LOCATION: (12)..(12)
<223> OTHER INFORMATION: can be absent or Cys

<400> SEQUENCE: 6

Xaa Leu Xaa Thr Glu Lys Ser Arg Trp Xaa Xaa Xaa
1               5                   10

<210> SEQ ID NO 7
<211> LENGTH: 10
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: can be a substituted or unsubstituted Ala or
      Leu or Val or Met
<220> FEATURE:
<221> NAME/KEY: MISC_FEATURE
<222> LOCATION: (9)..(9)
<223> OTHER INFORMATION: can be a substituted or unsubstituted Ser or
      Leu or Val
<220> FEATURE:
<221> NAME/KEY: MISC_FEATURE
<222> LOCATION: (10)..(10)
<223> OTHER INFORMATION: can be absent or a substituted or unsubstituted
      Gly or Cys or Pro or Leu

<400> SEQUENCE: 7

Leu Xaa Ser Glu Lys Ser Arg Trp Xaa Xaa
1               5                   10
```

```
<210> SEQ ID NO 8
<211> LENGTH: 9
<212> TYPE: PRT
<213> ORGANISM: homo sapiens

<400> SEQUENCE: 8

Leu Ala Thr Glu Lys Ser Arg Trp Ser
1               5

<210> SEQ ID NO 9
<211> LENGTH: 10
<212> TYPE: PRT
<213> ORGANISM: homo sapiens

<400> SEQUENCE: 9

Leu Ala Thr Glu Lys Ser Arg Trp Ser Gly
1               5                   10

<210> SEQ ID NO 10
<211> LENGTH: 10
<212> TYPE: PRT
<213> ORGANISM: homo sapiens

<400> SEQUENCE: 10

Cys Leu Ala Thr Glu Lys Ser Arg Trp Ser
1               5                   10

<210> SEQ ID NO 11
<211> LENGTH: 11
<212> TYPE: PRT
<213> ORGANISM: homo sapiens

<400> SEQUENCE: 11

Cys Leu Ala Thr Glu Lys Ser Arg Trp Ser Gly
1               5                   10

<210> SEQ ID NO 12
<211> LENGTH: 10
<212> TYPE: PRT
<213> ORGANISM: homo sapiens

<400> SEQUENCE: 12

Leu Ala Thr Glu Lys Ser Arg Trp Ser Cys
1               5                   10

<210> SEQ ID NO 13
<211> LENGTH: 11
<212> TYPE: PRT
<213> ORGANISM: homo sapiens

<400> SEQUENCE: 13

Leu Ala Thr Glu Lys Ser Arg Trp Ser Gly Cys
1               5                   10

<210> SEQ ID NO 14
<211> LENGTH: 9
<212> TYPE: PRT
<213> ORGANISM: homo sapiens

<400> SEQUENCE: 14

Leu Leu Thr Glu Lys Ser Arg Trp Ser
1               5

<210> SEQ ID NO 15
```

```
<211> LENGTH: 10
<212> TYPE: PRT
<213> ORGANISM: homo sapiens

<400> SEQUENCE: 15

Leu Leu Thr Glu Lys Ser Arg Trp Ser Gly
1               5                   10

<210> SEQ ID NO 16
<211> LENGTH: 10
<212> TYPE: PRT
<213> ORGANISM: homo sapiens

<400> SEQUENCE: 16

Cys Leu Leu Thr Glu Lys Ser Arg Trp Ser
1               5                   10

<210> SEQ ID NO 17
<211> LENGTH: 11
<212> TYPE: PRT
<213> ORGANISM: homo sapiens

<400> SEQUENCE: 17

Cys Leu Leu Thr Glu Lys Ser Arg Trp Ser Gly
1               5                   10

<210> SEQ ID NO 18
<211> LENGTH: 10
<212> TYPE: PRT
<213> ORGANISM: homo sapiens

<400> SEQUENCE: 18

Leu Leu Thr Glu Lys Ser Arg Trp Ser Cys
1               5                   10

<210> SEQ ID NO 19
<211> LENGTH: 11
<212> TYPE: PRT
<213> ORGANISM: homo sapiens

<400> SEQUENCE: 19

Leu Leu Thr Glu Lys Ser Arg Trp Ser Gly Cys
1               5                   10

<210> SEQ ID NO 20
<211> LENGTH: 9
<212> TYPE: PRT
<213> ORGANISM: homo sapiens

<400> SEQUENCE: 20

Leu Val Thr Glu Lys Ser Arg Trp Ser
1               5

<210> SEQ ID NO 21
<211> LENGTH: 10
<212> TYPE: PRT
<213> ORGANISM: homo sapiens

<400> SEQUENCE: 21

Leu Val Thr Glu Lys Ser Arg Trp Ser Gly
1               5                   10

<210> SEQ ID NO 22
<211> LENGTH: 10
<212> TYPE: PRT
```

<213> ORGANISM: homo sapiens

<400> SEQUENCE: 22

Cys Leu Val Thr Glu Lys Ser Arg Trp Ser
1               5                   10

<210> SEQ ID NO 23
<211> LENGTH: 11
<212> TYPE: PRT
<213> ORGANISM: homo sapiens

<400> SEQUENCE: 23

Cys Leu Val Thr Glu Lys Ser Arg Trp Ser Gly
1               5                   10

<210> SEQ ID NO 24
<211> LENGTH: 10
<212> TYPE: PRT
<213> ORGANISM: homo sapiens

<400> SEQUENCE: 24

Leu Val Thr Glu Lys Ser Arg Trp Ser Cys
1               5                   10

<210> SEQ ID NO 25
<211> LENGTH: 11
<212> TYPE: PRT
<213> ORGANISM: homo sapiens

<400> SEQUENCE: 25

Leu Val Thr Glu Lys Ser Arg Trp Ser Gly Cys
1               5                   10

<210> SEQ ID NO 26
<211> LENGTH: 9
<212> TYPE: PRT
<213> ORGANISM: homo sapiens

<400> SEQUENCE: 26

Leu Met Thr Glu Lys Ser Arg Trp Ser
1               5

<210> SEQ ID NO 27
<211> LENGTH: 10
<212> TYPE: PRT
<213> ORGANISM: homo sapiens

<400> SEQUENCE: 27

Leu Met Thr Glu Lys Ser Arg Trp Ser Gly
1               5                   10

<210> SEQ ID NO 28
<211> LENGTH: 10
<212> TYPE: PRT
<213> ORGANISM: homo sapiens

<400> SEQUENCE: 28

Cys Leu Met Thr Glu Lys Ser Arg Trp Ser
1               5                   10

<210> SEQ ID NO 29
<211> LENGTH: 11
<212> TYPE: PRT

```
<400> SEQUENCE: 29

Cys Leu Met Thr Glu Lys Ser Arg Trp Ser Gly
1               5                   10

<210> SEQ ID NO 30
<211> LENGTH: 10
<212> TYPE: PRT
<213> ORGANISM: homo sapiens

<400> SEQUENCE: 30

Leu Met Thr Glu Lys Ser Arg Trp Ser Cys
1               5                   10

<210> SEQ ID NO 31
<211> LENGTH: 11
<212> TYPE: PRT
<213> ORGANISM: homo sapiens

<400> SEQUENCE: 31

Leu Met Thr Glu Lys Ser Arg Trp Ser Gly Cys
1               5                   10

<210> SEQ ID NO 32
<211> LENGTH: 9
<212> TYPE: PRT
<213> ORGANISM: homo sapiens

<400> SEQUENCE: 32

Leu Pro Thr Glu Lys Ser Arg Trp Ser
1               5

<210> SEQ ID NO 33
<211> LENGTH: 10
<212> TYPE: PRT
<213> ORGANISM: homo sapiens

<400> SEQUENCE: 33

Leu Pro Thr Glu Lys Ser Arg Trp Ser Gly
1               5                   10

<210> SEQ ID NO 34
<211> LENGTH: 10
<212> TYPE: PRT
<213> ORGANISM: homo sapiens

<400> SEQUENCE: 34

Cys Leu Pro Thr Glu Lys Ser Arg Trp Ser
1               5                   10

<210> SEQ ID NO 35
<211> LENGTH: 11
<212> TYPE: PRT
<213> ORGANISM: homo sapiens

<400> SEQUENCE: 35

Cys Leu Pro Thr Glu Lys Ser Arg Trp Ser Gly
1               5                   10

<210> SEQ ID NO 36
<211> LENGTH: 10
<212> TYPE: PRT
<213> ORGANISM: homo sapiens

<400> SEQUENCE: 36
```

```
Leu Pro Thr Glu Lys Ser Arg Trp Ser Cys
1               5                   10

<210> SEQ ID NO 37
<211> LENGTH: 11
<212> TYPE: PRT
<213> ORGANISM: homo sapiens

<400> SEQUENCE: 37

Leu Pro Thr Glu Lys Ser Arg Trp Ser Gly Cys
1               5                   10

<210> SEQ ID NO 38
<211> LENGTH: 9
<212> TYPE: PRT
<213> ORGANISM: homo sapiens

<400> SEQUENCE: 38

Leu Gly Thr Glu Lys Ser Arg Trp Ser
1               5

<210> SEQ ID NO 39
<211> LENGTH: 10
<212> TYPE: PRT
<213> ORGANISM: homo sapiens

<400> SEQUENCE: 39

Leu Gly Thr Glu Lys Ser Arg Trp Ser Gly
1               5                   10

<210> SEQ ID NO 40
<211> LENGTH: 10
<212> TYPE: PRT
<213> ORGANISM: homo sapiens

<400> SEQUENCE: 40

Cys Leu Gly Thr Glu Lys Ser Arg Trp Ser
1               5                   10

<210> SEQ ID NO 41
<211> LENGTH: 11
<212> TYPE: PRT
<213> ORGANISM: homo sapiens

<400> SEQUENCE: 41

Cys Leu Gly Thr Glu Lys Ser Arg Trp Ser Gly
1               5                   10

<210> SEQ ID NO 42
<211> LENGTH: 10
<212> TYPE: PRT
<213> ORGANISM: homo sapiens

<400> SEQUENCE: 42

Leu Gly Thr Glu Lys Ser Arg Trp Ser Cys
1               5                   10

<210> SEQ ID NO 43
<211> LENGTH: 11
<212> TYPE: PRT
<213> ORGANISM: homo sapiens

<400> SEQUENCE: 43

Leu Gly Thr Glu Lys Ser Arg Trp Ser Gly Cys
1               5                   10
```

<210> SEQ ID NO 44
<211> LENGTH: 9
<212> TYPE: PRT
<213> ORGANISM: homo sapiens

<400> SEQUENCE: 44

Leu Ala Thr Glu Lys Ser Arg Trp Leu
1               5

<210> SEQ ID NO 45
<211> LENGTH: 10
<212> TYPE: PRT
<213> ORGANISM: homo sapiens

<400> SEQUENCE: 45

Leu Ala Thr Glu Lys Ser Arg Trp Leu Gly
1               5                   10

<210> SEQ ID NO 46
<211> LENGTH: 10
<212> TYPE: PRT
<213> ORGANISM: homo sapiens

<400> SEQUENCE: 46

Cys Leu Ala Thr Glu Lys Ser Arg Trp Leu
1               5                   10

<210> SEQ ID NO 47
<211> LENGTH: 11
<212> TYPE: PRT
<213> ORGANISM: homo sapiens

<400> SEQUENCE: 47

Cys Leu Ala Thr Glu Lys Ser Arg Trp Leu Gly
1               5                   10

<210> SEQ ID NO 48
<211> LENGTH: 10
<212> TYPE: PRT
<213> ORGANISM: homo sapiens

<400> SEQUENCE: 48

Leu Ala Thr Glu Lys Ser Arg Trp Leu Cys
1               5                   10

<210> SEQ ID NO 49
<211> LENGTH: 11
<212> TYPE: PRT
<213> ORGANISM: homo sapiens

<400> SEQUENCE: 49

Leu Ala Thr Glu Lys Ser Arg Trp Leu Gly Cys
1               5                   10

<210> SEQ ID NO 50
<211> LENGTH: 9
<212> TYPE: PRT
<213> ORGANISM: homo sapiens

<400> SEQUENCE: 50

Leu Ala Thr Glu Lys Ser Arg Trp Val
1               5

<210> SEQ ID NO 51
<211> LENGTH: 10
<212> TYPE: PRT
<213> ORGANISM: homo sapiens

<400> SEQUENCE: 51

Leu Ala Thr Glu Lys Ser Arg Trp Val Gly
1               5                   10

<210> SEQ ID NO 52
<211> LENGTH: 10
<212> TYPE: PRT
<213> ORGANISM: homo sapiens

<400> SEQUENCE: 52

Cys Leu Ala Thr Glu Lys Ser Arg Trp Val
1               5                   10

<210> SEQ ID NO 53
<211> LENGTH: 11
<212> TYPE: PRT
<213> ORGANISM: homo sapiens

<400> SEQUENCE: 53

Cys Leu Ala Thr Glu Lys Ser Arg Trp Val Gly
1               5                   10

<210> SEQ ID NO 54
<211> LENGTH: 10
<212> TYPE: PRT
<213> ORGANISM: homo sapiens

<400> SEQUENCE: 54

Leu Ala Thr Glu Lys Ser Arg Trp Val Cys
1               5                   10

<210> SEQ ID NO 55
<211> LENGTH: 11
<212> TYPE: PRT
<213> ORGANISM: homo sapiens

<400> SEQUENCE: 55

Leu Ala Thr Glu Lys Ser Arg Trp Val Gly Cys
1               5                   10

<210> SEQ ID NO 56
<211> LENGTH: 9
<212> TYPE: PRT
<213> ORGANISM: homo sapiens

<400> SEQUENCE: 56

Leu Ala Thr Glu Lys Ser Arg Trp Thr
1               5

<210> SEQ ID NO 57
<211> LENGTH: 10
<212> TYPE: PRT
<213> ORGANISM: homo sapiens

<400> SEQUENCE: 57

Leu Ala Thr Glu Lys Ser Arg Trp Thr Gly
1               5                   10

<210> SEQ ID NO 58
<211> LENGTH: 10

```
<212> TYPE: PRT
<213> ORGANISM: homo sapiens

<400> SEQUENCE: 58

Cys Leu Ala Thr Glu Lys Ser Arg Trp Thr
1               5                   10

<210> SEQ ID NO 59
<211> LENGTH: 11
<212> TYPE: PRT
<213> ORGANISM: homo sapiens

<400> SEQUENCE: 59

Cys Leu Ala Thr Glu Lys Ser Arg Trp Thr Gly
1               5                   10

<210> SEQ ID NO 60
<211> LENGTH: 10
<212> TYPE: PRT
<213> ORGANISM: homo sapiens

<400> SEQUENCE: 60

Leu Ala Thr Glu Lys Ser Arg Trp Thr Cys
1               5                   10

<210> SEQ ID NO 61
<211> LENGTH: 11
<212> TYPE: PRT
<213> ORGANISM: homo sapiens

<400> SEQUENCE: 61

Leu Ala Thr Glu Lys Ser Arg Trp Thr Gly Cys
1               5                   10

<210> SEQ ID NO 62
<211> LENGTH: 9
<212> TYPE: PRT
<213> ORGANISM: homo sapiens

<400> SEQUENCE: 62

Leu Leu Thr Glu Lys Ser Arg Trp Val
1               5

<210> SEQ ID NO 63
<211> LENGTH: 10
<212> TYPE: PRT
<213> ORGANISM: homo sapiens

<400> SEQUENCE: 63

Leu Leu Thr Glu Lys Ser Arg Trp Val Gly
1               5                   10

<210> SEQ ID NO 64
<211> LENGTH: 10
<212> TYPE: PRT
<213> ORGANISM: homo sapiens

<400> SEQUENCE: 64

Cys Leu Leu Thr Glu Lys Ser Arg Trp Val
1               5                   10

<210> SEQ ID NO 65
<211> LENGTH: 11
<212> TYPE: PRT
<213> ORGANISM: homo sapiens
```

```
<400> SEQUENCE: 65

Cys Leu Leu Thr Glu Lys Ser Arg Trp Val Gly
1               5                   10

<210> SEQ ID NO 66
<211> LENGTH: 10
<212> TYPE: PRT
<213> ORGANISM: homo sapiens

<400> SEQUENCE: 66

Leu Leu Thr Glu Lys Ser Arg Trp Val Cys
1               5                   10

<210> SEQ ID NO 67
<211> LENGTH: 11
<212> TYPE: PRT
<213> ORGANISM: homo sapiens

<400> SEQUENCE: 67

Leu Leu Thr Glu Lys Ser Arg Trp Val Gly Cys
1               5                   10

<210> SEQ ID NO 68
<211> LENGTH: 9
<212> TYPE: PRT
<213> ORGANISM: homo sapiens

<400> SEQUENCE: 68

Leu Val Thr Glu Lys Ser Arg Trp Leu
1               5

<210> SEQ ID NO 69
<211> LENGTH: 10
<212> TYPE: PRT
<213> ORGANISM: homo sapiens

<400> SEQUENCE: 69

Leu Val Thr Glu Lys Ser Arg Trp Leu Gly
1               5                   10

<210> SEQ ID NO 70
<211> LENGTH: 10
<212> TYPE: PRT
<213> ORGANISM: homo sapiens

<400> SEQUENCE: 70

Cys Leu Val Thr Glu Lys Ser Arg Trp Leu
1               5                   10

<210> SEQ ID NO 71
<211> LENGTH: 11
<212> TYPE: PRT
<213> ORGANISM: homo sapiens

<400> SEQUENCE: 71

Cys Leu Val Thr Glu Lys Ser Arg Trp Leu Gly
1               5                   10

<210> SEQ ID NO 72
<211> LENGTH: 10
<212> TYPE: PRT
<213> ORGANISM: homo sapiens

<400> SEQUENCE: 72
```

```
Leu Val Thr Glu Lys Ser Arg Trp Leu Cys
1               5                   10

<210> SEQ ID NO 73
<211> LENGTH: 11
<212> TYPE: PRT
<213> ORGANISM: homo sapiens

<400> SEQUENCE: 73

Leu Val Thr Glu Lys Ser Arg Trp Leu Gly Cys
1               5                   10

<210> SEQ ID NO 74
<211> LENGTH: 9
<212> TYPE: PRT
<213> ORGANISM: homo sapiens

<400> SEQUENCE: 74

Leu Ala Ser Glu Lys Ser Arg Trp Ser
1               5

<210> SEQ ID NO 75
<211> LENGTH: 10
<212> TYPE: PRT
<213> ORGANISM: homo sapiens

<400> SEQUENCE: 75

Leu Ala Ser Glu Lys Ser Arg Trp Ser Gly
1               5                   10

<210> SEQ ID NO 76
<211> LENGTH: 10
<212> TYPE: PRT
<213> ORGANISM: homo sapiens

<400> SEQUENCE: 76

Cys Leu Ala Ser Glu Lys Ser Arg Trp Ser
1               5                   10

<210> SEQ ID NO 77
<211> LENGTH: 11
<212> TYPE: PRT
<213> ORGANISM: homo sapiens

<400> SEQUENCE: 77

Cys Leu Ala Ser Glu Lys Ser Arg Trp Ser Gly
1               5                   10

<210> SEQ ID NO 78
<211> LENGTH: 10
<212> TYPE: PRT
<213> ORGANISM: homo sapiens

<400> SEQUENCE: 78

Leu Ala Ser Glu Lys Ser Arg Trp Ser Cys
1               5                   10

<210> SEQ ID NO 79
<211> LENGTH: 11
<212> TYPE: PRT
<213> ORGANISM: homo sapiens

<400> SEQUENCE: 79

Leu Ala Ser Glu Lys Ser Arg Trp Ser Gly Cys
```

-continued

```
1               5                   10

<210> SEQ ID NO 80
<211> LENGTH: 9
<212> TYPE: PRT
<213> ORGANISM: homo sapiens

<400> SEQUENCE: 80

Leu Leu Ser Glu Lys Ser Arg Trp Ser
1               5

<210> SEQ ID NO 81
<211> LENGTH: 10
<212> TYPE: PRT
<213> ORGANISM: homo sapiens

<400> SEQUENCE: 81

Leu Leu Ser Glu Lys Ser Arg Trp Ser Gly
1               5                   10

<210> SEQ ID NO 82
<211> LENGTH: 10
<212> TYPE: PRT
<213> ORGANISM: homo sapiens

<400> SEQUENCE: 82

Cys Leu Leu Ser Glu Lys Ser Arg Trp Ser
1               5                   10

<210> SEQ ID NO 83
<211> LENGTH: 11
<212> TYPE: PRT
<213> ORGANISM: homo sapiens

<400> SEQUENCE: 83

Cys Leu Leu Ser Glu Lys Ser Arg Trp Ser Gly
1               5                   10

<210> SEQ ID NO 84
<211> LENGTH: 10
<212> TYPE: PRT
<213> ORGANISM: homo sapiens

<400> SEQUENCE: 84

Leu Leu Ser Glu Lys Ser Arg Trp Ser Cys
1               5                   10

<210> SEQ ID NO 85
<211> LENGTH: 11
<212> TYPE: PRT
<213> ORGANISM: homo sapiens

<400> SEQUENCE: 85

Leu Leu Ser Glu Lys Ser Arg Trp Ser Gly Cys
1               5                   10

<210> SEQ ID NO 86
<211> LENGTH: 9
<212> TYPE: PRT
<213> ORGANISM: homo sapiens

<400> SEQUENCE: 86

Leu Leu Ser Glu Lys Ser Arg Trp Ser
1               5
```

<210> SEQ ID NO 87
<211> LENGTH: 9
<212> TYPE: PRT
<213> ORGANISM: homo sapiens

<400> SEQUENCE: 87

Leu Val Ser Glu Lys Ser Arg Trp Ser
1               5

<210> SEQ ID NO 88
<211> LENGTH: 10
<212> TYPE: PRT
<213> ORGANISM: homo sapiens

<400> SEQUENCE: 88

Leu Val Ser Glu Lys Ser Arg Trp Ser Gly
1               5                   10

<210> SEQ ID NO 89
<211> LENGTH: 10
<212> TYPE: PRT
<213> ORGANISM: homo sapiens

<400> SEQUENCE: 89

Cys Leu Val Ser Glu Lys Ser Arg Trp Ser
1               5                   10

<210> SEQ ID NO 90
<211> LENGTH: 11
<212> TYPE: PRT
<213> ORGANISM: homo sapiens

<400> SEQUENCE: 90

Cys Leu Val Ser Glu Lys Ser Arg Trp Ser Gly
1               5                   10

<210> SEQ ID NO 91
<211> LENGTH: 10
<212> TYPE: PRT
<213> ORGANISM: homo sapiens

<400> SEQUENCE: 91

Leu Val Ser Glu Lys Ser Arg Trp Ser Cys
1               5                   10

<210> SEQ ID NO 92
<211> LENGTH: 11
<212> TYPE: PRT
<213> ORGANISM: homo sapiens

<400> SEQUENCE: 92

Leu Val Ser Glu Lys Ser Arg Trp Ser Gly Cys
1               5                   10

<210> SEQ ID NO 93
<211> LENGTH: 9
<212> TYPE: PRT
<213> ORGANISM: homo sapiens

<400> SEQUENCE: 93

Leu Met Ser Glu Lys Ser Arg Trp Ser
1               5

<210> SEQ ID NO 94

```
<211> LENGTH: 10
<212> TYPE: PRT
<213> ORGANISM: homo sapiens

<400> SEQUENCE: 94

Leu Met Ser Glu Lys Ser Arg Trp Ser Gly
1               5                   10

<210> SEQ ID NO 95
<211> LENGTH: 10
<212> TYPE: PRT
<213> ORGANISM: homo sapiens

<400> SEQUENCE: 95

Cys Leu Met Ser Glu Lys Ser Arg Trp Ser
1               5                   10

<210> SEQ ID NO 96
<211> LENGTH: 11
<212> TYPE: PRT
<213> ORGANISM: homo sapiens

<400> SEQUENCE: 96

Cys Leu Met Ser Glu Lys Ser Arg Trp Ser Gly
1               5                   10

<210> SEQ ID NO 97
<211> LENGTH: 10
<212> TYPE: PRT
<213> ORGANISM: homo sapiens

<400> SEQUENCE: 97

Leu Met Ser Glu Lys Ser Arg Trp Ser Cys
1               5                   10

<210> SEQ ID NO 98
<211> LENGTH: 11
<212> TYPE: PRT
<213> ORGANISM: homo sapiens

<400> SEQUENCE: 98

Leu Met Ser Glu Lys Ser Arg Trp Ser Gly Cys
1               5                   10

<210> SEQ ID NO 99
<211> LENGTH: 9
<212> TYPE: PRT
<213> ORGANISM: homo sapiens

<400> SEQUENCE: 99

Leu Pro Ser Glu Lys Ser Arg Trp Ser
1               5

<210> SEQ ID NO 100
<211> LENGTH: 10
<212> TYPE: PRT
<213> ORGANISM: homo sapiens

<400> SEQUENCE: 100

Leu Pro Ser Glu Lys Ser Arg Trp Ser Gly
1               5                   10

<210> SEQ ID NO 101
<211> LENGTH: 10
<212> TYPE: PRT
```

<213> ORGANISM: homo sapiens

<400> SEQUENCE: 101

Cys Leu Pro Ser Glu Lys Ser Arg Trp Ser
1               5                   10

<210> SEQ ID NO 102
<211> LENGTH: 11
<212> TYPE: PRT
<213> ORGANISM: homo sapiens

<400> SEQUENCE: 102

Cys Leu Pro Ser Glu Lys Ser Arg Trp Ser Gly
1               5                   10

<210> SEQ ID NO 103
<211> LENGTH: 10
<212> TYPE: PRT
<213> ORGANISM: homo sapiens

<400> SEQUENCE: 103

Leu Pro Ser Glu Lys Ser Arg Trp Ser Cys
1               5                   10

<210> SEQ ID NO 104
<211> LENGTH: 11
<212> TYPE: PRT
<213> ORGANISM: homo sapiens

<400> SEQUENCE: 104

Leu Pro Ser Glu Lys Ser Arg Trp Ser Gly Cys
1               5                   10

<210> SEQ ID NO 105
<211> LENGTH: 9
<212> TYPE: PRT
<213> ORGANISM: homo sapiens

<400> SEQUENCE: 105

Leu Gly Ser Glu Lys Ser Arg Trp Ser
1               5

<210> SEQ ID NO 106
<211> LENGTH: 10
<212> TYPE: PRT
<213> ORGANISM: homo sapiens

<400> SEQUENCE: 106

Leu Gly Ser Glu Lys Ser Arg Trp Ser Gly
1               5                   10

<210> SEQ ID NO 107
<211> LENGTH: 10
<212> TYPE: PRT
<213> ORGANISM: homo sapiens

<400> SEQUENCE: 107

Cys Leu Gly Ser Glu Lys Ser Arg Trp Ser
1               5                   10

<210> SEQ ID NO 108
<211> LENGTH: 11
<212> TYPE: PRT
<213> ORGANISM: homo sapiens

```
<400> SEQUENCE: 108

Cys Leu Gly Ser Glu Lys Ser Arg Trp Ser Gly
1               5                   10

<210> SEQ ID NO 109
<211> LENGTH: 10
<212> TYPE: PRT
<213> ORGANISM: homo sapiens

<400> SEQUENCE: 109

Leu Gly Ser Glu Lys Ser Arg Trp Ser Cys
1               5                   10

<210> SEQ ID NO 110
<211> LENGTH: 11
<212> TYPE: PRT
<213> ORGANISM: homo sapiens

<400> SEQUENCE: 110

Leu Gly Ser Glu Lys Ser Arg Trp Ser Gly Cys
1               5                   10

<210> SEQ ID NO 111
<211> LENGTH: 9
<212> TYPE: PRT
<213> ORGANISM: homo sapiens

<400> SEQUENCE: 111

Leu Ala Ser Glu Lys Ser Arg Trp Leu
1               5

<210> SEQ ID NO 112
<211> LENGTH: 10
<212> TYPE: PRT
<213> ORGANISM: homo sapiens

<400> SEQUENCE: 112

Leu Ala Ser Glu Lys Ser Arg Trp Leu Gly
1               5                   10

<210> SEQ ID NO 113
<211> LENGTH: 10
<212> TYPE: PRT
<213> ORGANISM: homo sapiens

<400> SEQUENCE: 113

Cys Leu Ala Ser Glu Lys Ser Arg Trp Leu
1               5                   10

<210> SEQ ID NO 114
<211> LENGTH: 11
<212> TYPE: PRT
<213> ORGANISM: homo sapiens

<400> SEQUENCE: 114

Cys Leu Ala Ser Glu Lys Ser Arg Trp Leu Gly
1               5                   10

<210> SEQ ID NO 115
<211> LENGTH: 10
<212> TYPE: PRT
<213> ORGANISM: homo sapiens

<400> SEQUENCE: 115
```

```
Leu Ala Ser Glu Lys Ser Arg Trp Leu Cys
1               5                   10

<210> SEQ ID NO 116
<211> LENGTH: 11
<212> TYPE: PRT
<213> ORGANISM: homo sapiens

<400> SEQUENCE: 116

Leu Ala Ser Glu Lys Ser Arg Trp Leu Gly Cys
1               5                   10

<210> SEQ ID NO 117
<211> LENGTH: 9
<212> TYPE: PRT
<213> ORGANISM: homo sapiens

<400> SEQUENCE: 117

Leu Ala Ser Glu Lys Ser Arg Trp Val
1               5

<210> SEQ ID NO 118
<211> LENGTH: 10
<212> TYPE: PRT
<213> ORGANISM: homo sapiens

<400> SEQUENCE: 118

Leu Ala Ser Glu Lys Ser Arg Trp Val Gly
1               5                   10

<210> SEQ ID NO 119
<211> LENGTH: 10
<212> TYPE: PRT
<213> ORGANISM: homo sapiens

<400> SEQUENCE: 119

Cys Leu Ala Ser Glu Lys Ser Arg Trp Val
1               5                   10

<210> SEQ ID NO 120
<211> LENGTH: 11
<212> TYPE: PRT
<213> ORGANISM: homo sapiens

<400> SEQUENCE: 120

Cys Leu Ala Ser Glu Lys Ser Arg Trp Val Gly
1               5                   10

<210> SEQ ID NO 121
<211> LENGTH: 10
<212> TYPE: PRT
<213> ORGANISM: homo sapiens

<400> SEQUENCE: 121

Leu Ala Ser Glu Lys Ser Arg Trp Val Cys
1               5                   10

<210> SEQ ID NO 122
<211> LENGTH: 11
<212> TYPE: PRT
<213> ORGANISM: homo sapiens

<400> SEQUENCE: 122

Leu Ala Ser Glu Lys Ser Arg Trp Val Gly Cys
1               5                   10
```

<210> SEQ ID NO 123
<211> LENGTH: 9
<212> TYPE: PRT
<213> ORGANISM: homo sapiens

<400> SEQUENCE: 123

Leu Leu Ser Glu Lys Ser Arg Trp Val
1               5

<210> SEQ ID NO 124
<211> LENGTH: 10
<212> TYPE: PRT
<213> ORGANISM: homo sapiens

<400> SEQUENCE: 124

Leu Leu Ser Glu Lys Ser Arg Trp Val Gly
1               5                   10

<210> SEQ ID NO 125
<211> LENGTH: 10
<212> TYPE: PRT
<213> ORGANISM: homo sapiens

<400> SEQUENCE: 125

Cys Leu Leu Ser Glu Lys Ser Arg Trp Val
1               5                   10

<210> SEQ ID NO 126
<211> LENGTH: 11
<212> TYPE: PRT
<213> ORGANISM: homo sapiens

<400> SEQUENCE: 126

Cys Leu Leu Ser Glu Lys Ser Arg Trp Val Gly
1               5                   10

<210> SEQ ID NO 127
<211> LENGTH: 10
<212> TYPE: PRT
<213> ORGANISM: homo sapiens

<400> SEQUENCE: 127

Leu Leu Ser Glu Lys Ser Arg Trp Val Cys
1               5                   10

<210> SEQ ID NO 128
<211> LENGTH: 11
<212> TYPE: PRT
<213> ORGANISM: homo sapiens

<400> SEQUENCE: 128

Leu Leu Ser Glu Lys Ser Arg Trp Val Gly Cys
1               5                   10

<210> SEQ ID NO 129
<211> LENGTH: 9
<212> TYPE: PRT
<213> ORGANISM: homo sapiens

<400> SEQUENCE: 129

Leu Val Ser Glu Lys Ser Arg Trp Leu
1               5

```
<210> SEQ ID NO 130
<211> LENGTH: 10
<212> TYPE: PRT
<213> ORGANISM: homo sapiens

<400> SEQUENCE: 130

Leu Val Ser Glu Lys Ser Arg Trp Leu Gly
1               5                   10

<210> SEQ ID NO 131
<211> LENGTH: 10
<212> TYPE: PRT
<213> ORGANISM: homo sapiens

<400> SEQUENCE: 131

Cys Leu Val Ser Glu Lys Ser Arg Trp Leu
1               5                   10

<210> SEQ ID NO 132
<211> LENGTH: 11
<212> TYPE: PRT
<213> ORGANISM: homo sapiens

<400> SEQUENCE: 132

Cys Leu Val Ser Glu Lys Ser Arg Trp Leu Gly
1               5                   10

<210> SEQ ID NO 133
<211> LENGTH: 10
<212> TYPE: PRT
<213> ORGANISM: homo sapiens

<400> SEQUENCE: 133

Leu Val Ser Glu Lys Ser Arg Trp Leu Cys
1               5                   10

<210> SEQ ID NO 134
<211> LENGTH: 11
<212> TYPE: PRT
<213> ORGANISM: homo sapiens

<400> SEQUENCE: 134

Leu Val Ser Glu Lys Ser Arg Trp Leu Gly Cys
1               5                   10

<210> SEQ ID NO 135
<211> LENGTH: 9
<212> TYPE: PRT
<213> ORGANISM: homo sapiens

<400> SEQUENCE: 135

Leu Ala Thr Glu Arg Ser Arg Trp Ser
1               5

<210> SEQ ID NO 136
<211> LENGTH: 10
<212> TYPE: PRT
<213> ORGANISM: homo sapiens

<400> SEQUENCE: 136

Leu Ala Thr Glu Arg Ser Arg Trp Ser Gly
1               5                   10

<210> SEQ ID NO 137
<211> LENGTH: 10
```

```
<212> TYPE: PRT
<213> ORGANISM: homo sapiens

<400> SEQUENCE: 137

Cys Leu Ala Thr Glu Arg Ser Arg Trp Ser
1               5                   10

<210> SEQ ID NO 138
<211> LENGTH: 11
<212> TYPE: PRT
<213> ORGANISM: homo sapiens

<400> SEQUENCE: 138

Cys Leu Ala Thr Glu Arg Ser Arg Trp Ser Gly
1               5                   10

<210> SEQ ID NO 139
<211> LENGTH: 10
<212> TYPE: PRT
<213> ORGANISM: homo sapiens

<400> SEQUENCE: 139

Leu Ala Thr Glu Arg Ser Arg Trp Ser Cys
1               5                   10

<210> SEQ ID NO 140
<211> LENGTH: 11
<212> TYPE: PRT
<213> ORGANISM: homo sapiens

<400> SEQUENCE: 140

Leu Ala Thr Glu Arg Ser Arg Trp Ser Gly Cys
1               5                   10

<210> SEQ ID NO 141
<211> LENGTH: 9
<212> TYPE: PRT
<213> ORGANISM: homo sapiens

<400> SEQUENCE: 141

Leu Leu Thr Glu Arg Ser Arg Trp Ser
1               5

<210> SEQ ID NO 142
<211> LENGTH: 10
<212> TYPE: PRT
<213> ORGANISM: homo sapiens

<400> SEQUENCE: 142

Leu Leu Thr Glu Arg Ser Arg Trp Ser Gly
1               5                   10

<210> SEQ ID NO 143
<211> LENGTH: 10
<212> TYPE: PRT
<213> ORGANISM: homo sapiens

<400> SEQUENCE: 143

Cys Leu Leu Thr Glu Arg Ser Arg Trp Ser
1               5                   10

<210> SEQ ID NO 144
<211> LENGTH: 11
<212> TYPE: PRT
<213> ORGANISM: homo sapiens
```

<400> SEQUENCE: 144

Cys Leu Leu Thr Glu Arg Ser Arg Trp Ser Gly
1               5                   10

<210> SEQ ID NO 145
<211> LENGTH: 10
<212> TYPE: PRT
<213> ORGANISM: homo sapiens

<400> SEQUENCE: 145

Leu Leu Thr Glu Arg Ser Arg Trp Ser Cys
1               5                   10

<210> SEQ ID NO 146
<211> LENGTH: 11
<212> TYPE: PRT
<213> ORGANISM: homo sapiens

<400> SEQUENCE: 146

Leu Leu Thr Glu Arg Ser Arg Trp Ser Gly Cys
1               5                   10

<210> SEQ ID NO 147
<211> LENGTH: 9
<212> TYPE: PRT
<213> ORGANISM: homo sapiens

<400> SEQUENCE: 147

Leu Leu Thr Glu Arg Ser Arg Trp Ser
1               5

<210> SEQ ID NO 148
<211> LENGTH: 9
<212> TYPE: PRT
<213> ORGANISM: homo sapiens

<400> SEQUENCE: 148

Leu Val Thr Glu Arg Ser Arg Trp Ser
1               5

<210> SEQ ID NO 149
<211> LENGTH: 10
<212> TYPE: PRT
<213> ORGANISM: homo sapiens

<400> SEQUENCE: 149

Leu Val Thr Glu Arg Ser Arg Trp Ser Gly
1               5                   10

<210> SEQ ID NO 150
<211> LENGTH: 10
<212> TYPE: PRT
<213> ORGANISM: homo sapiens

<400> SEQUENCE: 150

Cys Leu Val Thr Glu Arg Ser Arg Trp Ser
1               5                   10

<210> SEQ ID NO 151
<211> LENGTH: 11
<212> TYPE: PRT
<213> ORGANISM: homo sapiens

<400> SEQUENCE: 151

```
Cys Leu Val Thr Glu Arg Ser Arg Trp Ser Gly
1               5                   10

<210> SEQ ID NO 152
<211> LENGTH: 10
<212> TYPE: PRT
<213> ORGANISM: homo sapiens

<400> SEQUENCE: 152

Leu Val Thr Glu Arg Ser Arg Trp Ser Cys
1               5                   10

<210> SEQ ID NO 153
<211> LENGTH: 11
<212> TYPE: PRT
<213> ORGANISM: homo sapiens

<400> SEQUENCE: 153

Leu Val Thr Glu Arg Ser Arg Trp Ser Gly Cys
1               5                   10

<210> SEQ ID NO 154
<211> LENGTH: 9
<212> TYPE: PRT
<213> ORGANISM: homo sapiens

<400> SEQUENCE: 154

Leu Met Thr Glu Arg Ser Arg Trp Ser
1               5

<210> SEQ ID NO 155
<211> LENGTH: 10
<212> TYPE: PRT
<213> ORGANISM: homo sapiens

<400> SEQUENCE: 155

Leu Met Thr Glu Arg Ser Arg Trp Ser Gly
1               5                   10

<210> SEQ ID NO 156
<211> LENGTH: 10
<212> TYPE: PRT
<213> ORGANISM: homo sapiens

<400> SEQUENCE: 156

Cys Leu Met Thr Glu Arg Ser Arg Trp Ser
1               5                   10

<210> SEQ ID NO 157
<211> LENGTH: 11
<212> TYPE: PRT
<213> ORGANISM: homo sapiens

<400> SEQUENCE: 157

Cys Leu Met Thr Glu Arg Ser Arg Trp Ser Gly
1               5                   10

<210> SEQ ID NO 158
<211> LENGTH: 10
<212> TYPE: PRT
<213> ORGANISM: homo sapiens

<400> SEQUENCE: 158

Leu Met Thr Glu Arg Ser Arg Trp Ser Cys
```

-continued

<210> SEQ ID NO 159
<211> LENGTH: 11
<212> TYPE: PRT
<213> ORGANISM: homo sapiens

<400> SEQUENCE: 159

Leu Met Thr Glu Arg Ser Arg Trp Ser Gly Cys
1               5                   10

<210> SEQ ID NO 160
<211> LENGTH: 9
<212> TYPE: PRT
<213> ORGANISM: homo sapiens

<400> SEQUENCE: 160

Leu Pro Thr Glu Arg Ser Arg Trp Ser
1               5

<210> SEQ ID NO 161
<211> LENGTH: 10
<212> TYPE: PRT
<213> ORGANISM: homo sapiens

<400> SEQUENCE: 161

Leu Pro Thr Glu Arg Ser Arg Trp Ser Gly
1               5                   10

<210> SEQ ID NO 162
<211> LENGTH: 10
<212> TYPE: PRT
<213> ORGANISM: homo sapiens

<400> SEQUENCE: 162

Cys Leu Pro Thr Glu Arg Ser Arg Trp Ser
1               5                   10

<210> SEQ ID NO 163
<211> LENGTH: 11
<212> TYPE: PRT
<213> ORGANISM: homo sapiens

<400> SEQUENCE: 163

Cys Leu Pro Thr Glu Arg Ser Arg Trp Ser Gly
1               5                   10

<210> SEQ ID NO 164
<211> LENGTH: 10
<212> TYPE: PRT
<213> ORGANISM: homo sapiens

<400> SEQUENCE: 164

Leu Pro Thr Glu Arg Ser Arg Trp Ser Cys
1               5                   10

<210> SEQ ID NO 165
<211> LENGTH: 11
<212> TYPE: PRT
<213> ORGANISM: homo sapiens

<400> SEQUENCE: 165

Leu Pro Thr Glu Arg Ser Arg Trp Ser Gly Cys
1               5                   10

<210> SEQ ID NO 166
<211> LENGTH: 9
<212> TYPE: PRT
<213> ORGANISM: homo sapiens

<400> SEQUENCE: 166

Leu Gly Thr Glu Arg Ser Arg Trp Ser
1               5

<210> SEQ ID NO 167
<211> LENGTH: 10
<212> TYPE: PRT
<213> ORGANISM: homo sapiens

<400> SEQUENCE: 167

Leu Gly Thr Glu Arg Ser Arg Trp Ser Gly
1               5                   10

<210> SEQ ID NO 168
<211> LENGTH: 10
<212> TYPE: PRT
<213> ORGANISM: homo sapiens

<400> SEQUENCE: 168

Cys Leu Gly Thr Glu Arg Ser Arg Trp Ser
1               5                   10

<210> SEQ ID NO 169
<211> LENGTH: 11
<212> TYPE: PRT
<213> ORGANISM: homo sapiens

<400> SEQUENCE: 169

Cys Leu Gly Thr Glu Arg Ser Arg Trp Ser Gly
1               5                   10

<210> SEQ ID NO 170
<211> LENGTH: 10
<212> TYPE: PRT
<213> ORGANISM: homo sapiens

<400> SEQUENCE: 170

Leu Gly Thr Glu Arg Ser Arg Trp Ser Cys
1               5                   10

<210> SEQ ID NO 171
<211> LENGTH: 11
<212> TYPE: PRT
<213> ORGANISM: homo sapiens

<400> SEQUENCE: 171

Leu Gly Thr Glu Arg Ser Arg Trp Ser Gly Cys
1               5                   10

<210> SEQ ID NO 172
<211> LENGTH: 9
<212> TYPE: PRT
<213> ORGANISM: homo sapiens

<400> SEQUENCE: 172

Leu Ala Thr Glu Arg Ser Arg Trp Leu
1               5

<210> SEQ ID NO 173

```
<211> LENGTH: 10
<212> TYPE: PRT
<213> ORGANISM: homo sapiens

<400> SEQUENCE: 173

Leu Ala Thr Glu Arg Ser Arg Trp Leu Gly
1               5                   10

<210> SEQ ID NO 174
<211> LENGTH: 10
<212> TYPE: PRT
<213> ORGANISM: homo sapiens

<400> SEQUENCE: 174

Cys Leu Ala Thr Glu Arg Ser Arg Trp Leu
1               5                   10

<210> SEQ ID NO 175
<211> LENGTH: 11
<212> TYPE: PRT
<213> ORGANISM: homo sapiens

<400> SEQUENCE: 175

Cys Leu Ala Thr Glu Arg Ser Arg Trp Leu Gly
1               5                   10

<210> SEQ ID NO 176
<211> LENGTH: 10
<212> TYPE: PRT
<213> ORGANISM: homo sapiens

<400> SEQUENCE: 176

Leu Ala Thr Glu Arg Ser Arg Trp Leu Cys
1               5                   10

<210> SEQ ID NO 177
<211> LENGTH: 11
<212> TYPE: PRT
<213> ORGANISM: homo sapiens

<400> SEQUENCE: 177

Leu Ala Thr Glu Arg Ser Arg Trp Leu Gly Cys
1               5                   10

<210> SEQ ID NO 178
<211> LENGTH: 9
<212> TYPE: PRT
<213> ORGANISM: homo sapiens

<400> SEQUENCE: 178

Leu Ala Thr Glu Arg Ser Arg Trp Val
1               5

<210> SEQ ID NO 179
<211> LENGTH: 10
<212> TYPE: PRT
<213> ORGANISM: homo sapiens

<400> SEQUENCE: 179

Leu Ala Thr Glu Arg Ser Arg Trp Val Gly
1               5                   10

<210> SEQ ID NO 180
<211> LENGTH: 10
<212> TYPE: PRT
```

<213> ORGANISM: homo sapiens

<400> SEQUENCE: 180

Cys Leu Ala Thr Glu Arg Ser Arg Trp Val
1               5                   10

<210> SEQ ID NO 181
<211> LENGTH: 11
<212> TYPE: PRT
<213> ORGANISM: homo sapiens

<400> SEQUENCE: 181

Cys Leu Ala Thr Glu Arg Ser Arg Trp Val Gly
1               5                   10

<210> SEQ ID NO 182
<211> LENGTH: 10
<212> TYPE: PRT
<213> ORGANISM: homo sapiens

<400> SEQUENCE: 182

Leu Ala Thr Glu Arg Ser Arg Trp Val Cys
1               5                   10

<210> SEQ ID NO 183
<211> LENGTH: 11
<212> TYPE: PRT
<213> ORGANISM: homo sapiens

<400> SEQUENCE: 183

Leu Ala Thr Glu Arg Ser Arg Trp Val Gly Cys
1               5                   10

<210> SEQ ID NO 184
<211> LENGTH: 9
<212> TYPE: PRT
<213> ORGANISM: homo sapiens

<400> SEQUENCE: 184

Leu Ala Thr Glu Arg Ser Arg Trp Thr
1               5

<210> SEQ ID NO 185
<211> LENGTH: 10
<212> TYPE: PRT
<213> ORGANISM: homo sapiens

<400> SEQUENCE: 185

Leu Ala Thr Glu Arg Ser Arg Trp Thr Gly
1               5                   10

<210> SEQ ID NO 186
<211> LENGTH: 10
<212> TYPE: PRT
<213> ORGANISM: homo sapiens

<400> SEQUENCE: 186

Cys Leu Ala Thr Glu Arg Ser Arg Trp Thr
1               5                   10

<210> SEQ ID NO 187
<211> LENGTH: 11
<212> TYPE: PRT
<213> ORGANISM: homo sapiens

```
<400> SEQUENCE: 187

Cys Leu Ala Thr Glu Arg Ser Arg Trp Thr Gly
1               5                   10

<210> SEQ ID NO 188
<211> LENGTH: 10
<212> TYPE: PRT
<213> ORGANISM: homo sapiens

<400> SEQUENCE: 188

Leu Ala Thr Glu Arg Ser Arg Trp Thr Cys
1               5                   10

<210> SEQ ID NO 189
<211> LENGTH: 11
<212> TYPE: PRT
<213> ORGANISM: homo sapiens

<400> SEQUENCE: 189

Leu Ala Thr Glu Arg Ser Arg Trp Thr Gly Cys
1               5                   10

<210> SEQ ID NO 190
<211> LENGTH: 9
<212> TYPE: PRT
<213> ORGANISM: homo sapiens

<400> SEQUENCE: 190

Leu Leu Thr Glu Arg Ser Arg Trp Val
1               5

<210> SEQ ID NO 191
<211> LENGTH: 10
<212> TYPE: PRT
<213> ORGANISM: homo sapiens

<400> SEQUENCE: 191

Leu Leu Thr Glu Arg Ser Arg Trp Val Gly
1               5                   10

<210> SEQ ID NO 192
<211> LENGTH: 10
<212> TYPE: PRT
<213> ORGANISM: homo sapiens

<400> SEQUENCE: 192

Cys Leu Leu Thr Glu Arg Ser Arg Trp Val
1               5                   10

<210> SEQ ID NO 193
<211> LENGTH: 11
<212> TYPE: PRT
<213> ORGANISM: homo sapiens

<400> SEQUENCE: 193

Cys Leu Leu Thr Glu Arg Ser Arg Trp Val Gly
1               5                   10

<210> SEQ ID NO 194
<211> LENGTH: 10
<212> TYPE: PRT
<213> ORGANISM: homo sapiens

<400> SEQUENCE: 194
```

-continued

Leu Leu Thr Glu Arg Ser Arg Trp Val Cys
1               5                   10

<210> SEQ ID NO 195
<211> LENGTH: 11
<212> TYPE: PRT
<213> ORGANISM: homo sapiens

<400> SEQUENCE: 195

Leu Leu Thr Glu Arg Ser Arg Trp Val Gly Cys
1               5                   10

<210> SEQ ID NO 196
<211> LENGTH: 9
<212> TYPE: PRT
<213> ORGANISM: homo sapiens

<400> SEQUENCE: 196

Leu Val Thr Glu Arg Ser Arg Trp Leu
1               5

<210> SEQ ID NO 197
<211> LENGTH: 10
<212> TYPE: PRT
<213> ORGANISM: homo sapiens

<400> SEQUENCE: 197

Leu Val Thr Glu Arg Ser Arg Trp Leu Gly
1               5                   10

<210> SEQ ID NO 198
<211> LENGTH: 10
<212> TYPE: PRT
<213> ORGANISM: homo sapiens

<400> SEQUENCE: 198

Cys Leu Val Thr Glu Arg Ser Arg Trp Leu
1               5                   10

<210> SEQ ID NO 199
<211> LENGTH: 11
<212> TYPE: PRT
<213> ORGANISM: homo sapiens

<400> SEQUENCE: 199

Cys Leu Val Thr Glu Arg Ser Arg Trp Leu Gly
1               5                   10

<210> SEQ ID NO 200
<211> LENGTH: 10
<212> TYPE: PRT
<213> ORGANISM: homo sapiens

<400> SEQUENCE: 200

Leu Val Thr Glu Arg Ser Arg Trp Leu Cys
1               5                   10

<210> SEQ ID NO 201
<211> LENGTH: 11
<212> TYPE: PRT
<213> ORGANISM: homo sapiens

<400> SEQUENCE: 201

Leu Val Thr Glu Arg Ser Arg Trp Leu Gly Cys
1               5                   10

<210> SEQ ID NO 202
<211> LENGTH: 9
<212> TYPE: PRT
<213> ORGANISM: homo sapiens

<400> SEQUENCE: 202

Leu Ala Thr Glu His Ser Arg Trp Ser
1               5

<210> SEQ ID NO 203
<211> LENGTH: 10
<212> TYPE: PRT
<213> ORGANISM: homo sapiens

<400> SEQUENCE: 203

Leu Ala Thr Glu His Ser Arg Trp Ser Gly
1               5                   10

<210> SEQ ID NO 204
<211> LENGTH: 10
<212> TYPE: PRT
<213> ORGANISM: homo sapiens

<400> SEQUENCE: 204

Cys Leu Ala Thr Glu His Ser Arg Trp Ser
1               5                   10

<210> SEQ ID NO 205
<211> LENGTH: 11
<212> TYPE: PRT
<213> ORGANISM: homo sapiens

<400> SEQUENCE: 205

Cys Leu Ala Thr Glu His Ser Arg Trp Ser Gly
1               5                   10

<210> SEQ ID NO 206
<211> LENGTH: 10
<212> TYPE: PRT
<213> ORGANISM: homo sapiens

<400> SEQUENCE: 206

Leu Ala Thr Glu His Ser Arg Trp Ser Cys
1               5                   10

<210> SEQ ID NO 207
<211> LENGTH: 11
<212> TYPE: PRT
<213> ORGANISM: homo sapiens

<400> SEQUENCE: 207

Leu Ala Thr Glu His Ser Arg Trp Ser Gly Cys
1               5                   10

<210> SEQ ID NO 208
<211> LENGTH: 9
<212> TYPE: PRT
<213> ORGANISM: homo sapiens

<400> SEQUENCE: 208

Leu Leu Thr Glu His Ser Arg Trp Ser
1               5

```
<210> SEQ ID NO 209
<211> LENGTH: 10
<212> TYPE: PRT
<213> ORGANISM: homo sapiens

<400> SEQUENCE: 209

Leu Leu Thr Glu His Ser Arg Trp Ser Gly
1               5                   10

<210> SEQ ID NO 210
<211> LENGTH: 10
<212> TYPE: PRT
<213> ORGANISM: homo sapiens

<400> SEQUENCE: 210

Cys Leu Leu Thr Glu His Ser Arg Trp Ser
1               5                   10

<210> SEQ ID NO 211
<211> LENGTH: 11
<212> TYPE: PRT
<213> ORGANISM: homo sapiens

<400> SEQUENCE: 211

Cys Leu Leu Thr Glu His Ser Arg Trp Ser Gly
1               5                   10

<210> SEQ ID NO 212
<211> LENGTH: 10
<212> TYPE: PRT
<213> ORGANISM: homo sapiens

<400> SEQUENCE: 212

Leu Leu Thr Glu His Ser Arg Trp Ser Cys
1               5                   10

<210> SEQ ID NO 213
<211> LENGTH: 11
<212> TYPE: PRT
<213> ORGANISM: homo sapiens

<400> SEQUENCE: 213

Leu Leu Thr Glu His Ser Arg Trp Ser Gly Cys
1               5                   10

<210> SEQ ID NO 214
<211> LENGTH: 9
<212> TYPE: PRT
<213> ORGANISM: homo sapiens

<400> SEQUENCE: 214

Leu Leu Thr Glu His Ser Arg Trp Ser
1               5

<210> SEQ ID NO 215
<211> LENGTH: 9
<212> TYPE: PRT
<213> ORGANISM: homo sapiens

<400> SEQUENCE: 215

Leu Val Thr Glu His Ser Arg Trp Ser
1               5

<210> SEQ ID NO 216
<211> LENGTH: 10
```

```
<212> TYPE: PRT
<213> ORGANISM: homo sapiens

<400> SEQUENCE: 216

Leu Val Thr Glu His Ser Arg Trp Ser Gly
1               5                   10

<210> SEQ ID NO 217
<211> LENGTH: 10
<212> TYPE: PRT
<213> ORGANISM: homo sapiens

<400> SEQUENCE: 217

Cys Leu Val Thr Glu His Ser Arg Trp Ser
1               5                   10

<210> SEQ ID NO 218
<211> LENGTH: 11
<212> TYPE: PRT
<213> ORGANISM: homo sapiens

<400> SEQUENCE: 218

Cys Leu Val Thr Glu His Ser Arg Trp Ser Gly
1               5                   10

<210> SEQ ID NO 219
<211> LENGTH: 10
<212> TYPE: PRT
<213> ORGANISM: homo sapiens

<400> SEQUENCE: 219

Leu Val Thr Glu His Ser Arg Trp Ser Cys
1               5                   10

<210> SEQ ID NO 220
<211> LENGTH: 11
<212> TYPE: PRT
<213> ORGANISM: homo sapiens

<400> SEQUENCE: 220

Leu Val Thr Glu His Ser Arg Trp Ser Gly Cys
1               5                   10

<210> SEQ ID NO 221
<211> LENGTH: 9
<212> TYPE: PRT
<213> ORGANISM: homo sapiens

<400> SEQUENCE: 221

Leu Met Thr Glu His Ser Arg Trp Ser
1               5

<210> SEQ ID NO 222
<211> LENGTH: 10
<212> TYPE: PRT
<213> ORGANISM: homo sapiens

<400> SEQUENCE: 222

Leu Met Thr Glu His Ser Arg Trp Ser Gly
1               5                   10

<210> SEQ ID NO 223
<211> LENGTH: 10
<212> TYPE: PRT
<213> ORGANISM: homo sapiens
```

-continued

<400> SEQUENCE: 223

Cys Leu Met Thr Glu His Ser Arg Trp Ser
1               5                   10

<210> SEQ ID NO 224
<211> LENGTH: 11
<212> TYPE: PRT
<213> ORGANISM: homo sapiens

<400> SEQUENCE: 224

Cys Leu Met Thr Glu His Ser Arg Trp Ser Gly
1               5                   10

<210> SEQ ID NO 225
<211> LENGTH: 10
<212> TYPE: PRT
<213> ORGANISM: homo sapiens

<400> SEQUENCE: 225

Leu Met Thr Glu His Ser Arg Trp Ser Cys
1               5                   10

<210> SEQ ID NO 226
<211> LENGTH: 11
<212> TYPE: PRT
<213> ORGANISM: homo sapiens

<400> SEQUENCE: 226

Leu Met Thr Glu His Ser Arg Trp Ser Gly Cys
1               5                   10

<210> SEQ ID NO 227
<211> LENGTH: 9
<212> TYPE: PRT
<213> ORGANISM: homo sapiens

<400> SEQUENCE: 227

Leu Pro Thr Glu His Ser Arg Trp Ser
1               5

<210> SEQ ID NO 228
<211> LENGTH: 10
<212> TYPE: PRT
<213> ORGANISM: homo sapiens

<400> SEQUENCE: 228

Leu Pro Thr Glu His Ser Arg Trp Ser Gly
1               5                   10

<210> SEQ ID NO 229
<211> LENGTH: 10
<212> TYPE: PRT
<213> ORGANISM: homo sapiens

<400> SEQUENCE: 229

Cys Leu Pro Thr Glu His Ser Arg Trp Ser
1               5                   10

<210> SEQ ID NO 230
<211> LENGTH: 11
<212> TYPE: PRT
<213> ORGANISM: homo sapiens

<400> SEQUENCE: 230

```
Cys Leu Pro Thr Glu His Ser Arg Trp Ser Gly
 1               5                  10
```

<210> SEQ ID NO 231
<211> LENGTH: 10
<212> TYPE: PRT
<213> ORGANISM: homo sapiens

<400> SEQUENCE: 231

```
Leu Pro Thr Glu His Ser Arg Trp Ser Cys
 1               5                  10
```

<210> SEQ ID NO 232
<211> LENGTH: 11
<212> TYPE: PRT
<213> ORGANISM: homo sapiens

<400> SEQUENCE: 232

```
Leu Pro Thr Glu His Ser Arg Trp Ser Gly Cys
 1               5                  10
```

<210> SEQ ID NO 233
<211> LENGTH: 9
<212> TYPE: PRT
<213> ORGANISM: homo sapiens

<400> SEQUENCE: 233

```
Leu Gly Thr Glu His Ser Arg Trp Ser
 1               5
```

<210> SEQ ID NO 234
<211> LENGTH: 10
<212> TYPE: PRT
<213> ORGANISM: homo sapiens

<400> SEQUENCE: 234

```
Leu Gly Thr Glu His Ser Arg Trp Ser Gly
 1               5                  10
```

<210> SEQ ID NO 235
<211> LENGTH: 10
<212> TYPE: PRT
<213> ORGANISM: homo sapiens

<400> SEQUENCE: 235

```
Cys Leu Gly Thr Glu His Ser Arg Trp Ser
 1               5                  10
```

<210> SEQ ID NO 236
<211> LENGTH: 11
<212> TYPE: PRT
<213> ORGANISM: homo sapiens

<400> SEQUENCE: 236

```
Cys Leu Gly Thr Glu His Ser Arg Trp Ser Gly
 1               5                  10
```

<210> SEQ ID NO 237
<211> LENGTH: 10
<212> TYPE: PRT
<213> ORGANISM: homo sapiens

<400> SEQUENCE: 237

```
Leu Gly Thr Glu His Ser Arg Trp Ser Cys
```

```
1               5                  10

<210> SEQ ID NO 238
<211> LENGTH: 11
<212> TYPE: PRT
<213> ORGANISM: homo sapiens

<400> SEQUENCE: 238

Leu Gly Thr Glu His Ser Arg Trp Ser Gly Cys
1               5                  10

<210> SEQ ID NO 239
<211> LENGTH: 9
<212> TYPE: PRT
<213> ORGANISM: homo sapiens

<400> SEQUENCE: 239

Leu Ala Thr Glu His Ser Arg Trp Leu
1               5

<210> SEQ ID NO 240
<211> LENGTH: 10
<212> TYPE: PRT
<213> ORGANISM: homo sapiens

<400> SEQUENCE: 240

Leu Ala Thr Glu His Ser Arg Trp Leu Gly
1               5                  10

<210> SEQ ID NO 241
<211> LENGTH: 10
<212> TYPE: PRT
<213> ORGANISM: homo sapiens

<400> SEQUENCE: 241

Cys Leu Ala Thr Glu His Ser Arg Trp Leu
1               5                  10

<210> SEQ ID NO 242
<211> LENGTH: 11
<212> TYPE: PRT
<213> ORGANISM: homo sapiens

<400> SEQUENCE: 242

Cys Leu Ala Thr Glu His Ser Arg Trp Leu Gly
1               5                  10

<210> SEQ ID NO 243
<211> LENGTH: 10
<212> TYPE: PRT
<213> ORGANISM: homo sapiens

<400> SEQUENCE: 243

Leu Ala Thr Glu His Ser Arg Trp Leu Cys
1               5                  10

<210> SEQ ID NO 244
<211> LENGTH: 11
<212> TYPE: PRT
<213> ORGANISM: homo sapiens

<400> SEQUENCE: 244

Leu Ala Thr Glu His Ser Arg Trp Leu Gly Cys
1               5                  10
```

```
<210> SEQ ID NO 245
<211> LENGTH: 9
<212> TYPE: PRT
<213> ORGANISM: homo sapiens

<400> SEQUENCE: 245

Leu Ala Thr Glu His Ser Arg Trp Val
1               5

<210> SEQ ID NO 246
<211> LENGTH: 10
<212> TYPE: PRT
<213> ORGANISM: homo sapiens

<400> SEQUENCE: 246

Leu Ala Thr Glu His Ser Arg Trp Val Gly
1               5                   10

<210> SEQ ID NO 247
<211> LENGTH: 10
<212> TYPE: PRT
<213> ORGANISM: homo sapiens

<400> SEQUENCE: 247

Cys Leu Ala Thr Glu His Ser Arg Trp Val
1               5                   10

<210> SEQ ID NO 248
<211> LENGTH: 11
<212> TYPE: PRT
<213> ORGANISM: homo sapiens

<400> SEQUENCE: 248

Cys Leu Ala Thr Glu His Ser Arg Trp Val Gly
1               5                   10

<210> SEQ ID NO 249
<211> LENGTH: 10
<212> TYPE: PRT
<213> ORGANISM: homo sapiens

<400> SEQUENCE: 249

Leu Ala Thr Glu His Ser Arg Trp Val Cys
1               5                   10

<210> SEQ ID NO 250
<211> LENGTH: 11
<212> TYPE: PRT
<213> ORGANISM: homo sapiens

<400> SEQUENCE: 250

Leu Ala Thr Glu His Ser Arg Trp Val Gly Cys
1               5                   10

<210> SEQ ID NO 251
<211> LENGTH: 9
<212> TYPE: PRT
<213> ORGANISM: homo sapiens

<400> SEQUENCE: 251

Leu Ala Thr Glu His Ser Arg Trp Thr
1               5

<210> SEQ ID NO 252
```

```
<211> LENGTH: 10
<212> TYPE: PRT
<213> ORGANISM: homo sapiens

<400> SEQUENCE: 252

Leu Ala Thr Glu His Ser Arg Trp Thr Gly
1               5                   10

<210> SEQ ID NO 253
<211> LENGTH: 10
<212> TYPE: PRT
<213> ORGANISM: homo sapiens

<400> SEQUENCE: 253

Cys Leu Ala Thr Glu His Ser Arg Trp Thr
1               5                   10

<210> SEQ ID NO 254
<211> LENGTH: 11
<212> TYPE: PRT
<213> ORGANISM: homo sapiens

<400> SEQUENCE: 254

Cys Leu Ala Thr Glu His Ser Arg Trp Thr Gly
1               5                   10

<210> SEQ ID NO 255
<211> LENGTH: 10
<212> TYPE: PRT
<213> ORGANISM: homo sapiens

<400> SEQUENCE: 255

Leu Ala Thr Glu His Ser Arg Trp Thr Cys
1               5                   10

<210> SEQ ID NO 256
<211> LENGTH: 11
<212> TYPE: PRT
<213> ORGANISM: homo sapiens

<400> SEQUENCE: 256

Leu Ala Thr Glu His Ser Arg Trp Thr Gly Cys
1               5                   10

<210> SEQ ID NO 257
<211> LENGTH: 9
<212> TYPE: PRT
<213> ORGANISM: homo sapiens

<400> SEQUENCE: 257

Leu Leu Thr Glu His Ser Arg Trp Val
1               5

<210> SEQ ID NO 258
<211> LENGTH: 10
<212> TYPE: PRT
<213> ORGANISM: homo sapiens

<400> SEQUENCE: 258

Leu Leu Thr Glu His Ser Arg Trp Val Gly
1               5                   10

<210> SEQ ID NO 259
<211> LENGTH: 10
<212> TYPE: PRT
```

<213> ORGANISM: homo sapiens

<400> SEQUENCE: 259

Cys Leu Leu Thr Glu His Ser Arg Trp Val
1               5                   10

<210> SEQ ID NO 260
<211> LENGTH: 11
<212> TYPE: PRT
<213> ORGANISM: homo sapiens

<400> SEQUENCE: 260

Cys Leu Leu Thr Glu His Ser Arg Trp Val Gly
1               5                   10

<210> SEQ ID NO 261
<211> LENGTH: 10
<212> TYPE: PRT
<213> ORGANISM: homo sapiens

<400> SEQUENCE: 261

Leu Leu Thr Glu His Ser Arg Trp Val Cys
1               5                   10

<210> SEQ ID NO 262
<211> LENGTH: 11
<212> TYPE: PRT
<213> ORGANISM: homo sapiens

<400> SEQUENCE: 262

Leu Leu Thr Glu His Ser Arg Trp Val Gly Cys
1               5                   10

<210> SEQ ID NO 263
<211> LENGTH: 9
<212> TYPE: PRT
<213> ORGANISM: homo sapiens

<400> SEQUENCE: 263

Leu Val Thr Glu His Ser Arg Trp Leu
1               5

<210> SEQ ID NO 264
<211> LENGTH: 10
<212> TYPE: PRT
<213> ORGANISM: homo sapiens

<400> SEQUENCE: 264

Leu Val Thr Glu His Ser Arg Trp Leu Gly
1               5                   10

<210> SEQ ID NO 265
<211> LENGTH: 10
<212> TYPE: PRT
<213> ORGANISM: homo sapiens

<400> SEQUENCE: 265

Cys Leu Val Thr Glu His Ser Arg Trp Leu
1               5                   10

<210> SEQ ID NO 266
<211> LENGTH: 11
<212> TYPE: PRT
<213> ORGANISM: homo sapiens

<400> SEQUENCE: 266

Cys Leu Val Thr Glu His Ser Arg Trp Leu Gly
1               5                   10

<210> SEQ ID NO 267
<211> LENGTH: 10
<212> TYPE: PRT
<213> ORGANISM: homo sapiens

<400> SEQUENCE: 267

Leu Val Thr Glu His Ser Arg Trp Leu Cys
1               5                   10

<210> SEQ ID NO 268
<211> LENGTH: 11
<212> TYPE: PRT
<213> ORGANISM: homo sapiens

<400> SEQUENCE: 268

Leu Val Thr Glu His Ser Arg Trp Leu Gly Cys
1               5                   10

<210> SEQ ID NO 269
<211> LENGTH: 9
<212> TYPE: PRT
<213> ORGANISM: homo sapiens

<400> SEQUENCE: 269

Leu Ala Thr Glu Lys Thr Arg Trp Ser
1               5

<210> SEQ ID NO 270
<211> LENGTH: 10
<212> TYPE: PRT
<213> ORGANISM: homo sapiens

<400> SEQUENCE: 270

Leu Ala Thr Glu Lys Thr Arg Trp Ser Gly
1               5                   10

<210> SEQ ID NO 271
<211> LENGTH: 10
<212> TYPE: PRT
<213> ORGANISM: homo sapiens

<400> SEQUENCE: 271

Cys Leu Ala Thr Glu Lys Thr Arg Trp Ser
1               5                   10

<210> SEQ ID NO 272
<211> LENGTH: 11
<212> TYPE: PRT
<213> ORGANISM: homo sapiens

<400> SEQUENCE: 272

Cys Leu Ala Thr Glu Lys Thr Arg Trp Ser Gly
1               5                   10

<210> SEQ ID NO 273
<211> LENGTH: 10
<212> TYPE: PRT
<213> ORGANISM: homo sapiens

<400> SEQUENCE: 273

Leu Ala Thr Glu Lys Thr Arg Trp Ser Cys
1               5                   10

<210> SEQ ID NO 274
<211> LENGTH: 11
<212> TYPE: PRT
<213> ORGANISM: homo sapiens

<400> SEQUENCE: 274

Leu Ala Thr Glu Lys Thr Arg Trp Ser Gly Cys
1               5                   10

<210> SEQ ID NO 275
<211> LENGTH: 9
<212> TYPE: PRT
<213> ORGANISM: homo sapiens

<400> SEQUENCE: 275

Leu Leu Thr Glu Lys Thr Arg Trp Ser
1               5

<210> SEQ ID NO 276
<211> LENGTH: 10
<212> TYPE: PRT
<213> ORGANISM: homo sapiens

<400> SEQUENCE: 276

Leu Leu Thr Glu Lys Thr Arg Trp Ser Gly
1               5                   10

<210> SEQ ID NO 277
<211> LENGTH: 10
<212> TYPE: PRT
<213> ORGANISM: homo sapiens

<400> SEQUENCE: 277

Cys Leu Leu Thr Glu Lys Thr Arg Trp Ser
1               5                   10

<210> SEQ ID NO 278
<211> LENGTH: 11
<212> TYPE: PRT
<213> ORGANISM: homo sapiens

<400> SEQUENCE: 278

Cys Leu Leu Thr Glu Lys Thr Arg Trp Ser Gly
1               5                   10

<210> SEQ ID NO 279
<211> LENGTH: 10
<212> TYPE: PRT
<213> ORGANISM: homo sapiens

<400> SEQUENCE: 279

Leu Leu Thr Glu Lys Thr Arg Trp Ser Cys
1               5                   10

<210> SEQ ID NO 280
<211> LENGTH: 11
<212> TYPE: PRT
<213> ORGANISM: homo sapiens

<400> SEQUENCE: 280

Leu Leu Thr Glu Lys Thr Arg Trp Ser Gly Cys
1               5                   10

<210> SEQ ID NO 281
<211> LENGTH: 9
<212> TYPE: PRT
<213> ORGANISM: homo sapiens

<400> SEQUENCE: 281

Leu Leu Thr Glu Lys Thr Arg Trp Ser
1               5

<210> SEQ ID NO 282
<211> LENGTH: 9
<212> TYPE: PRT
<213> ORGANISM: homo sapiens

<400> SEQUENCE: 282

Leu Val Thr Glu Lys Thr Arg Trp Ser
1               5

<210> SEQ ID NO 283
<211> LENGTH: 10
<212> TYPE: PRT
<213> ORGANISM: homo sapiens

<400> SEQUENCE: 283

Leu Val Thr Glu Lys Thr Arg Trp Ser Gly
1               5                   10

<210> SEQ ID NO 284
<211> LENGTH: 10
<212> TYPE: PRT
<213> ORGANISM: homo sapiens

<400> SEQUENCE: 284

Cys Leu Val Thr Glu Lys Thr Arg Trp Ser
1               5                   10

<210> SEQ ID NO 285
<211> LENGTH: 11
<212> TYPE: PRT
<213> ORGANISM: homo sapiens

<400> SEQUENCE: 285

Cys Leu Val Thr Glu Lys Thr Arg Trp Ser Gly
1               5                   10

<210> SEQ ID NO 286
<211> LENGTH: 10
<212> TYPE: PRT
<213> ORGANISM: homo sapiens

<400> SEQUENCE: 286

Leu Val Thr Glu Lys Thr Arg Trp Ser Cys
1               5                   10

<210> SEQ ID NO 287
<211> LENGTH: 11
<212> TYPE: PRT
<213> ORGANISM: homo sapiens

<400> SEQUENCE: 287

Leu Val Thr Glu Leu Thr Arg Trp Ser Gly Cys
1               5                   10

```
<210> SEQ ID NO 288
<211> LENGTH: 9
<212> TYPE: PRT
<213> ORGANISM: homo sapiens

<400> SEQUENCE: 288

Leu Met Thr Glu Lys Thr Arg Trp Ser
1               5

<210> SEQ ID NO 289
<211> LENGTH: 10
<212> TYPE: PRT
<213> ORGANISM: homo sapiens

<400> SEQUENCE: 289

Leu Met Thr Glu Lys Thr Arg Trp Ser Gly
1               5                   10

<210> SEQ ID NO 290
<211> LENGTH: 10
<212> TYPE: PRT
<213> ORGANISM: homo sapiens

<400> SEQUENCE: 290

Cys Leu Met Thr Glu Lys Thr Arg Trp Ser
1               5                   10

<210> SEQ ID NO 291
<211> LENGTH: 11
<212> TYPE: PRT
<213> ORGANISM: homo sapiens

<400> SEQUENCE: 291

Cys Leu Met Thr Glu Lys Thr Arg Trp Ser Gly
1               5                   10

<210> SEQ ID NO 292
<211> LENGTH: 10
<212> TYPE: PRT
<213> ORGANISM: homo sapiens

<400> SEQUENCE: 292

Leu Met Thr Glu Lys Thr Arg Trp Ser Cys
1               5                   10

<210> SEQ ID NO 293
<211> LENGTH: 11
<212> TYPE: PRT
<213> ORGANISM: homo sapiens

<400> SEQUENCE: 293

Leu Met Thr Glu Lys Thr Arg Trp Ser Gly Cys
1               5                   10

<210> SEQ ID NO 294
<211> LENGTH: 9
<212> TYPE: PRT
<213> ORGANISM: homo sapiens

<400> SEQUENCE: 294

Leu Pro Thr Glu Lys Thr Arg Trp Ser
1               5

<210> SEQ ID NO 295
<211> LENGTH: 10
```

```
<212> TYPE: PRT
<213> ORGANISM: homo sapiens

<400> SEQUENCE: 295

Leu Pro Thr Glu Lys Thr Arg Trp Ser Gly
1               5                   10

<210> SEQ ID NO 296
<211> LENGTH: 10
<212> TYPE: PRT
<213> ORGANISM: homo sapiens

<400> SEQUENCE: 296

Cys Leu Pro Thr Glu Leu Thr Arg Trp Ser
1               5                   10

<210> SEQ ID NO 297
<211> LENGTH: 11
<212> TYPE: PRT
<213> ORGANISM: homo sapiens

<400> SEQUENCE: 297

Cys Leu Pro Thr Glu Lys Thr Arg Trp Ser Gly
1               5                   10

<210> SEQ ID NO 298
<211> LENGTH: 10
<212> TYPE: PRT
<213> ORGANISM: homo sapiens

<400> SEQUENCE: 298

Leu Pro Thr Glu Lys Thr Arg Trp Ser Cys
1               5                   10

<210> SEQ ID NO 299
<211> LENGTH: 11
<212> TYPE: PRT
<213> ORGANISM: homo sapiens

<400> SEQUENCE: 299

Leu Pro Thr Glu Lys Thr Arg Trp Ser Gly Cys
1               5                   10

<210> SEQ ID NO 300
<211> LENGTH: 9
<212> TYPE: PRT
<213> ORGANISM: homo sapiens

<400> SEQUENCE: 300

Leu Gly Thr Glu Lys Thr Arg Trp Ser
1               5

<210> SEQ ID NO 301
<211> LENGTH: 10
<212> TYPE: PRT
<213> ORGANISM: homo sapiens

<400> SEQUENCE: 301

Leu Gly Thr Glu Lys Thr Arg Trp Ser Gly
1               5                   10

<210> SEQ ID NO 302
<211> LENGTH: 10
<212> TYPE: PRT
<213> ORGANISM: homo sapiens
```

-continued

<400> SEQUENCE: 302

Cys Leu Gly Thr Glu Lys Thr Arg Trp Ser
1               5                   10

<210> SEQ ID NO 303
<211> LENGTH: 11
<212> TYPE: PRT
<213> ORGANISM: homo sapiens

<400> SEQUENCE: 303

Cys Leu Gly Thr Glu Lys Thr Arg Trp Ser Gly
1               5                   10

<210> SEQ ID NO 304
<211> LENGTH: 10
<212> TYPE: PRT
<213> ORGANISM: homo sapiens

<400> SEQUENCE: 304

Leu Gly Thr Glu Lys Thr Arg Trp Ser Cys
1               5                   10

<210> SEQ ID NO 305
<211> LENGTH: 11
<212> TYPE: PRT
<213> ORGANISM: homo sapiens

<400> SEQUENCE: 305

Leu Gly Thr Glu Lys Thr Arg Trp Ser Gly Cys
1               5                   10

<210> SEQ ID NO 306
<211> LENGTH: 9
<212> TYPE: PRT
<213> ORGANISM: homo sapiens

<400> SEQUENCE: 306

Leu Ala Thr Glu Lys Thr Arg Trp Leu
1               5

<210> SEQ ID NO 307
<211> LENGTH: 10
<212> TYPE: PRT
<213> ORGANISM: homo sapiens

<400> SEQUENCE: 307

Leu Ala Thr Glu Lys Thr Arg Trp Leu Gly
1               5                   10

<210> SEQ ID NO 308
<211> LENGTH: 10
<212> TYPE: PRT
<213> ORGANISM: homo sapiens

<400> SEQUENCE: 308

Cys Leu Ala Thr Glu Lys Thr Arg Trp Leu
1               5                   10

<210> SEQ ID NO 309
<211> LENGTH: 11
<212> TYPE: PRT
<213> ORGANISM: homo sapiens

<400> SEQUENCE: 309

Cys Leu Ala Thr Glu Lys Thr Arg Trp Leu Gly
1               5                   10

<210> SEQ ID NO 310
<211> LENGTH: 10
<212> TYPE: PRT
<213> ORGANISM: homo sapiens

<400> SEQUENCE: 310

Leu Ala Thr Glu Lys Thr Arg Trp Leu Cys
1               5                   10

<210> SEQ ID NO 311
<211> LENGTH: 11
<212> TYPE: PRT
<213> ORGANISM: homo sapiens

<400> SEQUENCE: 311

Leu Ala Thr Glu Lys Thr Arg Trp Leu Gly Cys
1               5                   10

<210> SEQ ID NO 312
<211> LENGTH: 9
<212> TYPE: PRT
<213> ORGANISM: homo sapiens

<400> SEQUENCE: 312

Leu Ala Thr Glu Lys Thr Arg Trp Val
1               5

<210> SEQ ID NO 313
<211> LENGTH: 10
<212> TYPE: PRT
<213> ORGANISM: homo sapiens

<400> SEQUENCE: 313

Leu Ala Thr Glu Lys Thr Arg Trp Val Gly
1               5                   10

<210> SEQ ID NO 314
<211> LENGTH: 10
<212> TYPE: PRT
<213> ORGANISM: homo sapiens

<400> SEQUENCE: 314

Cys Leu Ala Thr Glu Lys Thr Arg Trp Val
1               5                   10

<210> SEQ ID NO 315
<211> LENGTH: 11
<212> TYPE: PRT
<213> ORGANISM: homo sapiens

<400> SEQUENCE: 315

Cys Leu Ala Thr Glu Lys Thr Arg Trp Val Gly
1               5                   10

<210> SEQ ID NO 316
<211> LENGTH: 10
<212> TYPE: PRT
<213> ORGANISM: homo sapiens

<400> SEQUENCE: 316

Leu Ala Thr Glu Lys Thr Arg Trp Val Cys

```
1               5                   10

<210> SEQ ID NO 317
<211> LENGTH: 11
<212> TYPE: PRT
<213> ORGANISM: homo sapiens

<400> SEQUENCE: 317

Leu Ala Thr Glu Lys Thr Arg Trp Val Gly Cys
1               5                   10

<210> SEQ ID NO 318
<211> LENGTH: 9
<212> TYPE: PRT
<213> ORGANISM: homo sapiens

<400> SEQUENCE: 318

Leu Ala Thr Glu Lys Thr Arg Trp Thr
1               5

<210> SEQ ID NO 319
<211> LENGTH: 10
<212> TYPE: PRT
<213> ORGANISM: homo sapiens

<400> SEQUENCE: 319

Leu Ala Thr Glu Lys Thr Arg Trp Thr Gly
1               5                   10

<210> SEQ ID NO 320
<211> LENGTH: 10
<212> TYPE: PRT
<213> ORGANISM: homo sapiens

<400> SEQUENCE: 320

Cys Leu Ala Thr Glu Lys Thr Arg Trp Thr
1               5                   10

<210> SEQ ID NO 321
<211> LENGTH: 11
<212> TYPE: PRT
<213> ORGANISM: homo sapiens

<400> SEQUENCE: 321

Cys Leu Ala Thr Glu Lys Thr Arg Trp Thr Gly
1               5                   10

<210> SEQ ID NO 322
<211> LENGTH: 10
<212> TYPE: PRT
<213> ORGANISM: homo sapiens

<400> SEQUENCE: 322

Leu Ala Thr Glu Lys Thr Arg Trp Thr Cys
1               5                   10

<210> SEQ ID NO 323
<211> LENGTH: 11
<212> TYPE: PRT
<213> ORGANISM: homo sapiens

<400> SEQUENCE: 323

Leu Ala Thr Glu Lys Thr Arg Trp Thr Gly Cys
1               5                   10
```

```
<210> SEQ ID NO 324
<211> LENGTH: 9
<212> TYPE: PRT
<213> ORGANISM: homo sapiens

<400> SEQUENCE: 324

Leu Leu Thr Glu Lys Thr Arg Trp Val
1               5

<210> SEQ ID NO 325
<211> LENGTH: 10
<212> TYPE: PRT
<213> ORGANISM: homo sapiens

<400> SEQUENCE: 325

Leu Leu Thr Glu Lys Thr Arg Trp Val Gly
1               5                   10

<210> SEQ ID NO 326
<211> LENGTH: 10
<212> TYPE: PRT
<213> ORGANISM: homo sapiens

<400> SEQUENCE: 326

Cys Leu Leu Thr Glu Lys Thr Arg Trp Val
1               5                   10

<210> SEQ ID NO 327
<211> LENGTH: 11
<212> TYPE: PRT
<213> ORGANISM: homo sapiens

<400> SEQUENCE: 327

Cys Leu Leu Thr Glu Lys Thr Arg Trp Val Gly
1               5                   10

<210> SEQ ID NO 328
<211> LENGTH: 10
<212> TYPE: PRT
<213> ORGANISM: homo sapiens

<400> SEQUENCE: 328

Leu Leu Thr Glu Lys Thr Arg Trp Val Cys
1               5                   10

<210> SEQ ID NO 329
<211> LENGTH: 11
<212> TYPE: PRT
<213> ORGANISM: homo sapiens

<400> SEQUENCE: 329

Leu Leu Thr Glu Lys Thr Arg Trp Val Gly Cys
1               5                   10

<210> SEQ ID NO 330
<211> LENGTH: 9
<212> TYPE: PRT
<213> ORGANISM: homo sapiens

<400> SEQUENCE: 330

Leu Val Thr Glu Lys Thr Arg Trp Leu
1               5

<210> SEQ ID NO 331
```

```
<211> LENGTH: 10
<212> TYPE: PRT
<213> ORGANISM: homo sapiens

<400> SEQUENCE: 331

Leu Val Thr Glu Lys Thr Arg Trp Leu Gly
1               5                   10

<210> SEQ ID NO 332
<211> LENGTH: 10
<212> TYPE: PRT
<213> ORGANISM: homo sapiens

<400> SEQUENCE: 332

Cys Leu Val Thr Glu Lys Thr Arg Trp Leu
1               5                   10

<210> SEQ ID NO 333
<211> LENGTH: 11
<212> TYPE: PRT
<213> ORGANISM: homo sapiens

<400> SEQUENCE: 333

Cys Leu Val Thr Glu Lys Thr Arg Trp Leu Gly
1               5                   10

<210> SEQ ID NO 334
<211> LENGTH: 10
<212> TYPE: PRT
<213> ORGANISM: homo sapiens

<400> SEQUENCE: 334

Leu Val Thr Glu Lys Thr Arg Trp Leu Cys
1               5                   10

<210> SEQ ID NO 335
<211> LENGTH: 11
<212> TYPE: PRT
<213> ORGANISM: homo sapiens

<400> SEQUENCE: 335

Leu Val Thr Glu Lys Thr Arg Trp Leu Gly Cys
1               5                   10

<210> SEQ ID NO 336
<211> LENGTH: 9
<212> TYPE: PRT
<213> ORGANISM: homo sapiens

<400> SEQUENCE: 336

Leu Ala Thr Glu Lys Ser Lys Trp Ser
1               5

<210> SEQ ID NO 337
<211> LENGTH: 10
<212> TYPE: PRT
<213> ORGANISM: homo sapiens

<400> SEQUENCE: 337

Leu Ala Thr Glu Lys Ser Lys Trp Ser Gly
1               5                   10

<210> SEQ ID NO 338
<211> LENGTH: 10
<212> TYPE: PRT
```

-continued

<213> ORGANISM: homo sapiens

<400> SEQUENCE: 338

Cys Leu Ala Thr Glu Lys Ser Lys Trp Ser
1               5                   10

<210> SEQ ID NO 339
<211> LENGTH: 11
<212> TYPE: PRT
<213> ORGANISM: homo sapiens

<400> SEQUENCE: 339

Cys Leu Ala Thr Glu Lys Ser Lys Trp Ser Gly
1               5                   10

<210> SEQ ID NO 340
<211> LENGTH: 10
<212> TYPE: PRT
<213> ORGANISM: homo sapiens

<400> SEQUENCE: 340

Leu Ala Thr Glu Lys Ser Lys Trp Ser Cys
1               5                   10

<210> SEQ ID NO 341
<211> LENGTH: 11
<212> TYPE: PRT
<213> ORGANISM: homo sapiens

<400> SEQUENCE: 341

Leu Ala Thr Glu Lys Ser Lys Trp Ser Gly Cys
1               5                   10

<210> SEQ ID NO 342
<211> LENGTH: 9
<212> TYPE: PRT
<213> ORGANISM: homo sapiens

<400> SEQUENCE: 342

Leu Leu Thr Glu Lys Ser Lys Trp Ser
1               5

<210> SEQ ID NO 343
<211> LENGTH: 10
<212> TYPE: PRT
<213> ORGANISM: homo sapiens

<400> SEQUENCE: 343

Leu Leu Thr Glu Lys Ser Lys Trp Ser Gly
1               5                   10

<210> SEQ ID NO 344
<211> LENGTH: 10
<212> TYPE: PRT
<213> ORGANISM: homo sapiens

<400> SEQUENCE: 344

Cys Leu Leu Thr Glu Lys Ser Lys Trp Ser
1               5                   10

<210> SEQ ID NO 345
<211> LENGTH: 11
<212> TYPE: PRT
<213> ORGANISM: homo sapiens

```
<400> SEQUENCE: 345

Cys Leu Leu Thr Glu Lys Ser Lys Trp Ser Gly
1               5                   10

<210> SEQ ID NO 346
<211> LENGTH: 10
<212> TYPE: PRT
<213> ORGANISM: homo sapiens

<400> SEQUENCE: 346

Leu Leu Thr Glu Lys Ser Lys Trp Ser Cys
1               5                   10

<210> SEQ ID NO 347
<211> LENGTH: 11
<212> TYPE: PRT
<213> ORGANISM: homo sapiens

<400> SEQUENCE: 347

Leu Leu Thr Glu Lys Ser Lys Trp Ser Gly Cys
1               5                   10

<210> SEQ ID NO 348
<211> LENGTH: 9
<212> TYPE: PRT
<213> ORGANISM: homo sapiens

<400> SEQUENCE: 348

Leu Leu Thr Glu Lys Ser Lys Trp Ser
1               5

<210> SEQ ID NO 349
<211> LENGTH: 9
<212> TYPE: PRT
<213> ORGANISM: homo sapiens

<400> SEQUENCE: 349

Leu Val Thr Glu Lys Ser Lys Trp Ser
1               5

<210> SEQ ID NO 350
<211> LENGTH: 10
<212> TYPE: PRT
<213> ORGANISM: homo sapiens

<400> SEQUENCE: 350

Leu Val Thr Glu Lys Ser Lys Trp Ser Gly
1               5                   10

<210> SEQ ID NO 351
<211> LENGTH: 10
<212> TYPE: PRT
<213> ORGANISM: homo sapiens

<400> SEQUENCE: 351

Cys Leu Val Thr Glu Lys Ser Lys Trp Ser
1               5                   10

<210> SEQ ID NO 352
<211> LENGTH: 11
<212> TYPE: PRT
<213> ORGANISM: homo sapiens

<400> SEQUENCE: 352
```

```
Cys Leu Val Thr Glu Lys Ser Lys Trp Ser Gly
1               5                   10

<210> SEQ ID NO 353
<211> LENGTH: 10
<212> TYPE: PRT
<213> ORGANISM: homo sapiens

<400> SEQUENCE: 353

Leu Val Thr Glu Lys Ser Lys Trp Ser Cys
1               5                   10

<210> SEQ ID NO 354
<211> LENGTH: 11
<212> TYPE: PRT
<213> ORGANISM: homo sapiens

<400> SEQUENCE: 354

Leu Val Thr Glu Lys Ser Lys Trp Ser Gly Cys
1               5                   10

<210> SEQ ID NO 355
<211> LENGTH: 9
<212> TYPE: PRT
<213> ORGANISM: homo sapiens

<400> SEQUENCE: 355

Leu Met Thr Glu Lys Ser Lys Trp Ser
1               5

<210> SEQ ID NO 356
<211> LENGTH: 10
<212> TYPE: PRT
<213> ORGANISM: homo sapiens

<400> SEQUENCE: 356

Leu Met Thr Glu Lys Ser Lys Trp Ser Gly
1               5                   10

<210> SEQ ID NO 357
<211> LENGTH: 10
<212> TYPE: PRT
<213> ORGANISM: homo sapiens

<400> SEQUENCE: 357

Cys Leu Met Thr Glu Lys Ser Lys Trp Ser
1               5                   10

<210> SEQ ID NO 358
<211> LENGTH: 11
<212> TYPE: PRT
<213> ORGANISM: homo sapiens

<400> SEQUENCE: 358

Cys Leu Met Thr Glu Lys Ser Lys Trp Ser Gly
1               5                   10

<210> SEQ ID NO 359
<211> LENGTH: 10
<212> TYPE: PRT
<213> ORGANISM: homo sapiens

<400> SEQUENCE: 359

Leu Met Thr Glu Lys Ser Lys Trp Ser Cys
1               5                   10
```

```
<210> SEQ ID NO 360
<211> LENGTH: 11
<212> TYPE: PRT
<213> ORGANISM: homo sapiens

<400> SEQUENCE: 360

Leu Met Thr Glu Lys Ser Lys Trp Ser Gly Cys
1               5                   10

<210> SEQ ID NO 361
<211> LENGTH: 9
<212> TYPE: PRT
<213> ORGANISM: homo sapiens

<400> SEQUENCE: 361

Leu Pro Thr Glu Lys Ser Lys Trp Ser
1               5

<210> SEQ ID NO 362
<211> LENGTH: 10
<212> TYPE: PRT
<213> ORGANISM: homo sapiens

<400> SEQUENCE: 362

Leu Pro Thr Glu Lys Ser Lys Trp Ser Gly
1               5                   10

<210> SEQ ID NO 363
<211> LENGTH: 10
<212> TYPE: PRT
<213> ORGANISM: homo sapiens

<400> SEQUENCE: 363

Cys Leu Pro Thr Glu Lys Ser Lys Trp Ser
1               5                   10

<210> SEQ ID NO 364
<211> LENGTH: 11
<212> TYPE: PRT
<213> ORGANISM: homo sapiens

<400> SEQUENCE: 364

Cys Leu Pro Thr Glu Lys Ser Lys Trp Ser Gly
1               5                   10

<210> SEQ ID NO 365
<211> LENGTH: 10
<212> TYPE: PRT
<213> ORGANISM: homo sapiens

<400> SEQUENCE: 365

Leu Pro Thr Glu Lys Ser Lys Trp Ser Cys
1               5                   10

<210> SEQ ID NO 366
<211> LENGTH: 11
<212> TYPE: PRT
<213> ORGANISM: homo sapiens

<400> SEQUENCE: 366

Leu Pro Thr Glu Lys Ser Lys Trp Ser Gly Cys
1               5                   10
```

```
<210> SEQ ID NO 367
<211> LENGTH: 9
<212> TYPE: PRT
<213> ORGANISM: homo sapiens

<400> SEQUENCE: 367

Leu Gly Thr Glu Lys Ser Lys Trp Ser
1               5

<210> SEQ ID NO 368
<211> LENGTH: 10
<212> TYPE: PRT
<213> ORGANISM: homo sapiens

<400> SEQUENCE: 368

Leu Gly Thr Glu Lys Ser Lys Trp Ser Gly
1               5                   10

<210> SEQ ID NO 369
<211> LENGTH: 10
<212> TYPE: PRT
<213> ORGANISM: homo sapiens

<400> SEQUENCE: 369

Cys Leu Gly Thr Glu Lys Ser Lys Trp Ser
1               5                   10

<210> SEQ ID NO 370
<211> LENGTH: 11
<212> TYPE: PRT
<213> ORGANISM: homo sapiens

<400> SEQUENCE: 370

Cys Leu Gly Thr Glu Lys Ser Lys Trp Ser Gly
1               5                   10

<210> SEQ ID NO 371
<211> LENGTH: 10
<212> TYPE: PRT
<213> ORGANISM: homo sapiens

<400> SEQUENCE: 371

Leu Gly Thr Glu Lys Ser Lys Trp Ser Cys
1               5                   10

<210> SEQ ID NO 372
<211> LENGTH: 11
<212> TYPE: PRT
<213> ORGANISM: homo sapiens

<400> SEQUENCE: 372

Leu Gly Thr Glu Lys Ser Lys Trp Ser Gly Cys
1               5                   10

<210> SEQ ID NO 373
<211> LENGTH: 9
<212> TYPE: PRT
<213> ORGANISM: homo sapiens

<400> SEQUENCE: 373

Leu Ala Thr Glu Lys Ser Lys Trp Leu
1               5

<210> SEQ ID NO 374
<211> LENGTH: 10
```

```
<212> TYPE: PRT
<213> ORGANISM: homo sapiens

<400> SEQUENCE: 374

Leu Ala Thr Glu Lys Ser Lys Trp Leu Gly
1               5                   10

<210> SEQ ID NO 375
<211> LENGTH: 10
<212> TYPE: PRT
<213> ORGANISM: homo sapiens

<400> SEQUENCE: 375

Cys Leu Ala Thr Glu Lys Ser Lys Trp Leu
1               5                   10

<210> SEQ ID NO 376
<211> LENGTH: 11
<212> TYPE: PRT
<213> ORGANISM: homo sapiens

<400> SEQUENCE: 376

Cys Leu Ala Thr Glu Lys Ser Lys Trp Leu Gly
1               5                   10

<210> SEQ ID NO 377
<211> LENGTH: 10
<212> TYPE: PRT
<213> ORGANISM: homo sapiens

<400> SEQUENCE: 377

Leu Ala Thr Glu Lys Ser Lys Trp Leu Cys
1               5                   10

<210> SEQ ID NO 378
<211> LENGTH: 11
<212> TYPE: PRT
<213> ORGANISM: homo sapiens

<400> SEQUENCE: 378

Leu Ala Thr Glu Lys Ser Lys Trp Leu Gly Cys
1               5                   10

<210> SEQ ID NO 379
<211> LENGTH: 9
<212> TYPE: PRT
<213> ORGANISM: homo sapiens

<400> SEQUENCE: 379

Leu Ala Thr Glu Lys Ser Lys Trp Val
1               5

<210> SEQ ID NO 380
<211> LENGTH: 10
<212> TYPE: PRT
<213> ORGANISM: homo sapiens

<400> SEQUENCE: 380

Leu Ala Thr Glu Lys Ser Lys Trp Val Gly
1               5                   10

<210> SEQ ID NO 381
<211> LENGTH: 10
<212> TYPE: PRT
<213> ORGANISM: homo sapiens
```

-continued

```
<400> SEQUENCE: 381

Cys Leu Ala Thr Glu Lys Ser Lys Trp Val
1               5                   10

<210> SEQ ID NO 382
<211> LENGTH: 11
<212> TYPE: PRT
<213> ORGANISM: homo sapiens

<400> SEQUENCE: 382

Cys Leu Ala Thr Glu Lys Ser Lys Trp Val Gly
1               5                   10

<210> SEQ ID NO 383
<211> LENGTH: 10
<212> TYPE: PRT
<213> ORGANISM: homo sapiens

<400> SEQUENCE: 383

Leu Ala Thr Glu Lys Ser Lys Trp Val Cys
1               5                   10

<210> SEQ ID NO 384
<211> LENGTH: 11
<212> TYPE: PRT
<213> ORGANISM: homo sapiens

<400> SEQUENCE: 384

Leu Ala Thr Glu Lys Ser Lys Trp Val Gly Cys
1               5                   10

<210> SEQ ID NO 385
<211> LENGTH: 9
<212> TYPE: PRT
<213> ORGANISM: homo sapiens

<400> SEQUENCE: 385

Leu Ala Thr Glu Lys Ser Lys Trp Thr
1               5

<210> SEQ ID NO 386
<211> LENGTH: 10
<212> TYPE: PRT
<213> ORGANISM: homo sapiens

<400> SEQUENCE: 386

Leu Ala Thr Glu Lys Ser Lys Trp Thr Gly
1               5                   10

<210> SEQ ID NO 387
<211> LENGTH: 10
<212> TYPE: PRT
<213> ORGANISM: homo sapiens

<400> SEQUENCE: 387

Cys Leu Ala Thr Glu Lys Ser Lys Trp Thr
1               5                   10

<210> SEQ ID NO 388
<211> LENGTH: 11
<212> TYPE: PRT
<213> ORGANISM: homo sapiens

<400> SEQUENCE: 388
```

```
Cys Leu Ala Thr Glu Lys Ser Lys Trp Thr Gly
1               5                   10
```

<210> SEQ ID NO 389
<211> LENGTH: 10
<212> TYPE: PRT
<213> ORGANISM: homo sapiens

<400> SEQUENCE: 389

```
Leu Ala Thr Glu Lys Ser Lys Trp Thr Cys
1               5                   10
```

<210> SEQ ID NO 390
<211> LENGTH: 11
<212> TYPE: PRT
<213> ORGANISM: homo sapiens

<400> SEQUENCE: 390

```
Leu Ala Thr Glu Lys Ser Lys Trp Thr Gly Cys
1               5                   10
```

<210> SEQ ID NO 391
<211> LENGTH: 9
<212> TYPE: PRT
<213> ORGANISM: homo sapiens

<400> SEQUENCE: 391

```
Leu Leu Thr Glu Lys Ser Lys Trp Val
1               5
```

<210> SEQ ID NO 392
<211> LENGTH: 10
<212> TYPE: PRT
<213> ORGANISM: homo sapiens

<400> SEQUENCE: 392

```
Leu Leu Thr Glu Lys Ser Lys Trp Val Gly
1               5                   10
```

<210> SEQ ID NO 393
<211> LENGTH: 10
<212> TYPE: PRT
<213> ORGANISM: homo sapiens

<400> SEQUENCE: 393

```
Cys Leu Leu Thr Glu Lys Ser Lys Trp Val
1               5                   10
```

<210> SEQ ID NO 394
<211> LENGTH: 11
<212> TYPE: PRT
<213> ORGANISM: homo sapiens

<400> SEQUENCE: 394

```
Cys Leu Leu Thr Glu Lys Ser Lys Trp Val Gly
1               5                   10
```

<210> SEQ ID NO 395
<211> LENGTH: 10
<212> TYPE: PRT
<213> ORGANISM: homo sapiens

<400> SEQUENCE: 395

```
Leu Leu Thr Glu Lys Ser Lys Trp Val Cys
```

```
1               5                   10
```

<210> SEQ ID NO 396
<211> LENGTH: 11
<212> TYPE: PRT
<213> ORGANISM: homo sapiens

<400> SEQUENCE: 396

```
Leu Leu Thr Glu Lys Ser Lys Trp Val Gly Cys
1               5                   10
```

<210> SEQ ID NO 397
<211> LENGTH: 9
<212> TYPE: PRT
<213> ORGANISM: homo sapiens

<400> SEQUENCE: 397

```
Leu Val Thr Glu Lys Ser Lys Trp Leu
1               5
```

<210> SEQ ID NO 398
<211> LENGTH: 10
<212> TYPE: PRT
<213> ORGANISM: homo sapiens

<400> SEQUENCE: 398

```
Leu Val Thr Glu Lys Ser Lys Trp Leu Gly
1               5                   10
```

<210> SEQ ID NO 399
<211> LENGTH: 10
<212> TYPE: PRT
<213> ORGANISM: homo sapiens

<400> SEQUENCE: 399

```
Cys Leu Val Thr Glu Lys Ser Lys Trp Leu
1               5                   10
```

<210> SEQ ID NO 400
<211> LENGTH: 11
<212> TYPE: PRT
<213> ORGANISM: homo sapiens

<400> SEQUENCE: 400

```
Cys Leu Val Thr Glu Lys Ser Lys Trp Leu Gly
1               5                   10
```

<210> SEQ ID NO 401
<211> LENGTH: 10
<212> TYPE: PRT
<213> ORGANISM: homo sapiens

<400> SEQUENCE: 401

```
Leu Val Thr Glu Leu Ser Leu Trp Leu Cys
1               5                   10
```

<210> SEQ ID NO 402
<211> LENGTH: 11
<212> TYPE: PRT
<213> ORGANISM: homo sapiens

<400> SEQUENCE: 402

```
Leu Val Thr Glu Lys Ser Lys Trp Leu Gly Cys
1               5                   10
```

```
<210> SEQ ID NO 403
<211> LENGTH: 9
<212> TYPE: PRT
<213> ORGANISM: homo sapiens

<400> SEQUENCE: 403

Leu Ala Thr Glu Lys Ser His Trp Ser
1               5

<210> SEQ ID NO 404
<211> LENGTH: 10
<212> TYPE: PRT
<213> ORGANISM: homo sapiens

<400> SEQUENCE: 404

Leu Ala Thr Glu Lys Ser His Trp Ser Gly
1               5                   10

<210> SEQ ID NO 405
<211> LENGTH: 10
<212> TYPE: PRT
<213> ORGANISM: homo sapiens

<400> SEQUENCE: 405

Cys Leu Ala Thr Glu Lys Ser His Trp Ser
1               5                   10

<210> SEQ ID NO 406
<211> LENGTH: 11
<212> TYPE: PRT
<213> ORGANISM: homo sapiens

<400> SEQUENCE: 406

Cys Leu Ala Thr Glu Lys Ser His Trp Ser Gly
1               5                   10

<210> SEQ ID NO 407
<211> LENGTH: 10
<212> TYPE: PRT
<213> ORGANISM: homo sapiens

<400> SEQUENCE: 407

Leu Ala Thr Glu Lys Ser His Trp Ser Cys
1               5                   10

<210> SEQ ID NO 408
<211> LENGTH: 11
<212> TYPE: PRT
<213> ORGANISM: homo sapiens

<400> SEQUENCE: 408

Leu Ala Thr Glu Lys Ser His Trp Ser Gly Cys
1               5                   10

<210> SEQ ID NO 409
<211> LENGTH: 9
<212> TYPE: PRT
<213> ORGANISM: homo sapiens

<400> SEQUENCE: 409

Leu Leu Thr Glu Lys Ser His Trp Ser
1               5

<210> SEQ ID NO 410
```

```
<211> LENGTH: 10
<212> TYPE: PRT
<213> ORGANISM: homo sapiens

<400> SEQUENCE: 410

Leu Leu Thr Glu Lys Ser His Trp Ser Gly
1               5                   10

<210> SEQ ID NO 411
<211> LENGTH: 10
<212> TYPE: PRT
<213> ORGANISM: homo sapiens

<400> SEQUENCE: 411

Cys Leu Leu Thr Glu Lys Ser His Trp Ser
1               5                   10

<210> SEQ ID NO 412
<211> LENGTH: 11
<212> TYPE: PRT
<213> ORGANISM: homo sapiens

<400> SEQUENCE: 412

Cys Leu Leu Thr Glu Lys Ser His Trp Ser Gly
1               5                   10

<210> SEQ ID NO 413
<211> LENGTH: 10
<212> TYPE: PRT
<213> ORGANISM: homo sapiens

<400> SEQUENCE: 413

Leu Leu Thr Glu Lys Ser His Trp Ser Cys
1               5                   10

<210> SEQ ID NO 414
<211> LENGTH: 11
<212> TYPE: PRT
<213> ORGANISM: homo sapiens

<400> SEQUENCE: 414

Leu Leu Thr Glu Lys Ser His Trp Ser Gly Cys
1               5                   10

<210> SEQ ID NO 415
<211> LENGTH: 9
<212> TYPE: PRT
<213> ORGANISM: homo sapiens

<400> SEQUENCE: 415

Leu Leu Thr Glu Lys Ser His Trp Ser
1               5

<210> SEQ ID NO 416
<211> LENGTH: 9
<212> TYPE: PRT
<213> ORGANISM: homo sapiens

<400> SEQUENCE: 416

Leu Val Thr Glu Lys Ser His Trp Ser
1               5

<210> SEQ ID NO 417
<211> LENGTH: 10
<212> TYPE: PRT
```

<213> ORGANISM: homo sapiens

<400> SEQUENCE: 417

Leu Val Thr Glu Lys Ser His Trp Ser Gly
1               5                   10

<210> SEQ ID NO 418
<211> LENGTH: 10
<212> TYPE: PRT
<213> ORGANISM: homo sapiens

<400> SEQUENCE: 418

Cys Leu Val Thr Glu Lys Ser His Trp Ser
1               5                   10

<210> SEQ ID NO 419
<211> LENGTH: 11
<212> TYPE: PRT
<213> ORGANISM: homo sapiens

<400> SEQUENCE: 419

Cys Leu Val Thr Glu Lys Ser His Trp Ser Gly
1               5                   10

<210> SEQ ID NO 420
<211> LENGTH: 10
<212> TYPE: PRT
<213> ORGANISM: homo sapiens

<400> SEQUENCE: 420

Leu Val Thr Glu Lys Ser His Trp Ser Cys
1               5                   10

<210> SEQ ID NO 421
<211> LENGTH: 11
<212> TYPE: PRT
<213> ORGANISM: homo sapiens

<400> SEQUENCE: 421

Leu Val Thr Glu Lys Ser His Trp Ser Gly Cys
1               5                   10

<210> SEQ ID NO 422
<211> LENGTH: 9
<212> TYPE: PRT
<213> ORGANISM: homo sapiens

<400> SEQUENCE: 422

Leu Met Thr Glu Lys Ser His Trp Ser
1               5

<210> SEQ ID NO 423
<211> LENGTH: 10
<212> TYPE: PRT
<213> ORGANISM: homo sapiens

<400> SEQUENCE: 423

Leu Met Thr Glu Lys Ser His Trp Ser Gly
1               5                   10

<210> SEQ ID NO 424
<211> LENGTH: 10
<212> TYPE: PRT
<213> ORGANISM: homo sapiens

<400> SEQUENCE: 424

Cys Leu Met Thr Glu Lys Ser His Trp Ser
1               5                   10

<210> SEQ ID NO 425
<211> LENGTH: 11
<212> TYPE: PRT
<213> ORGANISM: homo sapiens

<400> SEQUENCE: 425

Cys Leu Met Thr Glu Lys Ser His Trp Ser Gly
1               5                   10

<210> SEQ ID NO 426
<211> LENGTH: 10
<212> TYPE: PRT
<213> ORGANISM: homo sapiens

<400> SEQUENCE: 426

Leu Met Thr Glu Lys Ser His Trp Ser Cys
1               5                   10

<210> SEQ ID NO 427
<211> LENGTH: 11
<212> TYPE: PRT
<213> ORGANISM: homo sapiens

<400> SEQUENCE: 427

Leu Met Thr Glu Lys Ser His Trp Ser Gly Cys
1               5                   10

<210> SEQ ID NO 428
<211> LENGTH: 9
<212> TYPE: PRT
<213> ORGANISM: homo sapiens

<400> SEQUENCE: 428

Leu Pro Thr Glu Lys Ser His Trp Ser
1               5

<210> SEQ ID NO 429
<211> LENGTH: 10
<212> TYPE: PRT
<213> ORGANISM: homo sapiens

<400> SEQUENCE: 429

Leu Pro Thr Glu Lys Ser His Trp Ser Gly
1               5                   10

<210> SEQ ID NO 430
<211> LENGTH: 10
<212> TYPE: PRT
<213> ORGANISM: homo sapiens

<400> SEQUENCE: 430

Cys Leu Pro Thr Glu Lys Ser His Trp Ser
1               5                   10

<210> SEQ ID NO 431
<211> LENGTH: 11
<212> TYPE: PRT
<213> ORGANISM: homo sapiens

<400> SEQUENCE: 431

```
Cys Leu Pro Thr Glu Lys Ser His Trp Ser Gly
1               5                   10

<210> SEQ ID NO 432
<211> LENGTH: 10
<212> TYPE: PRT
<213> ORGANISM: homo sapiens

<400> SEQUENCE: 432

Leu Pro Thr Glu Lys Ser His Trp Ser Cys
1               5                   10

<210> SEQ ID NO 433
<211> LENGTH: 11
<212> TYPE: PRT
<213> ORGANISM: homo sapiens

<400> SEQUENCE: 433

Leu Pro Thr Glu Lys Ser His Trp Ser Gly Cys
1               5                   10

<210> SEQ ID NO 434
<211> LENGTH: 9
<212> TYPE: PRT
<213> ORGANISM: homo sapiens

<400> SEQUENCE: 434

Leu Gly Thr Glu Lys Ser His Trp Ser
1               5

<210> SEQ ID NO 435
<211> LENGTH: 10
<212> TYPE: PRT
<213> ORGANISM: homo sapiens

<400> SEQUENCE: 435

Leu Glu Thr Glu Lys Ser His Trp Ser Gly
1               5                   10

<210> SEQ ID NO 436
<211> LENGTH: 10
<212> TYPE: PRT
<213> ORGANISM: homo sapiens

<400> SEQUENCE: 436

Cys Leu Gly Thr Glu Lys Ser His Trp Ser
1               5                   10

<210> SEQ ID NO 437
<211> LENGTH: 11
<212> TYPE: PRT
<213> ORGANISM: homo sapiens

<400> SEQUENCE: 437

Cys Leu Gly Thr Glu Lys Ser His Trp Ser Gly
1               5                   10

<210> SEQ ID NO 438
<211> LENGTH: 10
<212> TYPE: PRT
<213> ORGANISM: homo sapiens

<400> SEQUENCE: 438

Leu Gly Thr Glu Lys Ser His Trp Ser Cys
1               5                   10
```

<210> SEQ ID NO 439
<211> LENGTH: 11
<212> TYPE: PRT
<213> ORGANISM: homo sapiens

<400> SEQUENCE: 439

Leu Gly Thr Glu Lys Ser His Trp Ser Gly Cys
1               5                   10

<210> SEQ ID NO 440
<211> LENGTH: 9
<212> TYPE: PRT
<213> ORGANISM: homo sapiens

<400> SEQUENCE: 440

Leu Ala Thr Glu Lys Ser His Trp Leu
1               5

<210> SEQ ID NO 441
<211> LENGTH: 10
<212> TYPE: PRT
<213> ORGANISM: homo sapiens

<400> SEQUENCE: 441

Leu Ala Thr Glu Lys Ser His Trp Leu Gly
1               5                   10

<210> SEQ ID NO 442
<211> LENGTH: 10
<212> TYPE: PRT
<213> ORGANISM: homo sapiens

<400> SEQUENCE: 442

Cys Leu Ala Thr Glu Lys Ser His Trp Leu
1               5                   10

<210> SEQ ID NO 443
<211> LENGTH: 11
<212> TYPE: PRT
<213> ORGANISM: homo sapiens

<400> SEQUENCE: 443

Cys Leu Ala Thr Glu Lys Ser His Trp Leu Gly
1               5                   10

<210> SEQ ID NO 444
<211> LENGTH: 10
<212> TYPE: PRT
<213> ORGANISM: homo sapiens

<400> SEQUENCE: 444

Leu Ala Thr Glu Lys Ser His Trp Leu Cys
1               5                   10

<210> SEQ ID NO 445
<211> LENGTH: 11
<212> TYPE: PRT
<213> ORGANISM: homo sapiens

<400> SEQUENCE: 445

Leu Ala Thr Glu Lys Ser His Trp Leu Gly Cys
1               5                   10

```
<210> SEQ ID NO 446
<211> LENGTH: 9
<212> TYPE: PRT
<213> ORGANISM: homo sapiens

<400> SEQUENCE: 446

Leu Ala Thr Glu Lys Ser His Trp Val
1               5

<210> SEQ ID NO 447
<211> LENGTH: 10
<212> TYPE: PRT
<213> ORGANISM: homo sapiens

<400> SEQUENCE: 447

Leu Ala Thr Glu Lys Ser His Trp Val Gly
1               5                  10

<210> SEQ ID NO 448
<211> LENGTH: 10
<212> TYPE: PRT
<213> ORGANISM: homo sapiens

<400> SEQUENCE: 448

Cys Leu Ala Thr Glu Lys Ser His Trp Val
1               5                  10

<210> SEQ ID NO 449
<211> LENGTH: 11
<212> TYPE: PRT
<213> ORGANISM: homo sapiens

<400> SEQUENCE: 449

Cys Leu Ala Thr Glu Lys Ser His Trp Val Gly
1               5                  10

<210> SEQ ID NO 450
<211> LENGTH: 10
<212> TYPE: PRT
<213> ORGANISM: homo sapiens

<400> SEQUENCE: 450

Leu Ala Thr Glu Lys Ser His Trp Val Cys
1               5                  10

<210> SEQ ID NO 451
<211> LENGTH: 11
<212> TYPE: PRT
<213> ORGANISM: homo sapiens

<400> SEQUENCE: 451

Leu Ala Thr Glu Lys Ser His Trp Val Gly Cys
1               5                  10

<210> SEQ ID NO 452
<211> LENGTH: 9
<212> TYPE: PRT
<213> ORGANISM: homo sapiens

<400> SEQUENCE: 452

Leu Ala Thr Glu Lys Ser His Trp Thr
1               5

<210> SEQ ID NO 453
<211> LENGTH: 10
```

```
<212> TYPE: PRT
<213> ORGANISM: homo sapiens

<400> SEQUENCE: 453

Leu Ala Thr Glu Lys Ser His Trp Thr Gly
1               5                   10

<210> SEQ ID NO 454
<211> LENGTH: 10
<212> TYPE: PRT
<213> ORGANISM: homo sapiens

<400> SEQUENCE: 454

Cys Leu Ala Thr Glu Lys Ser His Trp Thr
1               5                   10

<210> SEQ ID NO 455
<211> LENGTH: 11
<212> TYPE: PRT
<213> ORGANISM: homo sapiens

<400> SEQUENCE: 455

Cys Leu Ala Thr Glu Lys Ser His Trp Thr Gly
1               5                   10

<210> SEQ ID NO 456
<211> LENGTH: 10
<212> TYPE: PRT
<213> ORGANISM: homo sapiens

<400> SEQUENCE: 456

Leu Ala Thr Glu Lys Ser His Trp Thr Cys
1               5                   10

<210> SEQ ID NO 457
<211> LENGTH: 11
<212> TYPE: PRT
<213> ORGANISM: homo sapiens

<400> SEQUENCE: 457

Leu Ala Thr Glu Lys Ser His Trp Thr Gly Cys
1               5                   10

<210> SEQ ID NO 458
<211> LENGTH: 9
<212> TYPE: PRT
<213> ORGANISM: homo sapiens

<400> SEQUENCE: 458

Leu Leu Thr Glu Lys Ser His Trp Val
1               5

<210> SEQ ID NO 459
<211> LENGTH: 10
<212> TYPE: PRT
<213> ORGANISM: homo sapiens

<400> SEQUENCE: 459

Leu Leu Thr Glu Lys Ser His Trp Val Gly
1               5                   10

<210> SEQ ID NO 460
<211> LENGTH: 10
<212> TYPE: PRT
<213> ORGANISM: homo sapiens
```

```
<400> SEQUENCE: 460

Cys Leu Leu Thr Glu Lys Ser His Trp Val
1               5                   10

<210> SEQ ID NO 461
<211> LENGTH: 11
<212> TYPE: PRT
<213> ORGANISM: homo sapiens

<400> SEQUENCE: 461

Cys Leu Leu Thr Glu Lys Ser His Trp Val Gly
1               5                   10

<210> SEQ ID NO 462
<211> LENGTH: 10
<212> TYPE: PRT
<213> ORGANISM: homo sapiens

<400> SEQUENCE: 462

Leu Leu Thr Glu Lys Ser His Trp Val Cys
1               5                   10

<210> SEQ ID NO 463
<211> LENGTH: 11
<212> TYPE: PRT
<213> ORGANISM: homo sapiens

<400> SEQUENCE: 463

Leu Leu Thr Glu Lys Ser His Trp Val Gly Cys
1               5                   10

<210> SEQ ID NO 464
<211> LENGTH: 9
<212> TYPE: PRT
<213> ORGANISM: homo sapiens

<400> SEQUENCE: 464

Leu Val Thr Glu Lys Ser His Trp Leu
1               5

<210> SEQ ID NO 465
<211> LENGTH: 10
<212> TYPE: PRT
<213> ORGANISM: homo sapiens

<400> SEQUENCE: 465

Leu Val Thr Glu Lys Ser His Trp Leu Gly
1               5                   10

<210> SEQ ID NO 466
<211> LENGTH: 10
<212> TYPE: PRT
<213> ORGANISM: homo sapiens

<400> SEQUENCE: 466

Cys Leu Val Thr Glu Lys Ser His Trp Leu
1               5                   10

<210> SEQ ID NO 467
<211> LENGTH: 11
<212> TYPE: PRT
<213> ORGANISM: homo sapiens

<400> SEQUENCE: 467
```

```
Cys Leu Val Thr Glu Lys Ser His Trp Leu Gly
1               5                   10

<210> SEQ ID NO 468
<211> LENGTH: 10
<212> TYPE: PRT
<213> ORGANISM: homo sapiens

<400> SEQUENCE: 468

Leu Val Thr Glu Lys Ser His Trp Leu Cys
1               5                   10

<210> SEQ ID NO 469
<211> LENGTH: 11
<212> TYPE: PRT
<213> ORGANISM: homo sapiens

<400> SEQUENCE: 469

Leu Val Thr Glu Lys Ser His Trp Leu Gly Cys
1               5                   10

<210> SEQ ID NO 470
<211> LENGTH: 10
<212> TYPE: PRT
<213> ORGANISM: homo sapiens

<400> SEQUENCE: 470

Leu Ala Thr Glu Lys Ser Arg Trp Ser Pro
1               5                   10

<210> SEQ ID NO 471
<211> LENGTH: 11
<212> TYPE: PRT
<213> ORGANISM: homo sapiens

<400> SEQUENCE: 471

Cys Leu Ala Thr Glu Lys Ser Arg Trp Ser Pro
1               5                   10

<210> SEQ ID NO 472
<211> LENGTH: 11
<212> TYPE: PRT
<213> ORGANISM: homo sapiens

<400> SEQUENCE: 472

Leu Ala Thr Glu Lys Ser Arg Trp Ser Pro Cys
1               5                   10

<210> SEQ ID NO 473
<211> LENGTH: 10
<212> TYPE: PRT
<213> ORGANISM: homo sapiens

<400> SEQUENCE: 473

Leu Leu Thr Glu Lys Ser Arg Trp Ser Pro
1               5                   10

<210> SEQ ID NO 474
<211> LENGTH: 11
<212> TYPE: PRT
<213> ORGANISM: homo sapiens

<400> SEQUENCE: 474

Cys Leu Leu Thr Glu Lys Ser Arg Trp Ser Pro
```

-continued

```
1               5                  10

<210> SEQ ID NO 475
<211> LENGTH: 11
<212> TYPE: PRT
<213> ORGANISM: homo sapiens

<400> SEQUENCE: 475

Leu Leu Thr Glu Lys Ser Arg Trp Ser Pro Cys
1               5                  10

<210> SEQ ID NO 476
<211> LENGTH: 10
<212> TYPE: PRT
<213> ORGANISM: homo sapiens

<400> SEQUENCE: 476

Leu Val Thr Glu Lys Ser Arg Trp Ser Pro
1               5                  10

<210> SEQ ID NO 477
<211> LENGTH: 11
<212> TYPE: PRT
<213> ORGANISM: homo sapiens

<400> SEQUENCE: 477

Cys Leu Val Thr Glu Lys Ser Arg Trp Ser Pro
1               5                  10

<210> SEQ ID NO 478
<211> LENGTH: 11
<212> TYPE: PRT
<213> ORGANISM: homo sapiens

<400> SEQUENCE: 478

Leu Val Thr Glu Lys Ser Arg Trp Ser Pro Cys
1               5                  10

<210> SEQ ID NO 479
<211> LENGTH: 10
<212> TYPE: PRT
<213> ORGANISM: homo sapiens

<400> SEQUENCE: 479

Leu Met Thr Glu Lys Ser Arg Trp Ser Pro
1               5                  10

<210> SEQ ID NO 480
<211> LENGTH: 11
<212> TYPE: PRT
<213> ORGANISM: homo sapiens

<400> SEQUENCE: 480

Cys Leu Met Thr Glu Lys Ser Arg Trp Ser Pro
1               5                  10

<210> SEQ ID NO 481
<211> LENGTH: 11
<212> TYPE: PRT
<213> ORGANISM: homo sapiens

<400> SEQUENCE: 481

Leu Met Thr Glu Lys Ser Arg Trp Ser Pro Cys
1               5                  10
```

```
<210> SEQ ID NO 482
<211> LENGTH: 10
<212> TYPE: PRT
<213> ORGANISM: homo sapiens

<400> SEQUENCE: 482

Leu Gly Thr Glu Lys Ser Arg Trp Ser Pro
1               5                   10

<210> SEQ ID NO 483
<211> LENGTH: 11
<212> TYPE: PRT
<213> ORGANISM: homo sapiens

<400> SEQUENCE: 483

Cys Leu Gly Thr Glu Lys Ser Arg Trp Ser Pro
1               5                   10

<210> SEQ ID NO 484
<211> LENGTH: 11
<212> TYPE: PRT
<213> ORGANISM: homo sapiens

<400> SEQUENCE: 484

Leu Gly Thr Glu Lys Ser Arg Trp Ser Pro Cys
1               5                   10

<210> SEQ ID NO 485
<211> LENGTH: 10
<212> TYPE: PRT
<213> ORGANISM: homo sapiens

<400> SEQUENCE: 485

Leu Ala Thr Glu Lys Ser Arg Trp Leu Pro
1               5                   10

<210> SEQ ID NO 486
<211> LENGTH: 11
<212> TYPE: PRT
<213> ORGANISM: homo sapiens

<400> SEQUENCE: 486

Cys Leu Ala Thr Glu Lys Ser Arg Trp Leu Pro
1               5                   10

<210> SEQ ID NO 487
<211> LENGTH: 11
<212> TYPE: PRT
<213> ORGANISM: homo sapiens

<400> SEQUENCE: 487

Leu Ala Thr Glu Lys Ser Arg Trp Leu Pro Cys
1               5                   10

<210> SEQ ID NO 488
<211> LENGTH: 10
<212> TYPE: PRT
<213> ORGANISM: homo sapiens

<400> SEQUENCE: 488

Leu Ala Thr Glu Lys Ser Arg Trp Val Pro
1               5                   10

<210> SEQ ID NO 489
```

```
<211> LENGTH: 11
<212> TYPE: PRT
<213> ORGANISM: homo sapiens

<400> SEQUENCE: 489

Cys Leu Ala Thr Glu Lys Ser Arg Trp Val Pro
1               5                   10

<210> SEQ ID NO 490
<211> LENGTH: 11
<212> TYPE: PRT
<213> ORGANISM: homo sapiens

<400> SEQUENCE: 490

Leu Ala Thr Glu Lys Ser Arg Trp Val Pro Cys
1               5                   10

<210> SEQ ID NO 491
<211> LENGTH: 10
<212> TYPE: PRT
<213> ORGANISM: homo sapiens

<400> SEQUENCE: 491

Leu Ala Thr Glu Lys Ser Arg Trp Thr Pro
1               5                   10

<210> SEQ ID NO 492
<211> LENGTH: 11
<212> TYPE: PRT
<213> ORGANISM: homo sapiens

<400> SEQUENCE: 492

Cys Leu Ala Thr Glu Lys Ser Arg Trp Thr Pro
1               5                   10

<210> SEQ ID NO 493
<211> LENGTH: 11
<212> TYPE: PRT
<213> ORGANISM: homo sapiens

<400> SEQUENCE: 493

Leu Ala Thr Glu Lys Ser Arg Trp Thr Pro Cys
1               5                   10

<210> SEQ ID NO 494
<211> LENGTH: 10
<212> TYPE: PRT
<213> ORGANISM: homo sapiens

<400> SEQUENCE: 494

Leu Leu Thr Glu Lys Ser Arg Trp Val Pro
1               5                   10

<210> SEQ ID NO 495
<211> LENGTH: 11
<212> TYPE: PRT
<213> ORGANISM: homo sapiens

<400> SEQUENCE: 495

Cys Leu Leu Thr Glu Lys Ser Arg Trp Val Pro
1               5                   10

<210> SEQ ID NO 496
<211> LENGTH: 11
<212> TYPE: PRT
```

-continued

<213> ORGANISM: homo sapiens

<400> SEQUENCE: 496

Leu Leu Thr Glu Lys Ser Arg Trp Val Pro Cys
1               5                   10

<210> SEQ ID NO 497
<211> LENGTH: 10
<212> TYPE: PRT
<213> ORGANISM: homo sapiens

<400> SEQUENCE: 497

Leu Val Thr Glu Lys Ser Arg Trp Leu Pro
1               5                   10

<210> SEQ ID NO 498
<211> LENGTH: 11
<212> TYPE: PRT
<213> ORGANISM: homo sapiens

<400> SEQUENCE: 498

Cys Leu Val Thr Glu Lys Ser Arg Trp Leu Pro
1               5                   10

<210> SEQ ID NO 499
<211> LENGTH: 11
<212> TYPE: PRT
<213> ORGANISM: homo sapiens

<400> SEQUENCE: 499

Leu Val Thr Glu Lys Ser Arg Trp Leu Pro Cys
1               5                   10

<210> SEQ ID NO 500
<211> LENGTH: 10
<212> TYPE: PRT
<213> ORGANISM: homo sapiens

<400> SEQUENCE: 500

Leu Ala Thr Glu Lys Ser Arg Trp Ser Ala
1               5                   10

<210> SEQ ID NO 501
<211> LENGTH: 11
<212> TYPE: PRT
<213> ORGANISM: homo sapiens

<400> SEQUENCE: 501

Cys Leu Ala Thr Glu Lys Ser Arg Trp Ser Ala
1               5                   10

<210> SEQ ID NO 502
<211> LENGTH: 11
<212> TYPE: PRT
<213> ORGANISM: homo sapiens

<400> SEQUENCE: 502

Leu Ala Thr Glu Lys Ser Arg Trp Ser Ala Cys
1               5                   10

<210> SEQ ID NO 503
<211> LENGTH: 10
<212> TYPE: PRT
<213> ORGANISM: homo sapiens

```
<400> SEQUENCE: 503

Leu Leu Thr Glu Lys Ser Arg Trp Ser Ala
1               5                   10

<210> SEQ ID NO 504
<211> LENGTH: 11
<212> TYPE: PRT
<213> ORGANISM: homo sapiens

<400> SEQUENCE: 504

Cys Leu Leu Thr Glu Lys Ser Arg Trp Ser Ala
1               5                   10

<210> SEQ ID NO 505
<211> LENGTH: 11
<212> TYPE: PRT
<213> ORGANISM: homo sapiens

<400> SEQUENCE: 505

Leu Leu Thr Glu Lys Ser Arg Trp Ser Ala Cys
1               5                   10

<210> SEQ ID NO 506
<211> LENGTH: 10
<212> TYPE: PRT
<213> ORGANISM: homo sapiens

<400> SEQUENCE: 506

Leu Val Thr Glu Lys Ser Arg Trp Ser Ala
1               5                   10

<210> SEQ ID NO 507
<211> LENGTH: 11
<212> TYPE: PRT
<213> ORGANISM: homo sapiens

<400> SEQUENCE: 507

Cys Leu Val Thr Glu Lys Ser Arg Trp Ser Ala
1               5                   10

<210> SEQ ID NO 508
<211> LENGTH: 11
<212> TYPE: PRT
<213> ORGANISM: homo sapiens

<400> SEQUENCE: 508

Leu Val Thr Glu Lys Ser Arg Trp Ser Ala Cys
1               5                   10

<210> SEQ ID NO 509
<211> LENGTH: 10
<212> TYPE: PRT
<213> ORGANISM: homo sapiens

<400> SEQUENCE: 509

Leu Met Thr Glu Lys Ser Arg Trp Ser Ala
1               5                   10

<210> SEQ ID NO 510
<211> LENGTH: 11
<212> TYPE: PRT
<213> ORGANISM: homo sapiens

<400> SEQUENCE: 510
```

```
Cys Leu Met Thr Glu Lys Ser Arg Trp Ser Ala
1               5                   10
```

<210> SEQ ID NO 511
<211> LENGTH: 11
<212> TYPE: PRT
<213> ORGANISM: homo sapiens

<400> SEQUENCE: 511

```
Leu Met Thr Glu Lys Ser Arg Trp Ser Ala Cys
1               5                   10
```

<210> SEQ ID NO 512
<211> LENGTH: 10
<212> TYPE: PRT
<213> ORGANISM: homo sapiens

<400> SEQUENCE: 512

```
Leu Gly Thr Glu Lys Ser Arg Trp Ser Ala
1               5                   10
```

<210> SEQ ID NO 513
<211> LENGTH: 11
<212> TYPE: PRT
<213> ORGANISM: homo sapiens

<400> SEQUENCE: 513

```
Cys Leu Gly Thr Glu Lys Ser Arg Trp Ser Ala
1               5                   10
```

<210> SEQ ID NO 514
<211> LENGTH: 11
<212> TYPE: PRT
<213> ORGANISM: homo sapiens

<400> SEQUENCE: 514

```
Leu Gly Thr Glu Lys Ser Arg Trp Ser Ala Cys
1               5                   10
```

<210> SEQ ID NO 515
<211> LENGTH: 10
<212> TYPE: PRT
<213> ORGANISM: homo sapiens

<400> SEQUENCE: 515

```
Leu Ala Thr Glu Lys Ser Arg Trp Leu Ala
1               5                   10
```

<210> SEQ ID NO 516
<211> LENGTH: 11
<212> TYPE: PRT
<213> ORGANISM: homo sapiens

<400> SEQUENCE: 516

```
Cys Leu Ala Thr Glu Lys Ser Arg Trp Leu Ala
1               5                   10
```

<210> SEQ ID NO 517
<211> LENGTH: 11
<212> TYPE: PRT
<213> ORGANISM: homo sapiens

<400> SEQUENCE: 517

```
Leu Ala Thr Glu Lys Ser Arg Trp Leu Ala Cys
1               5                   10
```

<210> SEQ ID NO 518
<211> LENGTH: 10
<212> TYPE: PRT
<213> ORGANISM: homo sapiens

<400> SEQUENCE: 518

Leu Ala Thr Glu Lys Ser Arg Trp Val Ala
1               5                   10

<210> SEQ ID NO 519
<211> LENGTH: 11
<212> TYPE: PRT
<213> ORGANISM: homo sapiens

<400> SEQUENCE: 519

Cys Leu Ala Thr Glu Lys Ser Arg Trp Val Ala
1               5                   10

<210> SEQ ID NO 520
<211> LENGTH: 11
<212> TYPE: PRT
<213> ORGANISM: homo sapiens

<400> SEQUENCE: 520

Leu Ala Thr Glu Lys Ser Arg Trp Val Ala Cys
1               5                   10

<210> SEQ ID NO 521
<211> LENGTH: 10
<212> TYPE: PRT
<213> ORGANISM: homo sapiens

<400> SEQUENCE: 521

Leu Ala Thr Glu Lys Ser Arg Trp Thr Ala
1               5                   10

<210> SEQ ID NO 522
<211> LENGTH: 11
<212> TYPE: PRT
<213> ORGANISM: homo sapiens

<400> SEQUENCE: 522

Cys Leu Ala Thr Glu Lys Ser Arg Trp Thr Ala
1               5                   10

<210> SEQ ID NO 523
<211> LENGTH: 11
<212> TYPE: PRT
<213> ORGANISM: homo sapiens

<400> SEQUENCE: 523

Leu Ala Thr Glu Lys Ser Arg Trp Thr Ala Cys
1               5                   10

<210> SEQ ID NO 524
<211> LENGTH: 10
<212> TYPE: PRT
<213> ORGANISM: homo sapiens

<400> SEQUENCE: 524

Leu Leu Thr Glu Lys Ser Arg Trp Val Ala
1               5                   10

```
<210> SEQ ID NO 525
<211> LENGTH: 11
<212> TYPE: PRT
<213> ORGANISM: homo sapiens

<400> SEQUENCE: 525

Cys Leu Leu Thr Glu Lys Ser Arg Trp Val Ala
1               5                   10

<210> SEQ ID NO 526
<211> LENGTH: 11
<212> TYPE: PRT
<213> ORGANISM: homo sapiens

<400> SEQUENCE: 526

Leu Leu Thr Glu Lys Ser Arg Trp Val Ala Cys
1               5                   10

<210> SEQ ID NO 527
<211> LENGTH: 10
<212> TYPE: PRT
<213> ORGANISM: homo sapiens

<400> SEQUENCE: 527

Leu Val Thr Glu Lys Ser Arg Trp Leu Ala
1               5                   10

<210> SEQ ID NO 528
<211> LENGTH: 11
<212> TYPE: PRT
<213> ORGANISM: homo sapiens

<400> SEQUENCE: 528

Cys Leu Val Thr Glu Lys Ser Arg Trp Leu Ala
1               5                   10

<210> SEQ ID NO 529
<211> LENGTH: 11
<212> TYPE: PRT
<213> ORGANISM: homo sapiens

<400> SEQUENCE: 529

Leu Val Thr Glu Lys Ser Arg Trp Leu Ala Cys
1               5                   10

<210> SEQ ID NO 530
<211> LENGTH: 9
<212> TYPE: PRT
<213> ORGANISM: homo sapiens

<400> SEQUENCE: 530

Leu Ala Thr Val Lys Ser Arg Trp Ser
1               5

<210> SEQ ID NO 531
<211> LENGTH: 10
<212> TYPE: PRT
<213> ORGANISM: homo sapiens

<400> SEQUENCE: 531

Leu Ala Thr Val Lys Ser Arg Trp Ser Gly
1               5                   10

<210> SEQ ID NO 532
<211> LENGTH: 10
```

```
<212> TYPE: PRT
<213> ORGANISM: homo sapiens

<400> SEQUENCE: 532

Lys Ala Leu Glu Glu Lys Lys Gly Asn Tyr
1               5                   10

<210> SEQ ID NO 533
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 533

Xaa Leu Ala Thr Glu Lys Ser Arg Trp Ser Xaa
1               5                   10

<210> SEQ ID NO 534
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 534

Xaa Leu Ala Thr Glu Lys Ser Arg Trp Ser Gly Xaa
1               5                   10

<210> SEQ ID NO 535
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 535

Xaa Leu Ala Thr Glu Lys Ser Arg Trp Val Xaa
1               5                   10

<210> SEQ ID NO 536
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys
```

```
<400> SEQUENCE: 536

Xaa Leu Ala Thr Glu Lys Ser Arg Trp Val Gly Xaa
1               5                   10

<210> SEQ ID NO 537
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 537

Xaa Leu Ala Thr Glu Lys Ser Arg Trp Leu Xaa
1               5                   10

<210> SEQ ID NO 538
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 538

Xaa Leu Ala Thr Glu Lys Ser Arg Trp Leu Gly Xaa
1               5                   10

<210> SEQ ID NO 539
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 539

Xaa Leu Leu Thr Glu Lys Ser Arg Trp Ser Xaa
1               5                   10

<210> SEQ ID NO 540
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 540

Xaa Leu Leu Thr Glu Lys Ser Arg Trp Ser Gly Xaa
```

```
1               5                   10
```

<210> SEQ ID NO 541
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 541

```
Xaa Leu Leu Thr Glu Lys Ser Arg Trp Val Xaa
1               5                   10
```

<210> SEQ ID NO 542
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 542

```
Xaa Leu Leu Thr Glu Lys Ser Arg Trp Val Gly Xaa
1               5                   10
```

<210> SEQ ID NO 543
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 543

```
Xaa Leu Leu Thr Glu Lys Arg Arg Trp Leu Xaa
1               5                   10
```

<210> SEQ ID NO 544
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 544

```
Xaa Leu Leu Thr Glu Lys Ser Arg Trp Leu Gly Xaa
1               5                   10
```

```
<210> SEQ ID NO 545
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 545

Xaa Leu Val Thr Glu Lys Ser Arg Trp Ser Xaa
1               5                   10

<210> SEQ ID NO 546
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 546

Xaa Leu Val Thr Glu Lys Ser Arg Trp Ser Gly Xaa
1               5                   10

<210> SEQ ID NO 547
<211> LENGTH: 11
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 547

Xaa Leu Val Thr Glu Lys Ser Arg Trp Val Xaa
1               5                   10

<210> SEQ ID NO 548
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 548

Xaa Leu Val Thr Glu Lys Ser Arg Trp Val Gly Xaa
1               5                   10

<210> SEQ ID NO 549
<211> LENGTH: 11
<212> TYPE: PRT
```

```
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (11)..(11)
<223> OTHER INFORMATION: can be absent or cys

<400> SEQUENCE: 549

Xaa Leu Val Thr Glu Lys Ser Arg Trp Leu Xaa
1               5                   10

<210> SEQ ID NO 550
<211> LENGTH: 12
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: can be absent or cys
<220> FEATURE:
<221> NAME/KEY: MISC_FEATURE
<222> LOCATION: (12)..(12)
<223> OTHER INFORMATION: can be absent or cys

<400> SEQUENCE: 550

Xaa Leu Val Thr Glu Lys Ser Arg Trp Leu Gly Xaa
1               5                   10
```